(12) United States Patent
Carl et al.

(10) Patent No.: US 9,277,929 B2
(45) Date of Patent: Mar. 8, 2016

(54) SYSTEMS, DEVICES AND APPARATUSES FOR BONY FIXATION AND DISK REPAIR AND REPLACEMENT AND METHODS RELATED THERETO

(71) Applicant: K2M, Inc., Leesburg, VA (US)

(72) Inventors: Allen Carl, Slingerlands, NY (US); Josef K. Winkler, Wayland, MA (US); Robert Floyd Beisel, Robesonia, PA (US); Spanky Allen Raymond, Uniontown, OH (US); Daniel Stephen Savage, Brecksville, OH (US); Jason John Gromek, Brecksville, OH (US); Carl Michael Nilsson, Moreland Hills, OH (US)

(73) Assignee: K2M, Inc., Leesburg, VA (US)

( * ) Notice: Subject to any disclaimer, the term of this patent is extended or adjusted under 35 U.S.C. 154(b) by 307 days.

(21) Appl. No.: 13/928,415

(22) Filed: Jun. 27, 2013

(65) Prior Publication Data

US 2014/0039504 A1 Feb. 6, 2014

Related U.S. Application Data

(60) Division of application No. 12/087,281, filed as application No. PCT/US2006/049619 on Dec. 29, 2006, now Pat. No. 8,496,660, and a continuation-in-part of application No. 10/968,867, filed on Oct. 18, 2004, now abandoned.

(Continued)

(51) Int. Cl.
| | |
|---|---|
| *A61B 17/16* | (2006.01) |
| *A61B 17/17* | (2006.01) |
| *A61B 17/70* | (2006.01) |

(52) U.S. Cl.
CPC ......... *A61B 17/1671* (2013.01); *A61B 17/1642* (2013.01); *A61B 17/1757* (2013.01); *A61B 17/70* (2013.01); *A61B 17/7011* (2013.01)

(58) Field of Classification Search
CPC ........... A61B 17/1671; A61B 17/1615; A61B 17/1757
USPC .......................................................... 606/98
See application file for complete search history.

(56) References Cited

U.S. PATENT DOCUMENTS

| | | | | |
|---|---|---|---|---|
| 550,783 | A | * | 12/1895 | Elliott et al. ..................... 175/75 |
| 1,630,239 | A | | 5/1927 | Binkley et al. |

(Continued)

FOREIGN PATENT DOCUMENTS

| | | |
|---|---|---|
| WO | WO-9111962 A1 | 8/1991 |
| WO | WO-0067651 A1 | 11/2000 |
| WO | WO-2005037082 A2 | 4/2005 |

OTHER PUBLICATIONS

European Search Report issued Jul. 2, 2012 in connection with EP Application No. EP06849057.2.

(Continued)

*Primary Examiner* — Christian Sevilla
(74) *Attorney, Agent, or Firm* — Locke Lord LLP

(57) ABSTRACT

Disclosed is an apparatus for forming an arcuate channel in one or more segments of a bone, bony structure or adjacent vertebrae of a spine. The apparatus includes, inter alia, a base member which is positioned proximate to the surgical site, a support arm extending proximally from the base member, an arcuate guide member and a drill assembly. The arcuate guide member is slidably mounted to the support arm. The drill assembly is operatively coupled to the support arm and includes a drill bit attached to the distal end of a flexible drive cable. The flexible drive cable extends axially along the support arm and is axially and rotationally movable with respect thereto. The drill bit is operatively coupled to an end of the arcuate guide member such that when the drill assembly is moved distally, the arcuate guide member slides with respect to the support arm and forces the drill bit to traverse an arcuate path.

35 Claims, 52 Drawing Sheets

Related U.S. Application Data

(60) Provisional application No. 60/512,134, filed on Oct. 17, 2003, provisional application No. 60/754,843, filed on Dec. 29, 2005.

(56) References Cited

U.S. PATENT DOCUMENTS

| | | | |
|---|---|---|---|
| 2,960,892 A | 11/1960 | Spraka | |
| 3,426,364 A | 2/1969 | Lumb | |
| 4,059,115 A * | 11/1977 | Jumashev et al. | 606/82 |
| 4,135,506 A | 1/1979 | Ulrich | |
| 4,312,337 A * | 1/1982 | Donohue | 606/80 |
| 4,335,715 A | 6/1982 | Kirkley | |
| 4,773,402 A | 9/1988 | Asher et al. | |
| 4,790,303 A | 12/1988 | Steffee | |
| 4,834,757 A | 5/1989 | Brantigan | |
| 4,907,577 A | 3/1990 | Wu | |
| 4,941,466 A | 7/1990 | Romano | |
| 5,002,546 A | 3/1991 | Romano | |
| 5,017,057 A | 5/1991 | Kryger | |
| 5,030,220 A | 7/1991 | Howland | |
| 5,047,055 A | 9/1991 | Bao et al. | |
| 5,330,468 A | 7/1994 | Burkhart | |
| 5,330,479 A | 7/1994 | Whitmore | |
| 5,352,224 A | 10/1994 | Westermann | |
| 5,355,588 A | 10/1994 | Brandenburg, Jr. et al. | |
| 5,415,661 A | 5/1995 | Holmes | |
| 5,423,826 A | 6/1995 | Coates et al. | |
| 5,425,772 A | 6/1995 | Brantigan | |
| 5,445,639 A | 8/1995 | Kuslich et al. | |
| 5,509,918 A | 4/1996 | Romano | |
| 5,527,316 A | 6/1996 | Stone et al. | |
| 5,545,164 A | 8/1996 | Howland | |
| 5,591,165 A | 1/1997 | Jackson | |
| 5,591,235 A | 1/1997 | Kuslich | |
| 5,700,265 A | 12/1997 | Romano | |
| 5,709,511 A | 1/1998 | Esmailzadeh | |
| 5,765,289 A | 6/1998 | Schulz et al. | |
| 5,797,909 A * | 8/1998 | Michelson | 606/914 |
| 5,824,093 A | 10/1998 | Ray et al. | |
| D401,335 S | 11/1998 | Koros et al. | |
| 5,895,183 A | 4/1999 | McDaniel et al. | |
| 5,899,908 A | 5/1999 | Kuslich et al. | |
| 5,928,267 A | 7/1999 | Bonutti et al. | |
| 5,974,674 A | 11/1999 | Kelly | |
| 6,004,326 A * | 12/1999 | Castro et al. | 606/99 |
| 6,056,749 A | 5/2000 | Kuslich | |
| 6,241,769 B1 | 6/2001 | Nicholson et al. | |
| 6,264,695 B1 | 7/2001 | Stoy | |
| 6,267,679 B1 | 7/2001 | Romano | |
| RE37,479 E | 12/2001 | Kuslich | |
| 6,342,056 B1 | 1/2002 | Mac-Thiong et al. | |
| 6,425,919 B1 | 7/2002 | Lambrecht | |
| 6,517,544 B1 | 2/2003 | Michelson | |
| 6,558,386 B1 * | 5/2003 | Cragg | 606/279 |
| 6,558,390 B2 * | 5/2003 | Cragg | 606/80 |
| 6,575,979 B1 * | 6/2003 | Cragg | 606/86 R |
| 6,592,559 B1 | 7/2003 | Pakter et al. | |
| 6,593,625 B2 | 7/2003 | Christiansen et al. | |
| 6,607,530 B1 * | 8/2003 | Carl et al. | 606/914 |
| 6,740,090 B1 * | 5/2004 | Cragg et al. | 606/79 |
| 6,790,210 B1 | 9/2004 | Cragg et al. | |
| 6,805,697 B1 | 10/2004 | Helm et al. | |
| 6,923,811 B1 | 8/2005 | Carl et al. | |
| 7,354,453 B2 | 4/2008 | McAfee | |
| 7,594,917 B2 * | 9/2009 | Whittaker et al. | 606/98 |
| 7,611,537 B2 | 11/2009 | Carls et al. | |
| 8,021,401 B2 | 9/2011 | Carl et al. | |
| 8,357,198 B2 | 1/2013 | McGraw et al. | |
| 8,486,078 B2 * | 7/2013 | Carl et al. | 606/87 |
| 8,496,660 B2 * | 7/2013 | Carl et al. | 606/80 |
| 8,721,647 B2 * | 5/2014 | Carl et al. | 606/80 |
| 8,845,642 B2 * | 9/2014 | Carl et al. | 606/87 |
| 2001/0049527 A1 * | 12/2001 | Cragg | 606/61 |
| 2002/0004683 A1 | 1/2002 | Michelson | |
| 2002/0019626 A1 * | 2/2002 | Sharkey et al. | 606/15 |
| 2002/0090999 A1 | 7/2002 | Romano | |
| 2002/0133179 A1 | 9/2002 | McDevitt et al. | |
| 2002/0173796 A1 * | 11/2002 | Cragg | 606/86 |
| 2003/0004517 A1 * | 1/2003 | Anderson | 606/90 |
| 2003/0181915 A1 * | 9/2003 | Serhan | 606/79 |
| 2003/0191474 A1 * | 10/2003 | Cragg et al. | 606/79 |
| 2003/0220641 A1 | 11/2003 | Thelen et al. | |
| 2004/0039384 A1 | 2/2004 | Boehm et al. | |
| 2004/0059333 A1 | 3/2004 | Carl et al. | |
| 2004/0092933 A1 * | 5/2004 | Shaolian et al. | 606/61 |
| 2004/0092993 A1 | 5/2004 | Teitelbaum et al. | |
| 2004/0158325 A1 | 8/2004 | Errico et al. | |
| 2004/0225366 A1 | 11/2004 | Eisermann et al. | |
| 2005/0033292 A1 * | 2/2005 | Teitelbaum et al. | 606/53 |
| 2005/0137601 A1 * | 6/2005 | Assell et al. | 606/79 |
| 2005/0177168 A1 | 8/2005 | Brunnett et al. | |
| 2005/0203624 A1 | 9/2005 | Serhan et al. | |
| 2005/0246023 A1 | 11/2005 | Yeung | |
| 2005/0256578 A1 | 11/2005 | Blatt et al. | |
| 2005/0261695 A1 * | 11/2005 | Cragg et al. | 606/86 |
| 2005/0267481 A1 * | 12/2005 | Carl et al. | 606/79 |
| 2006/0004369 A1 * | 1/2006 | Patel et al. | 606/79 |
| 2006/0074425 A1 * | 4/2006 | Sutterlin et al. | 606/79 |
| 2006/0084844 A1 * | 4/2006 | Nehls | 600/227 |
| 2006/0206116 A1 | 9/2006 | Yeung | |
| 2006/0235388 A1 | 10/2006 | Justis et al. | |
| 2007/0027545 A1 | 2/2007 | Carls et al. | |
| 2007/0055260 A1 * | 3/2007 | Cragg | 606/79 |
| 2007/0167951 A1 | 7/2007 | Ainsworth et al. | |
| 2008/0086140 A1 * | 4/2008 | Wolf | 606/79 |
| 2008/0208196 A1 | 8/2008 | Daum | |
| 2009/0005816 A1 | 1/2009 | Denardo et al. | |
| 2009/0076511 A1 * | 3/2009 | Osman | 606/80 |
| 2009/0187191 A1 * | 7/2009 | Carl et al. | 606/80 |
| 2010/0114098 A1 | 5/2010 | Carl | |
| 2010/0268237 A1 * | 10/2010 | Carl et al. | 606/87 |
| 2011/0196497 A1 | 8/2011 | Helm et al. | |
| 2012/0116411 A1 * | 5/2012 | Carl et al. | 606/96 |
| 2012/0158150 A1 | 6/2012 | Siegal | |
| 2013/0079879 A1 | 3/2013 | Suh | |
| 2014/0012261 A1 * | 1/2014 | Nita et al. | 606/79 |
| 2014/0012379 A1 * | 1/2014 | Carl et al. | 623/17.16 |
| 2014/0039504 A1 * | 2/2014 | Carl et al. | 606/80 |

OTHER PUBLICATIONS

European Search Report issued Apr. 19, 2012 in connection with EP Application No. EP07716784.9.
International Search Report issued Apr. 20, 2005 in connection with PCT Application No. PCT/US2004/034526.
International Search Report and Written Opinion issued Oct. 17, 2007 in connection with PCT Application No. PCT/US2006/049619.
International Search Report and Written Opinion issued Oct. 18, 2007 in connection with PCT Application No. PCT/US2007/001402.
International Preliminary Examination Report issued Oct. 16, 2001 in connection with PCT Application No. PCT/US2000/012773.
International Preliminary Examination Report issued Apr. 18, 2006 in connection with PCT Application No. PCT/US2004/034526.
International Preliminary Examination Report issued Jul. 22, 2008 in connection with PCT Application No. PCT/US2007/001402.
International Preliminary Examination Report issued Jul. 1, 2008 in connection with PCT Application No. PCT/US2006/049619.
International Search Report issued Oct. 17, 2000 in connection with PCT Application No. PCT/US2000/012773.
Supplemental Search Report issued Mar. 24, 2006 in connection with EP Application No. EP00935901.9.

* cited by examiner

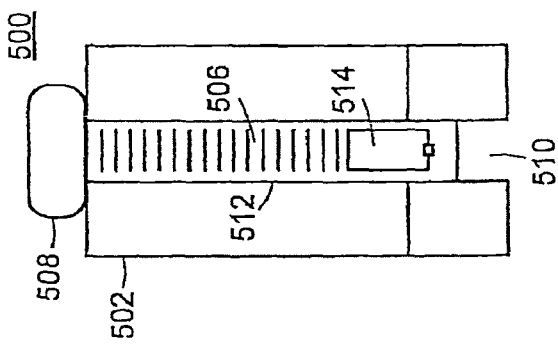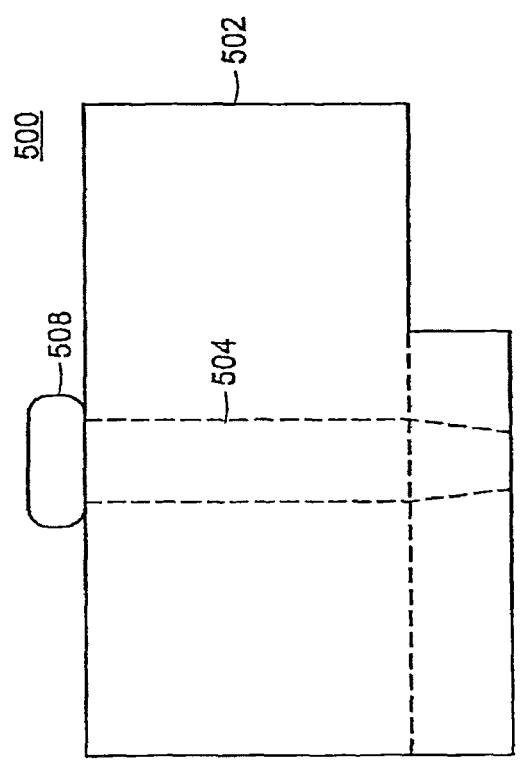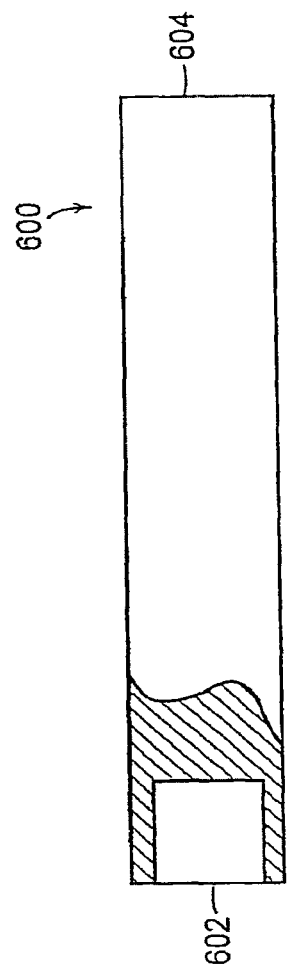

SYSTEMS, DEVICES AND APPARATUSES FOR BONY FIXATION AND DISK REPAIR AND REPLACEMENT AND METHODS RELATED THERETO

CROSS-REFERENCE TO RELATED APPLICATIONS

This application is a divisional of U.S. patent application Ser. No. 12/087,281 filed Dec. 3, 2008, which is a National Stage Entry of PCT/US06/49619 filed Dec. 29, 2006, which claims the benefit of U.S. Provisional Application No. 60/754,843 filed Dec. 29, 2005.

The Ser. No. 12/087,281 application is a continuation-in-part of U.S. patent application Ser. No. 10/968,867, filed Oct. 18, 2004, which claims the benefit of U.S. Provisional Application Ser. No. 60/512,134, filed Oct. 17, 2003. The teachings of each of these applications are incorporated herein by reference.

BACKGROUND OF THE INVENTION

1. Field of the Invention

The present invention generally relates to methods, systems and apparatuses for bony fixation and more particularly to methods, systems and apparatuses adapted for use in fixing the bones of the spine. The present invention also generally relates to methods, systems and devices for augmenting, repairing or replacing the nucleus and/or annulus of an intervertebral disk of a spine, such as the spine of a mammalian body.

2. Background of the Invention

Fixation or fusion of vertebral columns with bone or material, rods or plates is a common, long practiced surgical method for treating a variety of conditions. Many of the existing procedures involve the use of components that protrude outwardly, which may contact and damage a body part, such as the aorta, the vena cava, the sympathetic nerves, the lungs, the esophagus, the intestine and the ureter. Also, many constructions involve components that may loosen and cause undesirable problems, often-necessitating further surgical intervention. Additionally, limiting the success of these procedures are the biomechanical features of the spine itself, whose structure must simultaneously provide support to regions of the body, protect the vertebral nervous system and permit motion in multiple planes.

As indicated above, spinal surgery for spine fusion generally involves using implants and instrumentation to provide support to the affected area of the spine while allowing the bones thereof to fuse. The technology initially evolved using bone chips around and on the top of an area of the spine that had been roughened to simulate a fracture in its consistency. The area, having encountered the bone chips, would then proceed to heal like a fracture, incorporating the bone chips. However, surgical procedures dealing with the spine present notable challenges. For example, bioengineers have been required to identify the various elements of the complex motions that the spine performs, and the components of the complex forces it bears. This complexity has made it difficult to achieve adequate stability and effective healing in surgical procedures directed to the spine.

One surgical technique provided by Cloward, involves cutting a dowel type hole with a saw across or through the moveable intervertebral disc and replacing it with a bone graft that was harvested from the hip bone. This procedure results in a fusion of the adjacent vertebral bodies and limits motion and mobility. However, as a result of the complex motions of the spine, it is often difficult to secure the dowel from displacing. Further, it has become apparent over time, however, that this particular technique does not always yield a secure fusion.

Other techniques have been developed that involve the placement of various hardware elements, including rods and hooks, rods and screws and plates and screws. The dowel technique also has advanced over the past five years or so, with dowels being fabricated from cadaver bone or metals such as titanium or stainless steel. These techniques, whether using hardware, dowels or some combination thereof, have a common goal to enhance stability by diminishing movement, thereby resulting in or enhancing the potential of a fusion of adjacent vertebral bones. For example, in one of these other techniques, the disc is removed and adjacent vertebrae are positioned in a stable position by placing a plate against and traversing them, which plate is secured or anchored to each by means of screws.

In another procedure, cages in the form of two parallel circular or rectangular devices are made out of a material such as titanium or stainless steel and these devices are fenestrated. Bone is packed in the center of the devices that will heal to adjacent bone through each fenestration. In this procedure, the disc space is distracted so all ligamentous structures are taut and the bones are held in their normal maximal position of distraction. Because the cages are implanted in spongy bone, they are more likely to collapse the surrounding bone, thus resulting in loss of distraction and subsequently cage dislodgment.

U.S. Pat. No. 5,591,235 reports a certain spinal fixation device and technique for stabilizing vertebrae. In this technique, a hollow screw is inserted into a hole, preferably a hole saw recess, in each adjoining vertebra. A channel is cut into the vertebrae, which is lined up with corresponding axial slots in the screw. A rod is inserted into the channel and so as to pass through the axial slots in the screw. The rod is secured to each of the screws by means of a locking cap. The rod also is arranged so as to provide a bridge between the hollow screws in the adjoining vertebrae. Certain disadvantages have been surmised using such a device and technique. For example, it has become apparent that the trough in the vertebral bodies destabilizes some of the cortex of the vertebrae body wall, which is the strongest component.

In addition to fixation or fusion of vertebral columns, the prior art also describes methods or other spinal repair procedures, such as discectomy wherein an artificial disc or prosthetic device is placed within the vertebrae of the spine. For such prior art methods and related devices, there have been short comings such as having difficulty in securing the prostheses within the vertebral space or resulting in significant modification or damage to the load bearing surfaces of the vertebrae in an effort to secure the prosthesis.

Another method or other spinal repair technique involves augmentation of the nucleus of an intervertebral disk of the spine. The intervertebral disk is a flexible cartilaginous structure that is disposed between adjacent vertebrae. These disks form joints between the bodies of the vertebrae, which serve to unite adjacent vertebrae and to permit movement between them. These disks also play a role as shock absorbers when force is transmitted along the vertebral column during standing and movement.

Each disk is formed of two parts, a central mass called the nucleus pulpsous (herein the nucleus) and a surrounding fibrous layer, the annulus fibrosus (herein the annulus). The nucleus has a semi-gelatinous consistency, which allows it to become deformed when pressure is placed upon it, enabling the disk to change shape as the vertebral column moves.

There is described in U.S. Pat. Nos. 5,047,055; 5,824,093 6,264,695; the teachings of which are incorporated herein by reference, various techniques and/or prosthetics for use in replacing or augmenting a spinal disc nucleus. Given the structure of the disk and its location between adjacent vertebrae, it is not s simple task to access the nucleus for the insertion of such prosthetics or materials to augment the nucleus. One technique for accessing the nucleus contemplates using the defect in the annulus, however, in practice the defect usually needs to be enlarged to allow the insertion of the prosthetic. Another technique contemplates having the surgeon drill through one of the adjacent bodies using a lateral approach. This another technique relies heavily on the skill and dexterity of the surgeon not to damage surrounding tissues, nerves and blood vessels. Also, the hole formed by such drilling is not easily sealed because of its shape and configuration.

Conventional techniques relating to fixation of the spine and bony structure rely in great part on the skill and dexterity of the surgeon to control the devices and instrumentalities being used to protect surrounding tissues, muscles, nerves and blood vessels from damage during the procedure. This is so because the devices and/or instrumentalities that the surgeon uses during such techniques, themselves do not provided the surgeon with a mechanism to protect the tissues, muscles, nerves and blood vessels surrounding the treatment or target area within the body from coming into contact with the device or instrumentality during the procedure. Consequently, the surgeon must use surgical techniques to relocate tissues, muscles, nerves and blood vessels from the surgical field, if that is possible, and for those which it is not possible, the surgeon must take care in the use of the device or instrumentality to prevent injury. It should be recognized that the surgeon while inserting and retracting or removing the device or instrumentality from the bony structure or spine must exercise such care to prevent injury.

Thus, it would be desirable to provide a new apparatus, system and methods for bony fixation that enhances healing of the bone while providing structural support therefore. It would be particularly desirable to provide such an apparatus, system and method that would involve the use of open surgical or minimally invasive surgical techniques as well as a technique in which the implant burrows in the structure of the bone; more particularly a technique in which the implant burrows in the bone spine, traverses across the disk space, and ends in an adjacent or neighboring vertebrae or vertebras, providing limited or no protrusions. It also would be desirable to provide such an apparatus, system and method where the implant is retained within the bone without requiring external fixation including contour-varying external vertebral wall fixation as compared to conventional devices, as such a device would avoid many of the problems associated with conventional devices such as blood vessel injury, erosion into organs, as well as placement near nerves. It also would be desirable for such apparatuses and systems to be adaptable for use in a wide range of procedures and techniques, including but not limited to augmentation of the nucleus such as by use of prosthetics.

Still further, there is a demand for a new apparatus or device for use in systems and methods for bony fixation or disc repair and augmentation which reduces the need to rely on the skill and dexterity of the surgeon to control such devices and instrumentalities. Moreover, prior known techniques for drilling into the bony structure of the spine utilize drill assemblies which are secured to at least two adjacent vertebrae. Such a mounting arrangement presents problems when attaching to adjacent vertebrae that are not positioned within the same plane due to the natural curvature of the spine. For example, when attempting to stabilize the spine in the lower lumbar region, often the drill must be mounted to the anterior portion of the L5 and S1 vertebrae. Therefore, there it is desirable to provide an apparatus and methods for forming a channel or opening in one of adjacent segments of a bone or bony structure which can be mounted to a single bony structure or vertebrae of a spine.

SUMMARY OF THE INVENTION

The present invention features new methods, apparatuses and devices for fixing adjacent bone segments, segments of a bony structure and adjacent vertebrate of a spine. The methods, apparatuses and devices utilize new apparatuses for forming a channel in a surface of the bone or bony structure segments or adjacent vertebra or a channel submerged within the bone or bony structure segments or adjacent vertebra. In more particular embodiments such apparatuses and methods include forming an arcuate channel. Also the channel formed can receive therein a curved rod or implant member, which also preferably is arcuate, and avoids the associated problems with prior cage or straight rod and screw systems.

The present invention is directed to an apparatus for forming an arcuate channel in one or more segments of a bone, bony structure or adjacent vertebrae of a spine. The apparatus includes, inter alia, a base member which is positioned proximate to the surgical site, a mechanism for fixing the position of the base member relative to the bony, bony structure or vertebrae, a support arm, an arcuate guide member and a drill assembly. The base member has a distal surface adapted to allow placement of the base member proximal or adjacent to one of the bone, bony structure or vertebrae. The support arm extends proximally from the base member and the arcuate guide member is slidably mounted to the support arm.

The drill assembly is operatively coupled to the support arm and includes a drill bit attached to the distal end of a flexible drive cable. The flexible drive cable extends axially along the support arm and is axially and rotationally movable with respect thereto. In a representative embodiment, the support arm is tubular and the flexible drive cable extends substantially along the centerline of the support arm. The drill bit is operatively coupled to an end of the arcuate guide member such that when the drill assembly is moved distally the arcuate guide member slides with respect to the support arm and forces the drill bit to traverse an arcuate path. It is also presently envisioned that the drill assembly includes a flexible outer housing which surrounds the drive cable.

In representative embodiments, the arcuate guide member has a substantially U-shaped cross section in which the flexible outer housing of the drill assembly is disposed. Still further, the arcuate guide member can include first and second arms or rail members which depend from its bottom surface. Each rail member has an arcuate slot formed therein that is adapted to receive guide pins projecting from the support arm and allow the guide member to slide in an arcuate path relative thereto.

It is presently preferred that the support arm includes a handle attached to its proximal end. An actuator mechanism is associated with the proximal end of the support arm or handle for moving the drill assembly between a first position, wherein the drill bit is positioned outside of the bone, bony structure or vertebrae to a second position, wherein the drill bit is disposed within the bone, bony structure or vertebrae. In such embodiments it is considered advantageous to provide a biasing means for returning the drill assembly to the first position from the second position upon the completion of the drilling procedure.

It is also envisioned that the inventive apparatus disclosed herein can further include a mechanism for adjusting the location of the support arm and/or first position of the drill assembly with respect to the base member. Preferably, the adjustment mechanism includes a lateral adjustment mechanism and a axial adjustment mechanism.

The base member can be fixed relative to one of the bone, bony structure or vertebrae using screws which extend through apertures formed in the base member and engage with one of the bone, bony structure or vertebrae.

In a preferred embodiment, the base member has a plurality of through apertures formed therein. In such an embodiment, the base member is configured and arranged so portions thereof proximal an exit of each of the plurality of through apertures contact at least a portion of a surface of the one of the bone, bony structure or vertebra so as to form an enclosed pathway from a top surface of the base to the surface of the one of the bone, bony structure or vertebra. In certain embodiments, the base member includes a soft conformable material on the distal surface thereof to effect a seal against the surface of the bone, bony structure or vertebrae.

The present invention is also directed to a method for forming a channel in one or more segments of a bony structure or adjacent vertebra of a spine. The inventive method includes the steps of, among others, positioning a frame assembly proximal the treatment or surgical site, securing the frame assembly to one segment of the bone or bony structure or adjacent vertebra; and rotating a drill bit in fixed relation to the support arm of the frame assembly. It is envisioned that the frame assembly includes a base member, a support arm extending proximally from the base member, an arcuate guide member slidably mounted to the support arm; and a drill assembly operatively coupled to the support arm which includes a drill bit. The method also includes the step of moving the drill assembly distally so that the arcuate guide member slides with respect to the support arm and forces the drill bit to traverse an arcuate path and form a channel in the surface or sub-surface of the bone, bony structure or vertebra.

Preferably, the step of securing the frame assembly to one segment of the bone or bony structure or adjacent vertebrae includes, mechanically engaging a securing mechanism to the frame assembly and to the adjacent segments of the bone or bony structure or adjacent vertebra, wherein the frame assembly is maintained in fixed relation by such mechanical engagement.

It is envisioned that in representative embodiments of the method, the base member includes a plurality of through apertures, each through aperture including a constricted portion and a plurality of securing members. The plurality of securing members are driven through the through apertures and the constricted portion and into the bone, bony structure or vertebra at the site. In such embodiments, the base member is secured in fixed relation to the bone, bony segments or vertebra by the engagement of the constricted portion with the securing member.

The method can further include the step of determining if the movement of the drill bit in a first direction formed one of a complete channel or a partial channel. In cases where it is determined that a partial channel was formed, the method includes the additional steps of detaching and re-attaching the support arm to the base member such that the arcuate guide member is moveable in a second direction that is different from the first direction and moving the drill bit in the second direction.

Preferably, representative embodiments of the disclosed method also includes the steps of locating an implant in the channel; and attaching the implant within the channel to the bone, bony structure or vertebras. It is envisioned that the attaching includes securing the implant to the bone, bony structure or vertebra using a plurality of securing devices.

The present disclosure also is directed to a method for gaining access to the intervertebral disc space which includes the steps of, inter alia, positioning a frame assembly proximal the treatment or surgical site, securing the frame assembly to one segment of the bone or bony structure or adjacent vertebra; and rotating a drill bit in fixed relation to the support arm of the frame assembly. The frame assembly used in this method includes a base member, a support arm extending proximally from the base member, an arcuate guide member slidably mounted to the support arm; and a drill assembly operatively coupled to the support arm and including a drill bit.

The method also includes the step of moving the drill assembly distally so that the arcuate guide member slides with respect to the support arm and forces the drill bit to traverse an arcuate path to form the channel in the surface or sub-surface of the bone, bony structure or vertebra that communicates with the intreverebral disc space.

Also disclosed is a method for augmenting the nucleus of a disk between vertebral endplates of adjacent vertebral bodies of a spine. The disk augmentation method preferably includes the steps of: positioning a frame assembly proximal the adjacent vertebral bodies and securing the base member of the frame assembly to a single vertebral body. The frame assembly including a base member, a support arm extending proximally from the base member, an arcuate guide member slidably mounted to the support arm, and a drill assembly operatively coupled to the support arm and including a drill bit.

The method also includes the steps of rotating a drill bit in fixed relation to the frame assembly; moving the drill assembly distally so that the arcuate guide member slides with respect to the support arm and forces the drill bit to traverse an arcuate path to form an arcuate preformed aperture in one of the adjacent vertebral bodies that extends through the vertebral endplate of the spine and into the nucleus of the disk, inserting nucleus augmentation material though the preformed aperture and into the nucleus of the disk; and filling at least a portion of the preformed aperture with a non-compressible material.

Preferably, the method step of inserting nuclear augmentation material includes inserting a nucleus prosthetic through the preformed aperture and into the nucleus. It is further envisioned that the method can include the steps of; inserting a annular closure mechanism through the preformed aperture; and positioning the closure mechanism proximal the annulus defect, thereby closing the defect.

The present disclosure also is directed to a system for forming an arcuate channel in one or more segments of a bone, bony structure or adjacent vertebrae of a spine. The disclosed system includes a base member having a distal surface adapted for placement adjacent to one of the bone, bony structure or vertebrae; a mechanism for securing the base member to one of the bone, bony structure or vertebrae; a support arm extending proximally from the base member. Further, an arcuate guide member having a substantially U-shaped cross-section is slidably mounted to the support arm. The system also includes a drill assembly operatively coupled to the support arm which includes a drill bit attached to the distal end of a flexible drive cable which extends axially along the support arm and is axially and rotationally movable with respect thereto. Preferably, the drill bit is operatively coupled to an end of the arcuate guide member such that when the drill assembly is moved distally the arcuate guide member slides with respect to the support arm and forces the drill bit and a portion of the flexible drive cable to traverse an arcuate path.

In further aspects of the present invention, there are featured systems, apparatuses and methods for augmenting, repairing or replacing the nucleus and/or the annulus that embody selected aspects of the frame, base, support arm, guide member and drill assembly herein described, as well as, other such systems and apparatuses described in U.S. Pat. Nos. 6,607,530 and 6,923,811, the teachings of which are incorporated herein by reference. In such systems, apparatuses and methods, the drill is rotated as described herein to form a channel or passage through one of the vertebrae that is adjacent to the disk to be repaired so that the nucleus of the disk can be accessed through the vertebral end plate. The size of the channel or passage formed can be controlled so as to provide the desired or needed amount of access for the surgeon to insert for example, the material or prosthetic into the nucleus as well as other devices or mechanisms (e.g., a patch) that can be used to form a seal or closure at the defect on the annulus. Such control is achieved for example, by adjusting the size of the drill bit to fit a given application. Such a disk repair procedure also can include sealing of the channel, passage or hole formed in the vertebrae using any of a number of techniques known to those skilled in the art, such as for example, inserting bone or bony material into the channel.

It should be recognized that the drilling apparatus, methods and systems of the present invention can be used anteriorly or posteriorly (e.g., transpedicularly or translaterally) and such that the drill bit of such systems, devices or apparatuses can penetrate or enter the vertebral body through the pedicles.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 10A is a side view of a nail removal tool according to one embodiment of the present invention;

FIG. 10B is an end view of the nail removal tool;

FIG. 12 is a side view with a partial cut away of a nail drive tool according to an embodiment of the present invention;

DETAILED DESCRIPTION OF THE PREFERRED EMBODIMENTS

Figure 1:
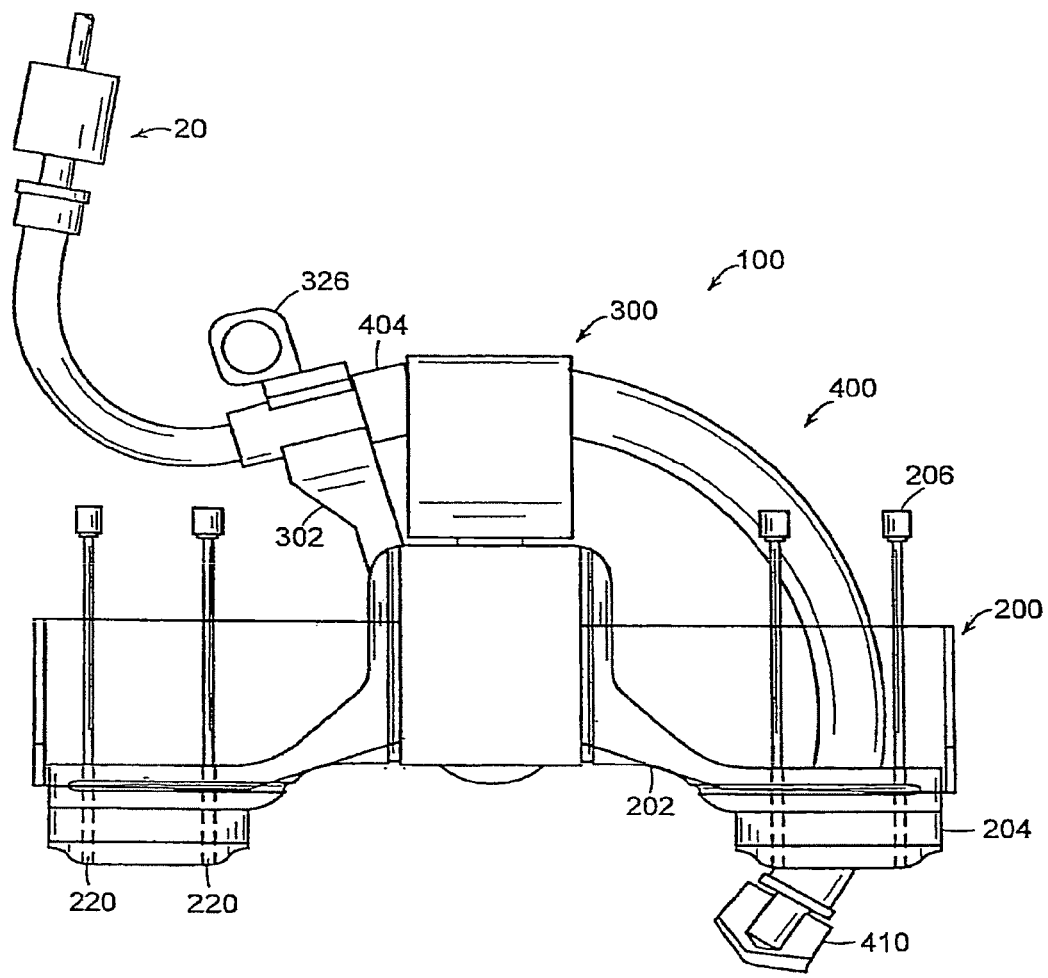
FIG. 1 is a side view of a drilling apparatus according to an aspect of the present invention.
Figure 2:
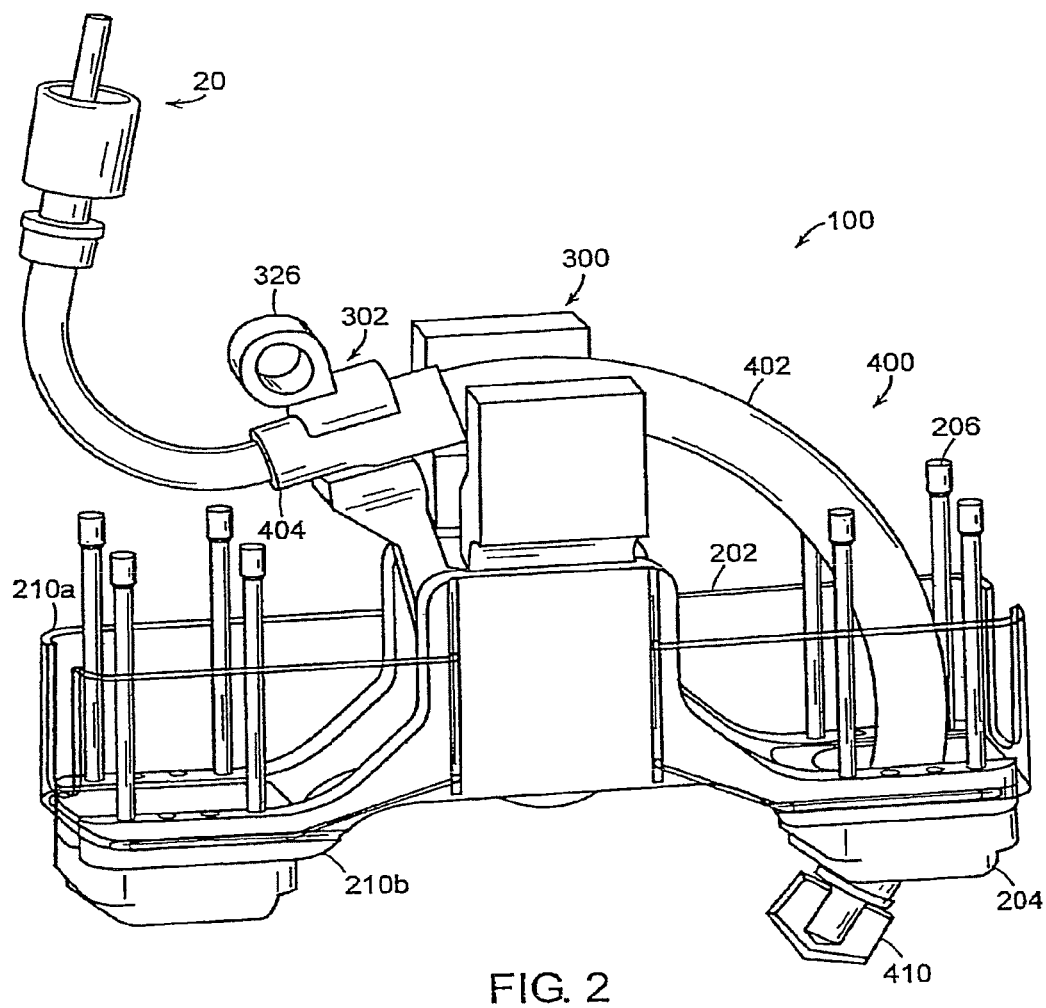
FIG. 2 is one perspective view of the drilling apparatus of FIG. 1.
Figure 3:
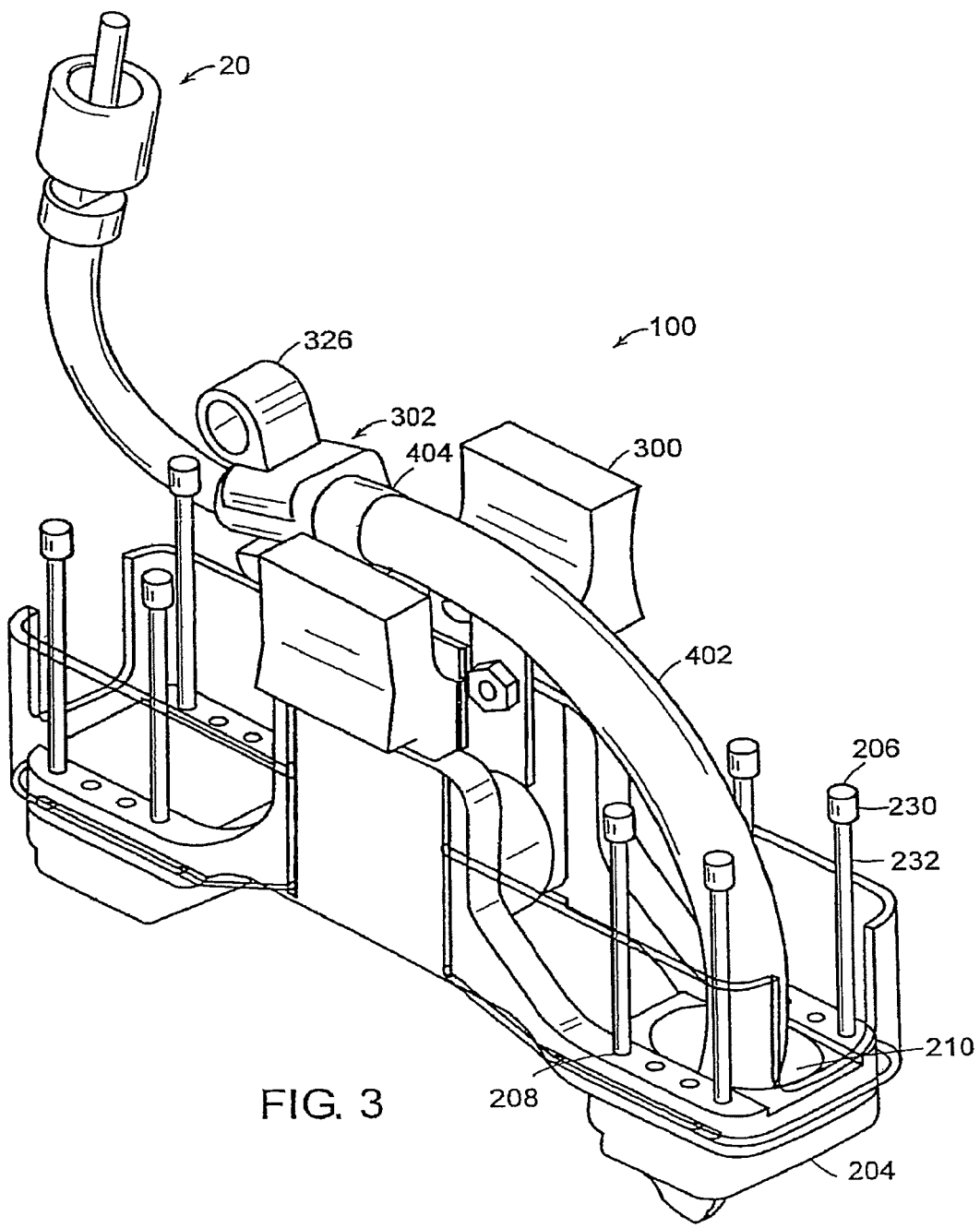
FIG. 3 is another perspective view of the drilling apparatus of FIG. 1.

Referring now to the various figures of the drawing wherein like reference characters refer to like parts, there is shown in FIGS. 1-3 various views of a drilling apparatus 100 according to an aspect of the present invention that is generally comprised of a platform assembly 200, a pivot arm assembly 300 and drill assembly 400. As hereinafter described in more detail, the pivot arm assembly 300 is removably secured to the platform assembly 200 and the platform assembly is removably secured to the bone or bony structure so as to maintain the pivot point of the pivot arm assembly in general fixed relation to the bone or bony structure. The drill assembly 400 is removably secured to the pivot arm assembly 300 so as to maintain the end of the drill assembly including the bit 410 or drill end in fixed relation with respect to the pivot arm 302 of the pivot arm assembly. Consequently, as the pivot arm 302 is rotated about the pivot point, the bit 410 follows a predetermined arcuate, curved or circular path in the bone or bony structure as defined by the length of the pivot arm.

For purposes of illustrating the drilling apparatus 100 of the present invention, reference hereinafter is generally made to the structure and structural features or elements of a mammalian spine, however, this shall not be construed as limiting the use and application of the drilling apparatus of the present invention to these applications. It is contemplated and as such within the scope of the present invention to adapt the drilling apparatus of the present invention and the methods related thereto so the drilling apparatus is used so as to form grooves or arcuate passages in bones or bony structures of the mammalian body in which grooves is received a curved rod or other member as is hereinafter described thereby stabilizing and/or supporting the bone or bony structure.

The platform assembly 200 includes a frame 202, a plurality of first path guards 204 and a mechanism for securing the frame to the bone or bony structure. In the illustrated embodiment, the securing mechanism comprises a plurality of nail members 206 that each pass respectively through each of the frame 202 and the first path guards and so as to be disposed in the bone or bony structure as herein described. In further embodiments, and as hereinafter described, the platform assembly 200 can further include a second path guard 204b, in cases where the drilling apparatus 100 is used to form a groove or recess in an outer surface of the bone or bony structure thereby providing a protective structure between the moving and rotating drill bit 410 and the tissues or other structures or features of the mammalian body (e.g., nerves, blood vessels) that are proximal the bone or bony structure outer surface.

The frame 202 is configured and arranged so as to form an essentially rigid structure and frame work to which the pivot arm assembly 300 is removable attached and at least one and more particularly two through passages 210 that communicate with a corresponding passage in the first path guards 204. The through passages 210 and the corresponding passage in the first path guards 204 are each configured and arranged so as to allow the outer tube member 402 of the drill assembly to pass there through as the pivot arm 302 is being rotated or pivoted about the pivot point. The frame 202 is composed of any one of number of materials known to those skilled in the art that is appropriate for the intended use and the anticipated structural loads that can be imposed during use. In an exemplary embodiment, the frame 202 is made from stainless steel such as a stainless steel bar stock.

The first path guards 204 are secured to the frame 202 so as to extend downwardly from a bottom surface 210b therefrom. Each of the first path guards 204 are arranged so as to include a generally centrally located through passage, through which the outer tube member 402 and the drill bit 410 or burr of the drill assembly 400 are passed. In addition, each of the first path guards 204 are configured and arranged so as to include a plurality of through passages 220, one for each of the nail members 206. Each of the nail member through passages 220 also are preferably formed in the first guard member so as to present constricted holes that firmly grab the nail member within the corresponding through passage. In this way, the gripping action of the through passages and the lateral stiffness of the nail members 206 provides a mechanism for supporting and fixing the frame 202, and in turn the pivot point's relation with respect to the bone, bony structure or spine. In use, each of the nail members 206 are passed through the through aperture 208 in the frame 202 and driven through the through passage 220 of the first path guard 204.

In more particular embodiments, each through passage 220 is configured and arranged so that the passages are over sized with respect to the diameter of the nail members 206 and a portion of the through passage forms a land or raised region comprising a constriction region. More particularly, the constricted region is located above or from the lower end of the through passage such that the pointed ends of each nail member 206 are not exposed when the nail members 206 are initially pressed into the platform assembly 200. In this way, each of the nail members 206 are confined within the first path guard 204 prior to positioning of the platform assembly 200 in the surgical field amidst vital structures or features of the mammalian body.

The first path guards 204 are constructed from any of a number of materials known to those skilled in the art that are appropriate for the intended use and so as to provide a medium that can form a protective barrier between the drill path and the tissues including nerves and blood vessels that are proximal the site of the bone, bony structure or spine to be drilled. In exemplary embodiments, the first path guards 204 are made form a plastic material such as, but not limited to, polycarbonate. In further embodiments, the end of the first path guard 204 proximal the bone, bony structure or spine is configured and arranged so as to include a soft conformal region that contacts and seals against the surface of the bone, bony structure or spine. Alternatively, a conformable material may be disposed in the space, if any, between the base or bottom surface of each first path guard 204 and the opposing surface of the bone, bony structure or spine (e.g., vertebral cortex).

The nail members 206 are configured and arranged so that each extends from a top surface 210a of the frame 200, through the frame and the first path guard 204 and a sufficient distance into the bone, bony structure or spine to fix and secure the frame thereto. In addition, each of the nail members 206 also is configured and arranged so at least a portion thereof has a diameter that is set so that this portion of the nail member is gripped within the constricted region of the through passage 220 of the first path guards 204 as herein described.

Each of the nail members 206 includes a head portion 230 and a shaft portion 232 one end of which is mechanically coupled to the head portion using any of a number of techniques known to those skilled in the art that yields a nail member that is capable of being driven into the bone, bony structure or spine and removed therefrom. In further embodiments, the nail member 206 is formed such that the head portion 230 is integral with the shaft portion 232. In particular embodiments, the head portion 230 is configured and arranged so as to allow the nail member 206 to be driven through and into the bone, bony structure or spine and later removed therefrom. In further embodiments, the head portion 230 is further configured so as to include a through aperture or hole extending generally laterally or radially through the head portion, the through aperture being configured to receive one or more suture lines therein for interoperative locating.

The other end of the shaft portion 232 is configured so as to form a pointed end that is appropriately configured and shaped for insertion into the bone, bony structure or spine and for securing the pointed end and a portion of the shaft member in such bone, bony structure or spine. In illustrative embodiments, the pointed end is configured to form a non-cutting pencil point end that wedges the end into the bone, bony structure or spine.

In the illustrated embodiment, four nail members 206 are driven through each of the first guard members 204 and into the bone or bony structure or spine. This shall not be construed as a limitation as the number and placement of the nail members is not so particularly limited as each end of the frame 202 can be secured to the bone or bony structure using one or more and more particularly two or more nail members 206. It also should be recognized that other mechanisms known to those skilled in the art, such as screws or threaded devices, are contemplated for use with the present invention.

Each of the nail members 206 is composed of any one of number of materials known to those skilled in the art that is appropriate for the intended use and the anticipated structural loads that can be imposed during use. In an exemplary embodiment, the nail member 206 is made from a metal such as stainless steel.

Figure 4A:
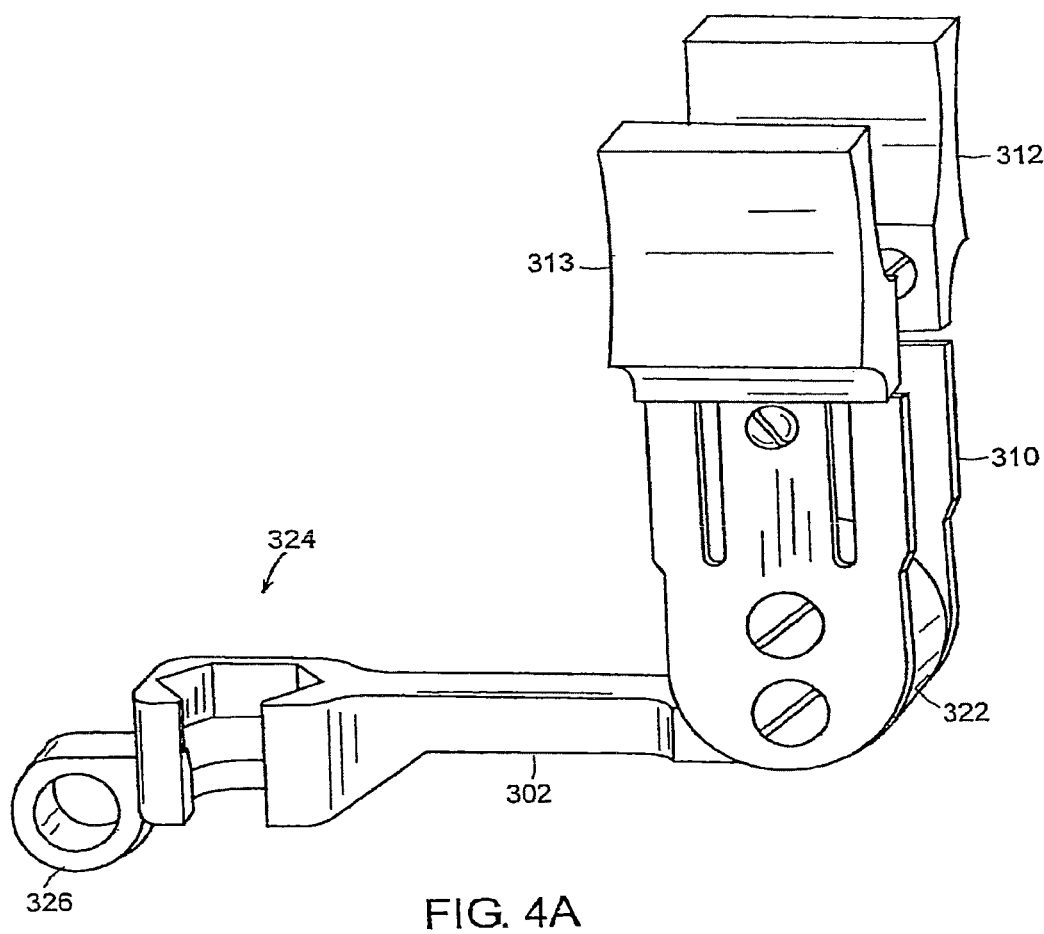
FIG. 4A,B are various perspective views of the pivot arm assembly of the drilling apparatus of FIG. 1.
Figure 4B:
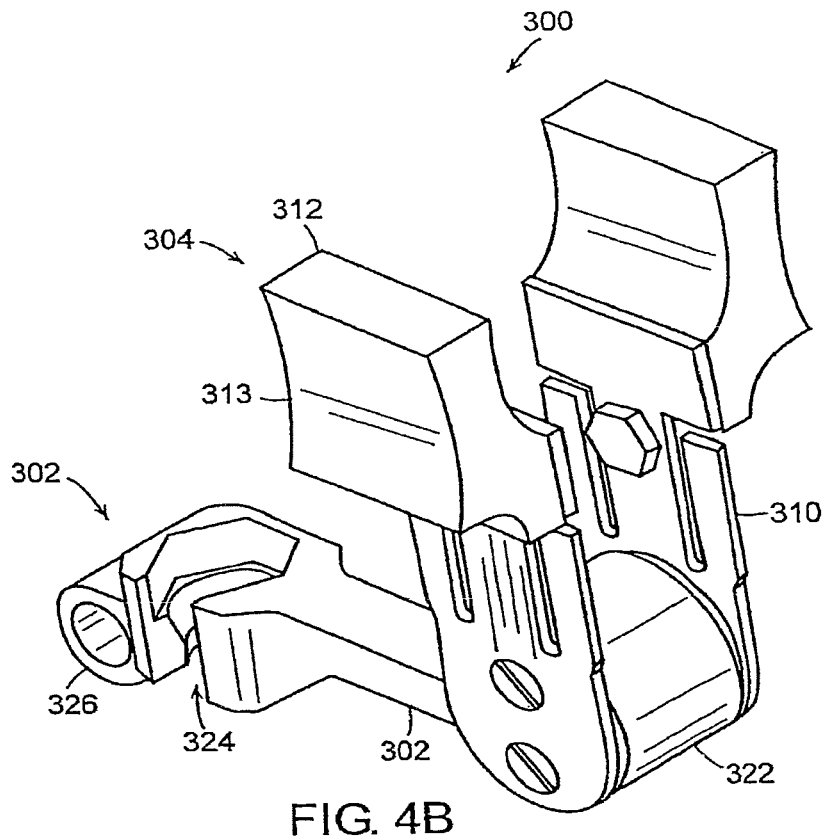
Figure 5:
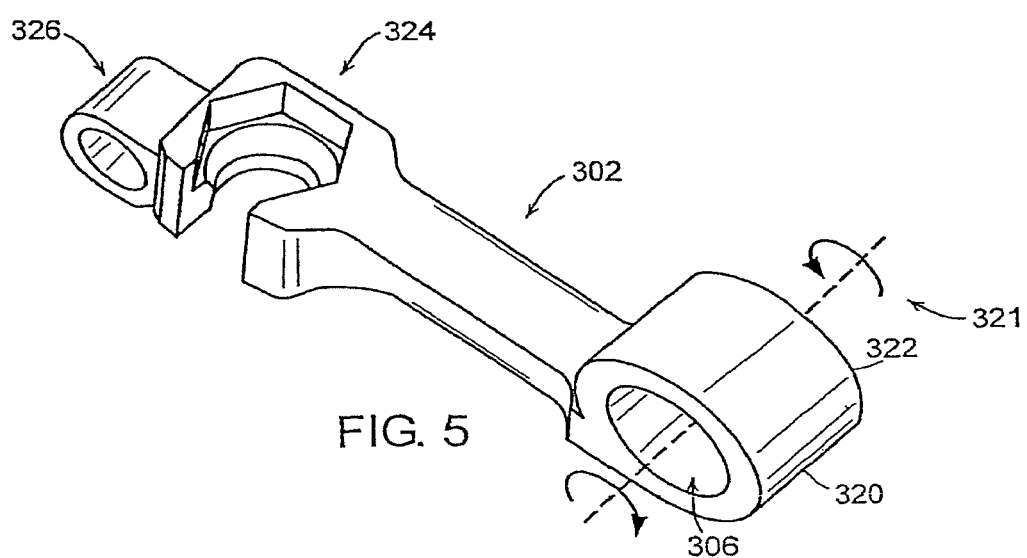
FIG. 5 is a perspective view of the pivot arm of the pivot arm assembly.

Referring now also to FIGS. 4-5, the pivot arm assembly 300 includes a radial arm or pivot arm 302, a pivot pin bracket 304 and a pivot pin 306. The pivot pin bracket 304 includes side plates 310 and finger pads 312 that are secured to the side plates, where the pivot pin extends between the side plates. The pivot pin 306 is received within an aperture 320 in the pivot arm such that the pivot arm can rotate about a pivot axis 321.

The pivot pin bracket 304, more particularly the side plates 310 thereof, is generally configured and arranged so as to secure the pivot arm assembly 300 to the platform assembly 200 so as to prevent the disengagement of the pivot arm assembly and correspondingly the drill assembly 400 from the platform assembly when it is being rotated from the fully retracted position of the pivot arm. More particularly, the side plates thereof are configured and arranged such that the bracket can be removed from the platform assembly 200 when the pivot arm is in the fully retracted position.

In particular embodiments, the side plates 310 are configured so as to form spring members that can slide in mating grooves provided on opposing inside surfaces of the platform assembly frame 202. In addition, the side plates 310 further include binding head screws that engage complimentary holes within the mating grooves to lock the pivot pin bracket 304 in place. A finger pad 312 is secured to an end of each side plate so as to facilitate placement and removal of the pivot pin bracket 304 in the platform assembly. In illustrative embodiments, the finger pads 312 are configured with so as to include concavities 313 that the fingertips of the user can engage to thereby facilitate placement and removal of the pivot pin bracket 304.

The pivot arm 302 is configured and arranged so an end 322 thereof includes an aperture 320 so the pivot arm can be mounted upon the pivot pin 306 such that it can rotate or swing about the pivot pin 306. The pivot arm 302 also is configured and arranged so as to include a mating portion 324 that receives therein and mates with a feature of the drill assembly 400 so as to removably secure the drill assembly to the pivot arm. The mating portion 324 is located distal from the end 322 of the pivot arm 302 that is mounted upon the pivot pin 306. Also, the length of the pivot arm 304, more particularly the distance between the pivot axis 321 and the mating portion 324, establishes or controls the radius of curvature of the hole or recess being formed in the bone, bony structure or spine by the rotation of the pivot arm. It should be noted that this radius of curvature or diameter is different from the diameter of the hole or recess formed by the rotating drill bit 410 or bur. As such, it is contemplated that pivot arms 302 will be provided that have lengths set that are appropriate for the given geometry and physical make-up of the mammalian body.

The platform assembly 200 and pivot arm assembly 300 of the present invention advantageously creates a mechanism that allows tissue, muscle, blood vessels (e.g., aorta) and nerves to pass under and around the platform assembly and also to localize the drilling elements of the drill assembly 400 within the structure of the platform assembly. In addition, the pivot arm assembly 300 in combination with the platform assembly provides a mechanism to control the radial movement or radial motion of the drilling elements of the drill assembly 400 from their insertion into the bone or bony structure as well as the retraction from the bone or bony structure such that the drilling elements traverse a specific radius of curvature during such insertion and retraction. In this way, the drilling apparatus of the present invention also controls the maximum depth within the bone or bony structure the drilling elements can attain during use.

Thus, and in contrast to conventional techniques, devices and instrumentalities, the drilling apparatus 100 of the present invention provides a mechanism that protects tissues, blood vessels and nerves from damage while the drilling elements of the drill assembly 400 are being inserted into and withdrawn from the bone or bony structure as well as assuring that the drilling elements will follow a generally fixed path such that the drilling elements do not come into contact with nor damage the tissues, blood vessels and nerves proximal to and surrounding the bone or bony structure while the hole or recess is being formed in the bone or bony structure. Consequently, the drilling apparatus 100 of the present invention minimizes the potential for damage without having to rely solely on the dexterity or skill of the surgeon, as is done with conventional techniques and devices.

In further embodiments, at least a segment or a part of the mating portion 324 is configured and arranged so as to complement the shape of the drive assembly feature being received therein. For example, and as illustrated, a portion or part of the key 404 of the drill assembly is configured so as to be polygonal in shape and the mating portion 324 is configured so as to include a polygonal shaped recess for receiving therein the hexagonal surfaces of the key. Such polygonal shapes includes but are not limited to a square, triangular, rectangular or hexagonal shapes.

In yet further embodiments, the pivot arm 302 is configured and arranged so as to include a finger grip 326 at or proximal an end of the pivot arm that is opposite to the end 322 mounted upon the pivot pin 306. The finger grip 326 presents a structural element or feature that is configured to allow the thumb and/or fingers of the user to grasp the finger grip so as to thereby control rotation of the pivot arm and to also control the drilling pressure (i.e., pressure being exerted by the drill bit 410 on the bone or bony structure while drilling the hole or recess therein). In illustrated embodiments, the finger grip 326 presents a small tab having bilateral concavities that allow the finger tips to grasp it or a through aperture.

Each of the pivot arm 302, pivot pin 306, side plates 310 and finger pads 312 is composed of any one of number of materials known to those skilled in the art that is appropriate for the intended use and the anticipated structural loads that can be imposed during use. In an exemplary embodiment, any one or more of the foregoing elements of the pivot arm assembly 300 is made from a metal such as stainless steel.

Figure 6:
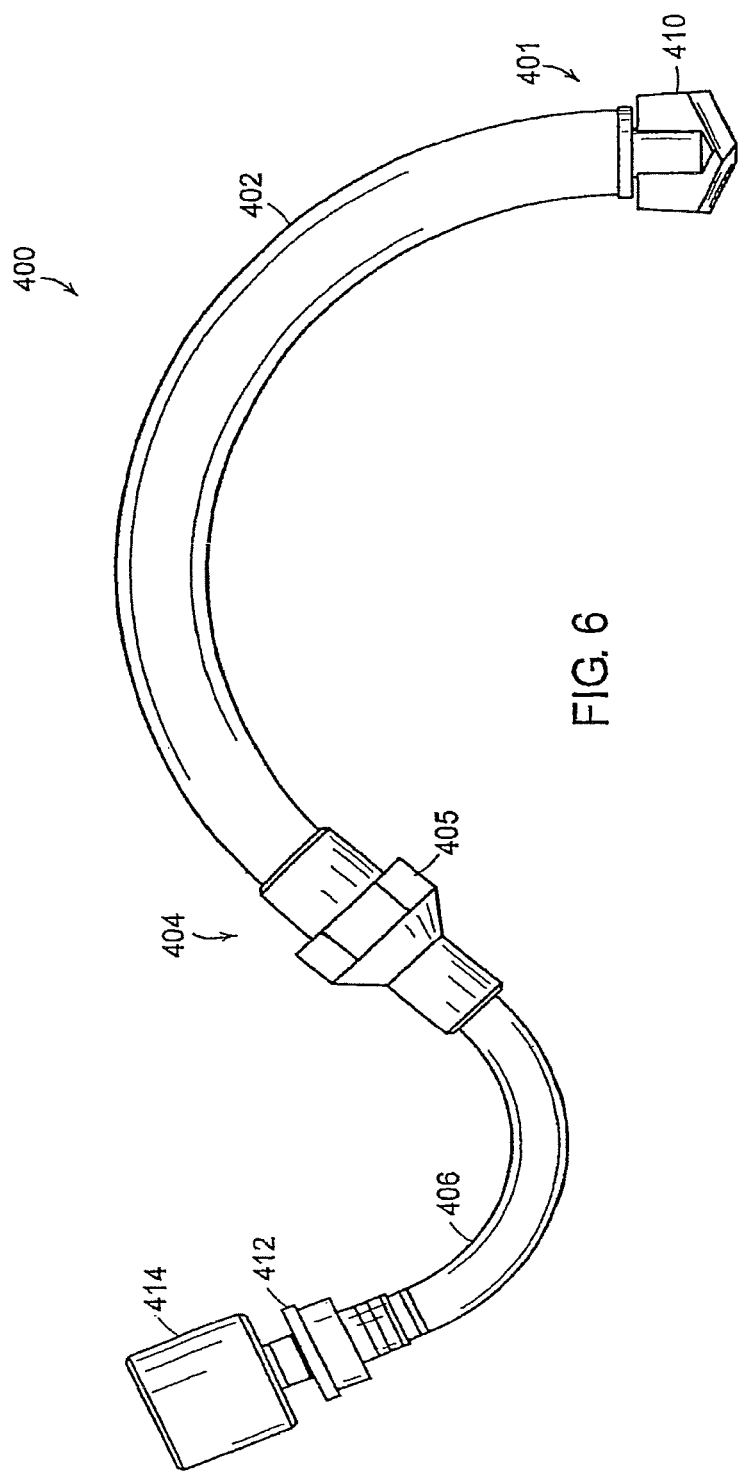
FIG. 6 is a perspective view of the drill assembly of the drilling apparatus and a drive motor connected thereto.
Figure 7:
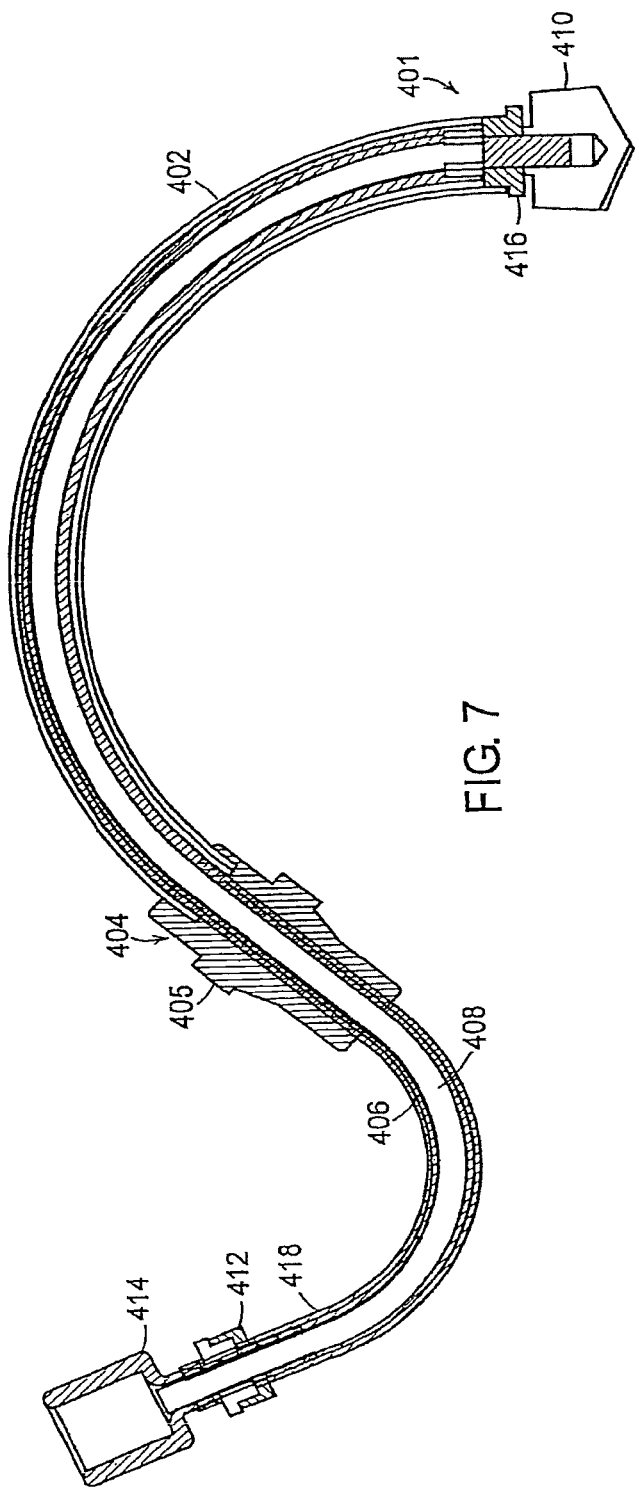
FIG. 7 is a cross-sectional side view of the drill assembly of FIG. 6.
Figure 8:
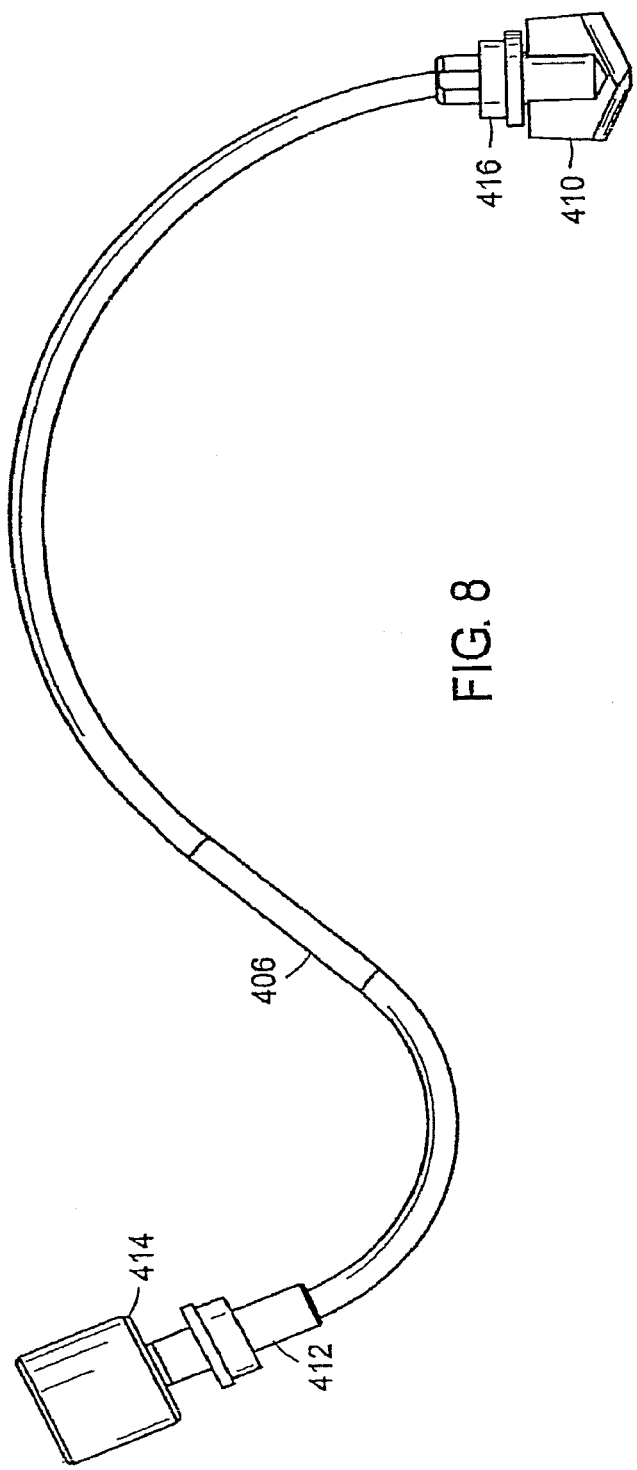
FIG. 8 is a side view of the bit, bearing and drive cable sub-assembly of the drill assembly.
Figure 9:
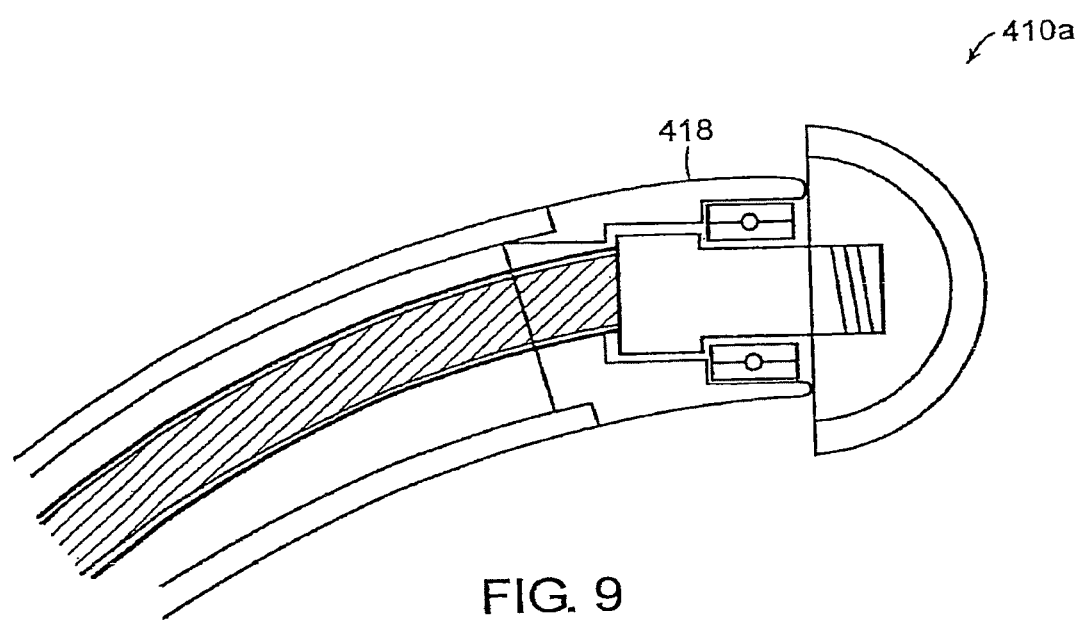
FIG. 9 is a cross-sectional view of the drill assembly end including the bit, illustrating another exemplary bit.

Referring now also to FIGS. 6-7 there is shown a perspective view and a cross-sectional view of drill assembly 400 of the present invention. There also are shown in FIGS. 8-9 various views of portions or segments of such a drill assembly and/or embodiments thereof. The drill assembly 400 generally forms a curved structure, more particularly a curved tubular structure, that is attached to the pivot arm 302 as herein described and which thus swings around the pivot point or pivot axis 321. In use, the drill bit 410 rotates about its axis while this axis is held tangent to and swept along an arc of constant radius as defined by the distance between the mating portion 324 of the pivot arm 302 and the pivot axis 321. This movement results in or yields a toroidal hole.

The drill assembly includes an outer tube member 402, a key 404, a flexible inner housing 406, a drive cable 408, a drill bit 410 or burr, a barbed fitting 412, a drive adapter 414. In further embodiments, the drill assembly includes a distal drive cable bearing 416 and a proximal drive cable bearing 418. Any one of a number of motors 20 or motor drive assemblies as is known in the art having sufficient power (e.g., torque) and rotational speed are coupled to the drive adapter 414 including but not limited to the Micro100 (Linvatech/Hall Surgical 5053-009) or Blachmax (Anspach Blackmax-KT-0). The drive adapter 414 is a swage-type of fitting that is configured and arranged so it can be swaged upon one end of the drive cable 408. The drive adapter 414 also is configured and arranged so as to provide an input end arrangement that can be mechanically coupled to the output end of a variety of motors or motor drive assemblies or drills including those identified herein.

The outer tube member 402 is curved to a predetermined radius of curvature so that the centerline thereof is a set distance from the pivot axis 321 of the pivot arm 302. The key 404 and the distal cable bearing 416 are secured to the outer tube using any of a number of techniques known to those skilled in the art that is appropriate for the materials comprising these elements or features. In exemplary embodiments, the key 404 and the distal cable bearing 416 are secured to the outer tube member by brazing or soldering. In more particular embodiments, the distal drive cable bearing 416 is secured to the outer tube member 402 such that the outer edge of the outer race of the bearing lies in a radial plane from the pivot point, whereby the axis of the drill bit 410 or burr is arranged so as to tangent to the centerline of the arc of the outer tube member.

The key 404 is generally cylindrical in construction and serves to align and anchor the outer tube member 401 to the pivot arm assembly 300, more particularly the pivot arm 302. As indicated herein, a portion 405 of the key 404 is configured so as to provide a surface feature, artifact or contour that complements at least a part of the mating portion 324 of the pivot arm. In the illustrated embodiment, the portion 405 of the key 404 forms an external polygonal feature that mates to the internal polygonal feature provided in the pivot arm mating portion. The key 404 also is configured and arranged so as to be secured to the mating portion using any of a number of techniques known to those skilled in the art. In an exemplary embodiment, a portion of the key is configured so as to include an external thread and a part of the mating portion 324 is configured so as to include a complementary threaded element or feature in an aperture thereof. In use, the key is articulated so as to threadably secure or lock the key 404 to the pivot arm 302. Other techniques for securing, such as brazing, soldering and adhesives are contemplated for use with the present invention.

The key 404 includes a through aperture that is coupled to the inner region or area of the outer tube member 402. The diameter of the key through aperture and the outer tube member are set so as to at least allow the flexible inner housing 406 and the drive cable 408 to pass there through. The flexible inner housing 406 extends from the distal end 401 of the outer tube member 402 to the barbed fitting 412. The flexible inner housing 406 is a generally tubular member of flexible construction, such as Teflon for example, for housing the drive cable 408. In particular embodiments, the flexible inner housing 406 is a small diameter tubular member (i.e., smaller than the inner diameter of the outer tube member) and is secured the key 404 using any of a number of techniques known to those skilled in the art, which are appropriate for the materials of use. In an exemplary embodiment, the flexible inner housing is secured to the key 404 using an adhesive, such as a medical grade adhesive.

The barbed fitting 412 is secured to the end of the flexible inner housing that is opposite to the drill bit 410 using any of a number of techniques known to those skilled in the art, which are appropriate for the materials of use. The end of the barbed fitting 412 being secured to the flexible inner housing 406 also is received within the flexible inner housing. In particular embodiments, the barbed fitting 412 is configured and arranged so the end being received in the flexible inner housing 406 is secured thereto by an interference fit. In further exemplary embodiments, the interference fit is augmented by use of an adhesive, such as a medical grade adhesive.

The proximal drive cable bearing 418 is disposed within the barbed fitting 412 in which is received the drive cable 408. In particular embodiments, the proximal drive cable bearing 418 is retained within the barbed fitting 412 using any of a number of techniques known to those skilled in the art. In an exemplary embodiment, the proximal drive cable bearing is secured to the barbed fitting using one of soldering, brazing or adhesives.

The distal and proximal drive cable bearings 416, 418 are any of a number of bearing assemblies known to those skilled in the art and appropriate for the intended use. In particular embodiments, the distal and proximal drive cable bearing 416, 418 are miniature ball bearing assemblies as is known to those skilled in the art (e.g., SR133zz MSC 35380799, 0.9375" bore, 0.1875" OD, 0.0937" width, double shielded).

In an alternative embodiment, the inner housing is a double curved inner tube of a fixed non-flexible construction. The double curved inner tube has two radii of curvature, the first radius of curvature involves all but the most distal section of the inner tube and the second radius of curvature involves a smaller portion of the inner tube. The second radius of curvature is set so as to bring the path of the drive cable 408 around so as to enter the proximal end of the distal drive cable bearing 416 in the correct direction. In this way, the fixed inner tube can be configured and arranged so as to swing wide and make a turn to enter essentially parallel to the axis of an end fitting being swaged to the end of the inner tube. In this way, fatiguing of the drive cable 408 can be minimized and misalignment of the drive cable and the inner tube proximal the end of the inner tube can be minimized.

Although specific embodiments are described herein for the outer tube member 402 and the inner tube member or flexible inner housing 406 this shall not be considered as particularly limiting. The present invention contemplates adapting the present invention using any of a number of techniques known to those skilled in the art whereby a cable is generally turned through a protected series of rigid or flexible cannulas or tubes such that a bit operably coupled to one end of the cable can turn at an end of the outer tube or cannula.

The drill bit 410 or burr is any of a number of cutting tools or implements known to those skilled in the art and appropriate for the intended use, speed and power developed by the drive motor 20 and the material to be drilled. In particular illustrative embodiments, the drill bit 410 or burr is a spade bit such as that shown in FIGS. 6-8, alternatively and with reference to FIG. 9, the drill bit is a hemispherical bit 410a.

The drive cable 408 is a flexible cable that is more particularly comprised of a large number of smaller strands of an appropriate material, including but not limited to steel, stainless steel, and titanium, that are compound wound using any of a number of techniques known to those skilled in the art so as to yield a flexible cable having the desired width, length, flexibility and strength characteristics. In a particularly illustrative embodiment, the drive cable 408 is a custom wound 1.8 mm (0.072 in.) diameter 7×9 left regular lay strand wound cable. In more particular aspects, the drive cable 408 is manufactured so as to be capable of being rotated or turned at a high rate of speed or revolution while maintaining its flexibility and such that right hand turning of the cable should not result in the unwinding or loosening of construction.

In particular embodiments, the length ("Ldc") of the drive cable 408 shall be controlled so as to maintain a relationship with the length of the portion of the drive cable ("Ldci") that is disposed within the outer cannula or outer tube 402 or correspondingly the arc length of the outer tube. In more particular embodiments, the relationship between the length of the drive cable 408 and the length of the portion of the drive cable within the outer tube 402 satisfies the following relationship $Ldc \leq 4 \times Ldci$; more particularly satisfies the relationship $Ldc \leq 3 \times Ldci$, and more specifically satisfies the relationship $Ldc \leq 2 \times Ldci$. In more specific embodiments, the length of the drive cable 408 is set based on the particular application or material to be drilled. For example, the overall cable length is shortened or lengthened based on the relative hardness of the material in which the channel or opening is to be formed in the bone or bony structure. In further embodiments, the flexible inner housing 406 is configured and arranged so as to have a length that satisfies the foregoing relationships.

Figure 17:
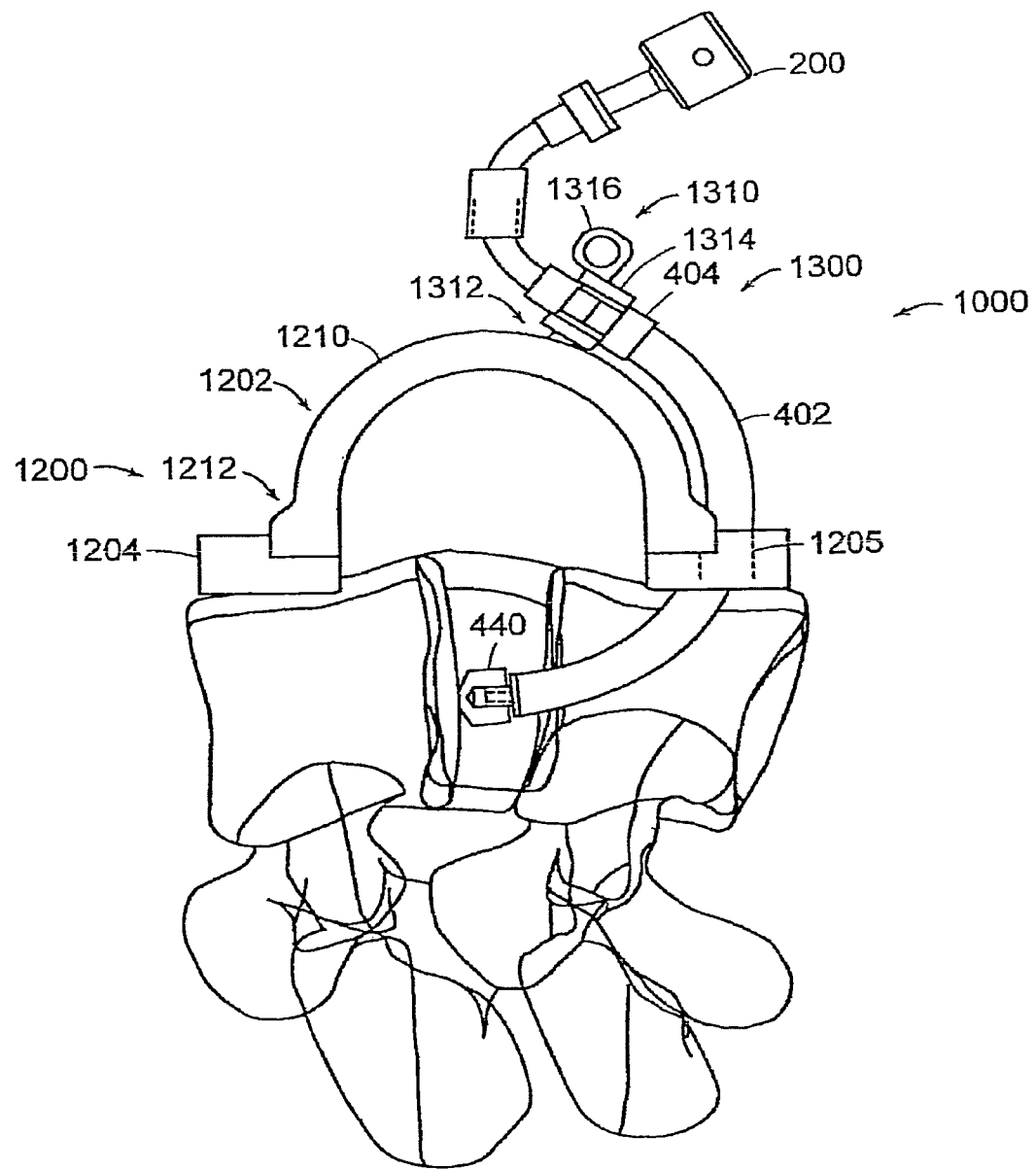
FIG. 17 is a side view of a drilling apparatus according to another aspect of the present invention illustrated disposed upon adjacent vertebral bodies.

Referring now to FIG. 17 there is shown a side view of a drilling apparatus 1000 according to another aspect of the present invention that is illustrated being disposed upon adjacent vertebral bodies. Reference shall be made to FIGS. 1-3 and 6-9 and the discussion related thereto for features and functions not provided in the following discussion. Such a drilling apparatus 1000 includes a platform assembly 1200 and a drill assembly 1300.

The platform assembly 1200 includes a frame member 1202 and a plurality of path guard members 1204 and a mechanism for securing the frame to the bone or bony structure. As with the drilling apparatus illustrated in FIG. 1, the securing mechanism comprises a plurality of nail members 206 that each pass respectively through each of the path guard members 1204 so as to be disposed in the bone or bony structure as herein described. In further embodiments, and as hereinafter described, the platform assembly 1200 can further include a second path guard 205, in cases where the drilling apparatus 1000 is used to form a groove or recess in an outer surface of the bone or bony structure thereby providing a protective structure between the moving and rotating drill bit 410 and the tissues or other structures or features of the mammalian body (e.g., nerves, blood vessels) that are proximal the bone or bony structure outer surface.

The frame member 1202 and the first guard members 1204 are configured and arranged so as to form an essentially rigid structure and frame work to which the drill assembly 1300 is removable attached and at least one and more particularly two through passages 1205. Each of the through passages 1205 are configured and arranged so as to allow the outer tube member 402 of the drill assembly 1300 to pass there through as drill bit 410 is being is being rotated or pivoted about the pivot point. The frame member 1202 is composed of any one of number of materials known to those skilled in the art that is appropriate for the intended use and the anticipated structural loads that can be imposed during use. In an exemplary embodiment, the frame member 1202 is made from stainless steel such as a stainless steel bar stock.

The first path guard members 1204 are secured to the frame member 1202 using any of a number of techniques known to those skilled in the art so that the through aperture 1205 extends downwardly towards a bottom surface thereof. As indicated above, the though passage 1205 in each of the first path guard members 1204 are arranged so the outer tube member 402 and the drill bit 410 or burr of the drill assembly 1300 are passed there through. In addition, each of the first path guard members 1204 are configured and arranged so as to include a plurality of through passages, one for each of the nail members. Reference shall be made to the foregoing discussion for the nail member through passages 220 of FIG. 1 for further detail and characteristics of these nail member through apertures.

The frame member 1202 also is configured and arranged so as to provide a mechanism for guiding the drill assembly 1300 such that the drill bit 410 thereof follows a predetermined arc or radius of rotation. In illustrative embodiments, the frame member 1202 is configured so as to include a web portion 1210 that extends width wise along the circumferential length of the frame member. In further embodiments, the frame member 1202 is configured and arranged so as to form a step region or a discontinuous radial region 1212 at the ends of the frame member proximal the first guard members 1204 so as to form in effect a radial stop.

The drill assembly 1300 generally forms a curved structure, more particularly a curved tubular structure, that is coupled to the frame member 1202 as herein described and which thus swings around a pivot point or pivot axis that is defined by the frame member 1202. In use, the drill bit 410 rotates about its axis while this axis is held tangent to and swept along an arc of constant radius as defined by the pivot pint. This movement results in or yields a toroidal hole in the bone or bony structure.

The drill assembly includes an outer tube member 402, a key 404, a flexible inner housing 406, a drive cable 408, a drill bit 410 or burr, a barbed fitting 412, a drive adapter 414 and moveable mount member 1310. In further embodiments, the drill assembly includes a distal drive cable bearing 416 and a proximal drive cable bearing 418. As indicated above reference shall be made to FIGS. 1-3 and 6-9 for details and characteristics of the drill assembly 1000 not otherwise shown in FIG. 17 or described hereinafter.

The moveable mount member 1310 includes a frame member mounting portion 1312 and a drill assembly mating portion 1314 that form an integral structure. The frame member mounting portion 1312 is configured and arranged so as to be slidably mounted upon the frame member 1202, more specifically the web portion 1210 thereof. Thus, motion of the frame member mounting portion 1312 along the circumference of the frame member 1202 causes the drill bit 410 to in effect rotate about a fixed point, the pivot point defined by the arcuate portion of the frame member.

As with the mating portion 324 of the pivot arm 302, the drill assembly member mating portion 1314 is configured and arranged so as to receive therein the drill assembly key 404. Reference shall be made to the discussion herein for the pivot arm mating portion 324 and the drill assembly key 404 for further details and characteristics of the drill assembly mating portion 1314.

In further embodiments, the moveable mount member 1310 is configured and arranged so as to include a finger grip 1316 at or proximal an end of the mount member 1310 that is opposite to the end frame member 1302. The finger grip 1316 presents a structural element or feature that is configured to allow the thumb and/or fingers of the user to grasp the finger grip so as to thereby control movement of the moveable mount member 1310, rotation of the drill bit 410 and to also control the drilling pressure (i.e., pressure being exerted by the drill bit 410 on the bone or bony structure while drilling the hole or recess therein. In illustrated embodiments, the finger grip 1316 presents a small tab having bilateral concavities that allow the finger tips to grasp it or a through aperture.

In an alternative embodiment, the frame member 1202 is configured and arranged so as to comprise two sub-members being spaced from each other. The two sub-members further include a slot or other feature in opposing surfaces of the sub-members, which slot or other feature extends in the circumferential direction. In this embodiment, the frame mounting portion 1312 of the movable mount member 1310 is configured and arranged so as to be received in and slide within the slot in each of the opposing surfaces. In this way, the drill bit 410 can be rotated about a fixed point defined by the circumferentially arranged slots in the two sub-members. The foregoing is illustrative of a couple of techniques for configuring the frame member 1302 and the frame member mount portion 1312 so the drill bit 410 can be rotated about a fixed point being defined by the structure of the frame member, however, the foregoing shall not be considered limiting as it is within the scope of the present invention to adapt the drilling apparatus of the present inventions so as to provide a mechanism by which the drill bit can be rotated about a fixed point and/or such that the drill bit follows a fixed path during the drilling process.

Figure 18A:
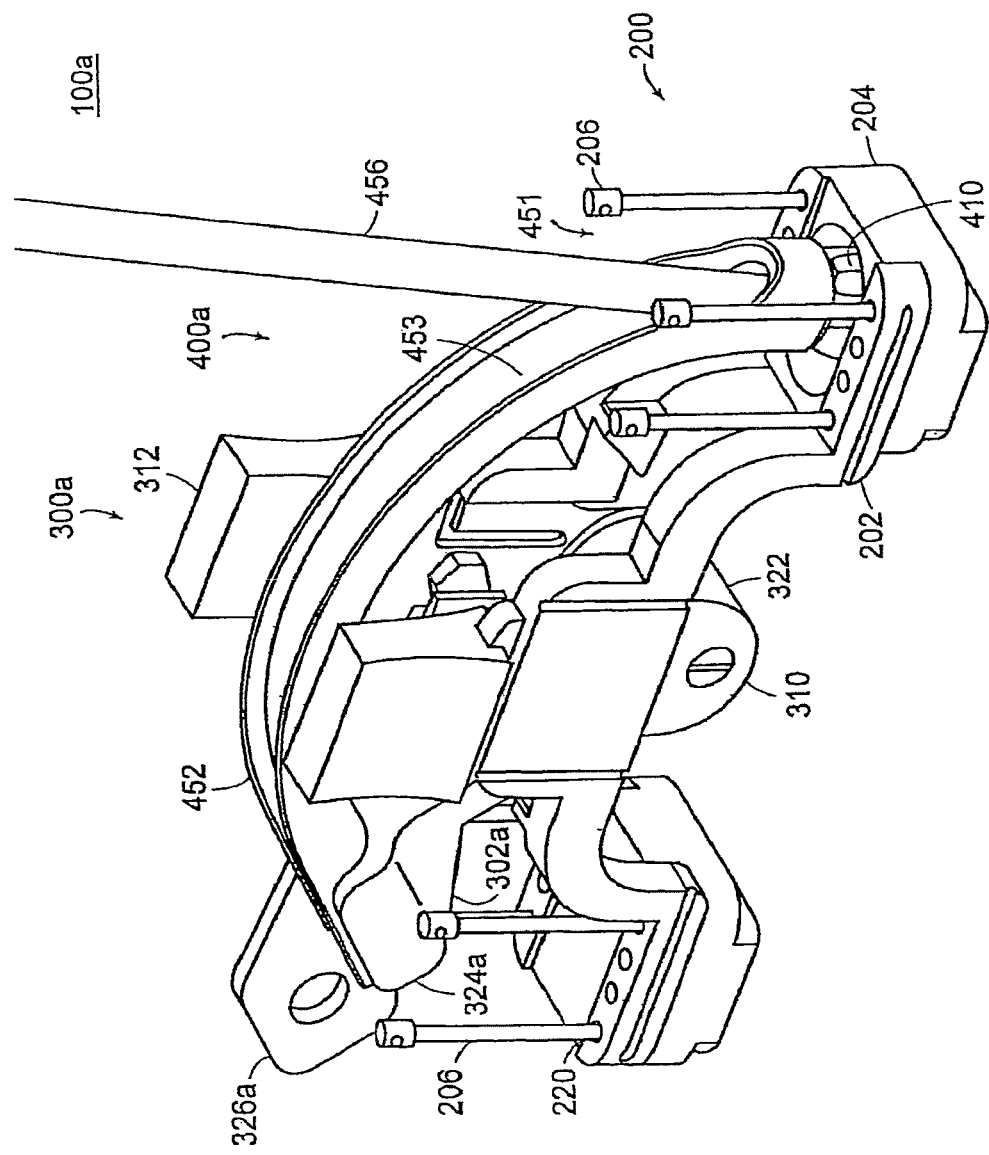
FIG. 18A is a perspective view of drilling apparatus according to yet another aspect of the present invention.
Figure 18B:
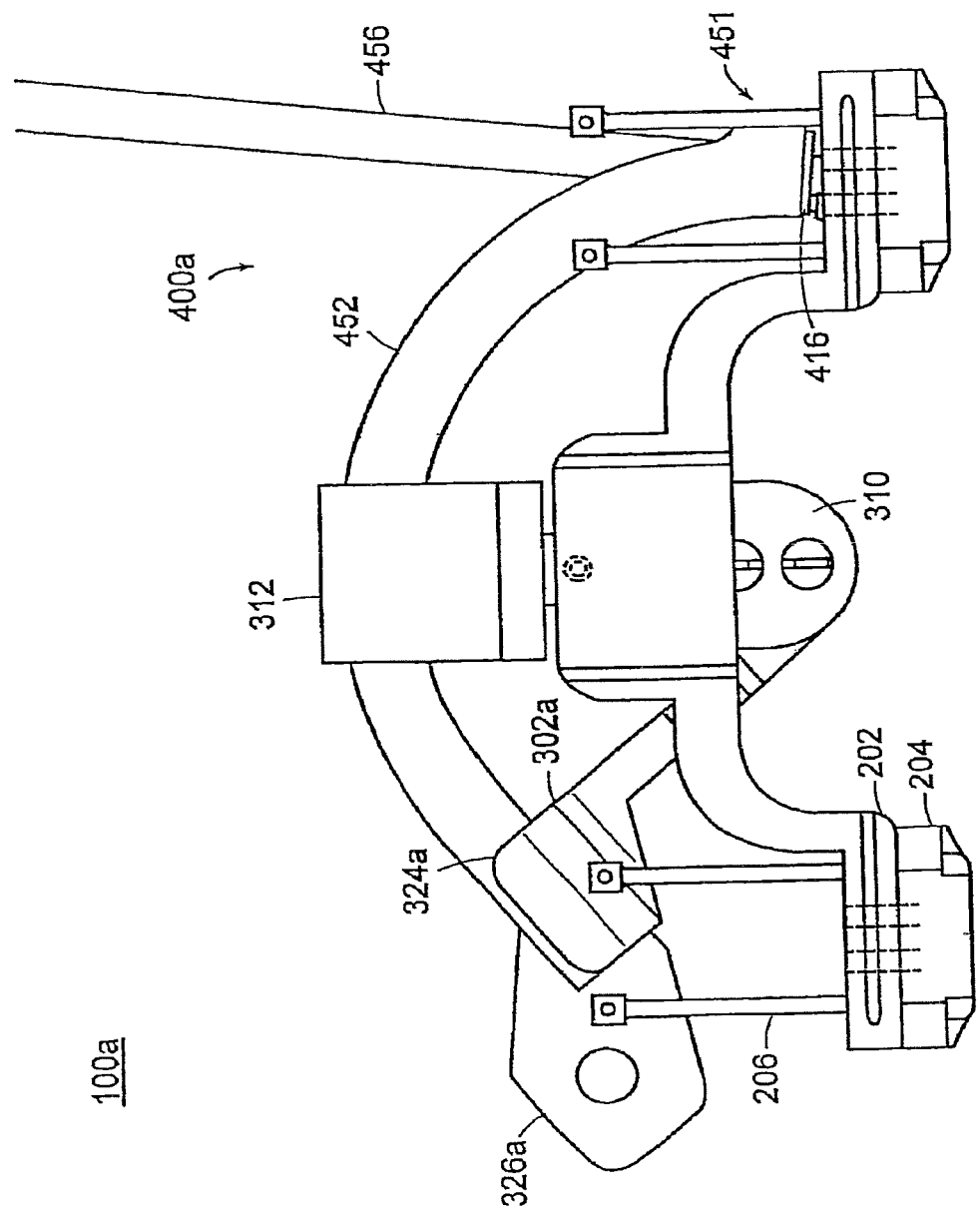
FIG. 18B is side view of the drilling apparatus of FIG. 18A.
Figure 18C:
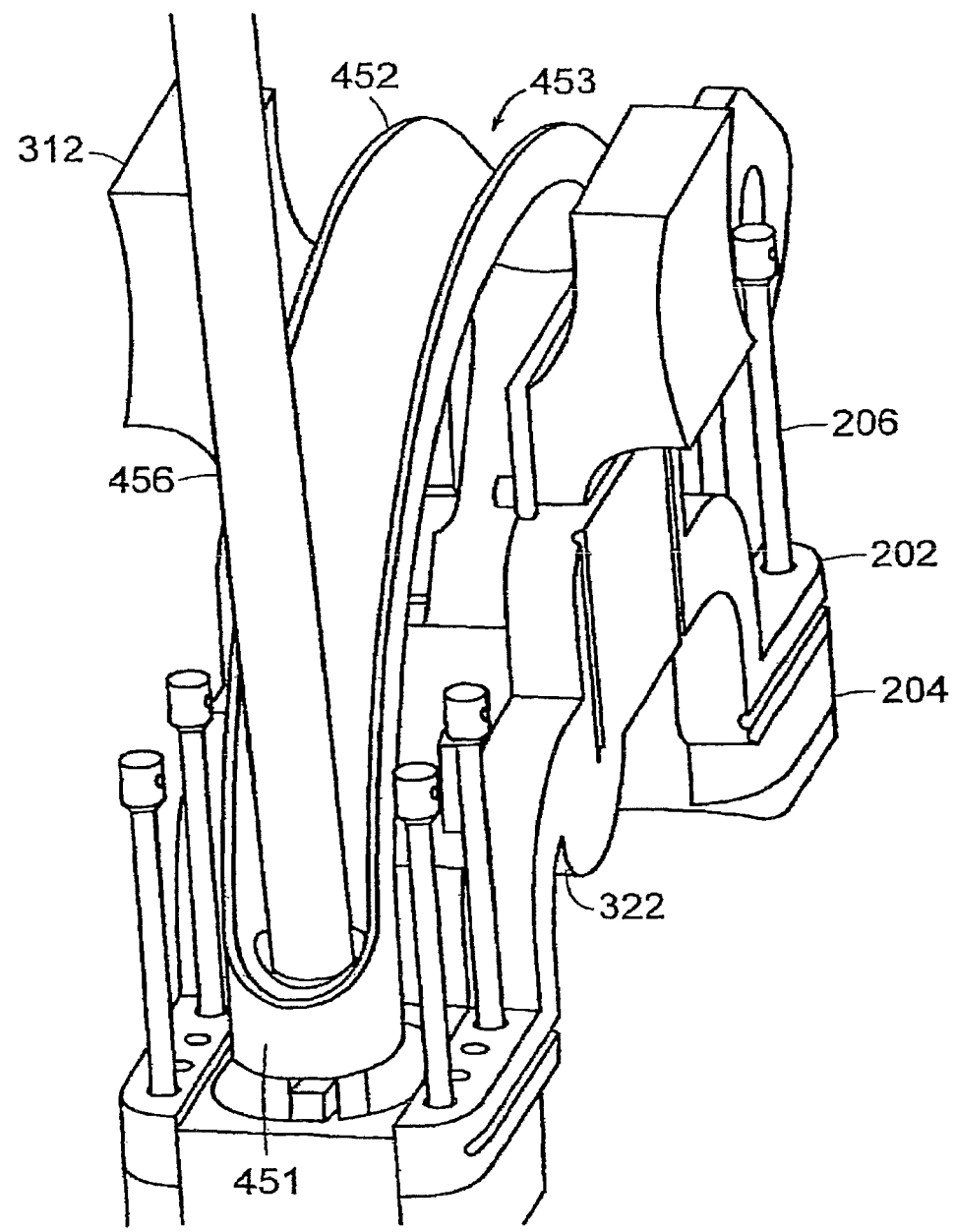
FIG. 18C is another perspective view from a different perspective of the drilling apparatus of FIG. 18A.

Referring now to FIGS. 18A-C there are shown various views of a drilling apparatus 100*a* according to yet another aspect of the present invention that is generally comprised of a platform assembly 200, a pivot arm assembly 300*a* and a drill assembly 400*a*. Reference shall be made to FIGS. 1-9 and the discussion related thereto for features and functions in common with the above-described drilling apparatus 100 shown thereon and not more particularly provided in the following discussion or shown in FIGS. 18A-C. Reference also shall be made to FIGS. 1-9 and the discussion related thereto for details concerning the removably attachment of the pivot arm 300*a* to the platform assembly 200 and the removable securing of the platform assembly 200 to the bone or bony structure.

The pivot arm assembly 302*a* includes a radial arm or pivot arm 302*a*, a pivot pin bracket 304 and a pivot pin 306. The pivot pin bracket 304 includes side plates 310 and finger pads 312 that are secured to the side plates, where the pivot pin extends between the side plates. The pivot pin 306 is received within an aperture 320 in the pivot arm 302*a* such that the pivot arm can rotate about a pivot axis 321. The pivot arm 302*a* is configure and arranged so as to include a mating portion 324*a* that is distal from the end 322 of the pivot arm that is mounted upon the pivot pin. In further embodiments, the pivot arm includes a finger grip 326*a*. Reference shall be made to the foregoing discussion for FIGS. 1-9 for further details of the pivot pin bracket 304, the pivot pin 306, and certain features of the pivot arm 302*a* not described further below. Reference also shall be made to the discussion above for the pivot arm 302 and the finger grip 326 for further details regarding the construction other characteristics for the pivot arm 302*a* and finger grip 326 features not expressly described below or shown in FIGS. 18A-C.

The drill assembly includes a curved or arcuate member 452, a drive cable 456, a drill bit 410 or burr, a drive adapter 414 and a distal drive cable bearing 416. Reference shall be made to the foregoing discussion for FIGS. 1-9 for further details of the drill bit 410, the drive adapter 414 and the distal drive cable bearing 416 not otherwise provided below or shown on FIGS. 18A-C. Reference also shall be made to the discussion above for the drive cable 408 for further details regarding the construction, width and other features not expressly described below.

As indicated herein any one of a number of motors 20 or motor drive assemblies as is known in the art having sufficient power (e.g., torque) and rotational speed are coupled to the drive adapter 414 including but not limited to the Micro100 (Linvatech/Hall Surgical 5053-009) or Blachmax (Anspach Blachmax-KT-0). The drive adapter 414 is a swage-type of fitting that is configured and arranged so it can be swaged upon one end of the drive cable 456. The drive adapter 414 also is configured and arranged so as to provide an input end arrangement that can be mechanically coupled to the output end of a variety of motors or motor drive assemblies or drills including those identified herein.

The pivot arm mating portion 324*a* is secured to a portion of the drill assembly curved or arcuate member 452 using any of a number of techniques known to those skilled in the art that are appropriate for the use and materials used in the construction of these features. In a specific embodiment, the arcuate member 452 is removably secured to the pivot arm-mating portion 324*a* (e.g., mechanical fasteners, adhesives) and in other embodiment the arcuate member is secured to the pivot arm-mating portion (e.g., adhesives, soldering, brazing) so as to form an integral structure. In further embodiments, at least a segment or portion of the pivot arm-mating portion 324*a* is configured and arranged so as to complement the shape of the portion of the arcuate member 452 being received therein. For example and as illustrated in FIGS. 18A-B, the arcuate member 324 also has a curved or arcuate cross-section. Thus, the pivot arm mating portion 324*a* is configured so as to receive therein a curved member having a curved or arcuate cross section. This shall not be considered limiting as the arcuate member 452 can be configured and arranged so as to have any of a number of external cross-sectional shapes.

As indicated above, the arcuate member 452 forms a curved structure that is attached to the pivot arm 302*a* as herein described and which thus swings around the pivot point or pivot axis 321. In use, the drill bit 410 rotates about its axis while this axis is held tangent to and swept along an arc of constant radius as defined by the distance between the mating portion 324*a* of the pivot arm 302*a* and the pivot axis 321. This movement results in or yields a toroidal hole.

The arcuate member 452 is curved to a predetermined radius of curvature so that the centerline thereof is a set distance from the pivot axis 321 of the pivot arm 302*a*. In further embodiments, the arcuate member 452 is a tubular like member having a portion of the tubular structure removed so the arcuate member 452 includes a dished area or depressed region 453 in which is received the drive cable 456 as hereinafter described. In an illustrative embodiment, the dished area or depressed region 453 is generally curved or circular in cross-section as more clearly illustrated in FIG. 18A, C. This, however, shall not be limiting as other geometric shapes are within the scope of the present invention that do not unduly impair the rotational capability of the drive cable 456 when received in the depressed region 453. In further embodiments, the dished area or depressed region 453 of the arcuate member 452 is sized and arranged so as to be capable of removably receiving therein the drive cable 456 and, more particularly so external surfaces of the drive cable are within an envelope or boundary defined by the depressed region 453 of the arcuate member.

The distal end 451 of the arcuate member 452 provides a structure in which the distal distal cable bearing 416 can be secured therein using any of a number of techniques known to those skilled in the art that is appropriate for the materials comprising these elements or features. In exemplary embodiments, the distal cable bearing 416 is secured within the arcuate member distal end 451 by brazing or soldering. Such a structure also provides a fixed point of attachment for the drive cable 456 such that that end of the drive cable and the drill bit 410 moves with the rotation of the arcuate member about the pivot axis 321. In more particular embodiments, the distal drive cable bearing 416 is secured within the arcuate member 452 such that the outer edge of the outer race of the bearing lies in a radial plane from the pivot point, whereby the axis of the drill bit 410 or burr is arranged so as to be tangent to the centerline of the arc of the arcuate member.

When drilling of an aperture or hole in the bone or bony structure is desired, the surgeon or medical personnel applies a force to the finger portion 326a so as to cause the arcuate member 452 to rotate about the pivot axis 321 and so as to cause the distal end 451 of the arcuate member to also rotate about the pivot axis. As the arcuate member distal end 451 rotates through the platform assembly 200, the drive cable 456 also is drawn along with the distal end and also is received in the depressed region 453 of the arcuate member (e.g., as the cable passes below the platform assembly 200). In this way, the rotating drive cable 456 is caused to lie within the depressed region 453 while the drive cable 456 is disposed within the bone or bony structure as the channel or aperture is being formed in the bone or bony structure as hereinafter described.

The arcuate member 452 according to this aspect of the present invention minimizes stress on the drive cable and reduces the amount of access required by the surgeon to perform the surgical procedure. The arrangement, however, also yields an apparatus that advantageously creates a mechanism that allows tissue, muscle, blood vessels (e.g., aorta) and nerves to pass under and around the platform assembly 200 and also to localize the drilling elements of the drill assembly 400a within the structure of the platform assembly. In addition, the pivot arm assembly 300a in combination with the platform assembly 200 provides a mechanism to control the radial movement radius or motion of the drilling elements of the drill assembly 400a from their insertion into the bone or bony structure as well as the retraction from the bone or bony structure such that the drilling elements traverse a specific radius of curvature during such insertion and retraction. In this way, the drilling apparatus 100a according to this aspect of the present invention also controls the maximum depth within the bone or bony structure the drilling elements can attain during use.

Thus, and in contrast to conventional techniques, devices and instrumentalities, the drilling apparatus 100a of the present invention provides a mechanism that protects tissues, blood vessels and nerves from damage while the drilling elements of the drill assembly 400a are being inserted into and withdrawn from the bone or bony structure as well as assuring that the drilling elements will follow a generally fixed path such that the drilling elements do not come into contact with nor damage the tissues, blood vessels and nerves proximal to and surrounding the bone or bony structure while the hole or recess is being formed in the bone or bony structure. Consequently, the drilling apparatus 100a of the present invention minimizes the potential for damage without having to rely solely on the dexterity or skill of the surgeon as is done with conventional techniques and devices.

Figure 11:
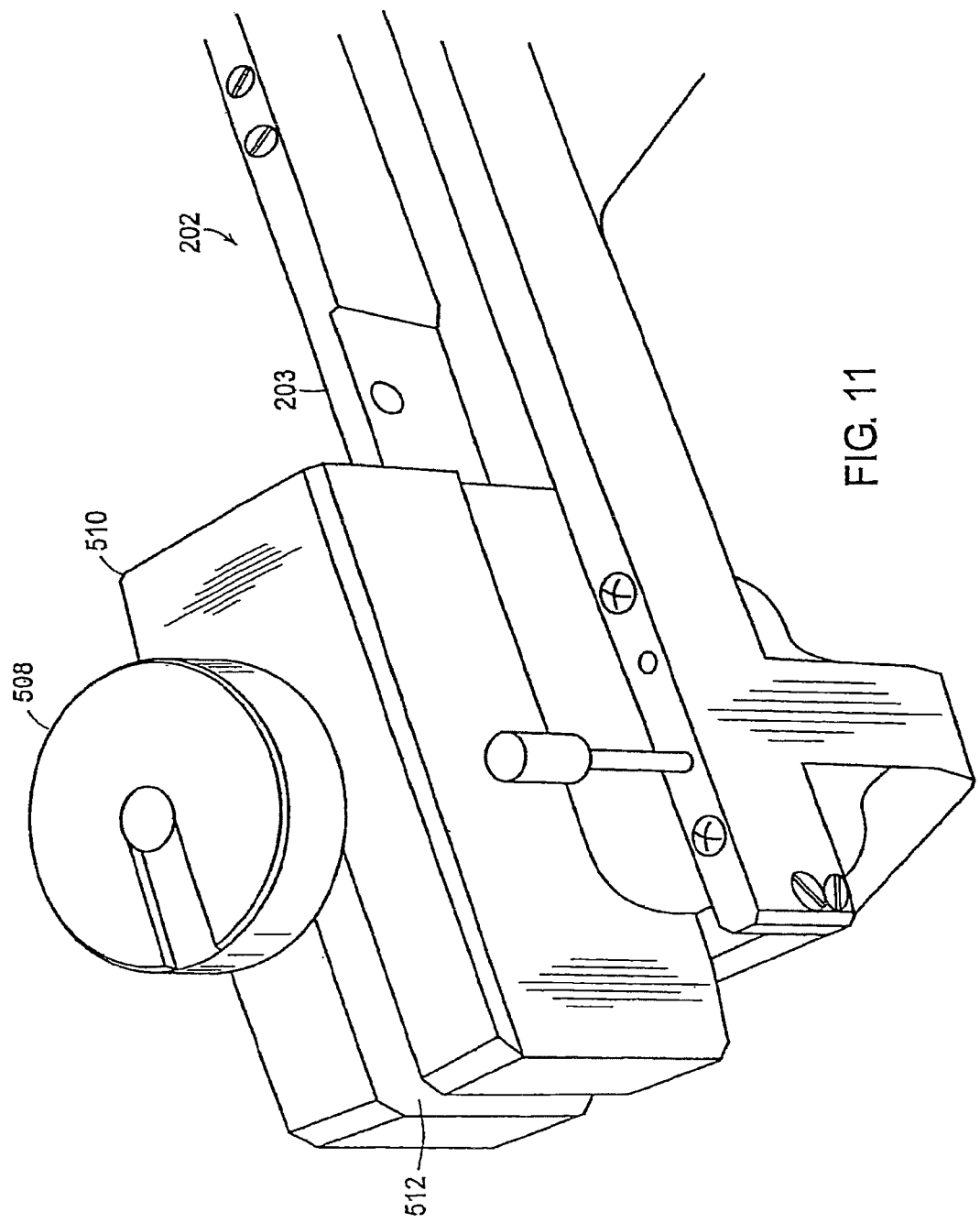
FIG. 11 is a perspective view of the nail removal tool mounted on the platform assembly of the drilling apparatus.

Upon completion of the procedure involving use of the drill assembly 100 of the present invention, and as described herein, the nail members 206 are acted upon so as to remove each of the nail members from the bone or bony structure or spine. This removal can be accomplished using any of a number of techniques or devices known those skilled in the art. In particular embodiments of the present invention, and with reference to FIG. 10A,B, there is shown a side view and an end view respectively of a nail member removal device 500 according to the present invention. Reference also should be made to FIG. 11, which illustrates the removal technique using such a nail member removal device 500.

The nail member removal device 500 includes a block member 502 and a knurled screw member 506. The block member 502 includes a through passage that extends lengthwise in the block member so as to form a saddle structure that can straddle and slide along side rails 203 of the frame 202. In further embodiments, the block member 502 includes a slotted passage 512 that extends from a bottom surface to a top surface of the block member and extends partially lengthwise to a surface of the through aperture 504 or hole that is formed in the block member. The slotted passage 512 also is generally sized so to allow the block member to slide past the head portion 230 that is sticking up above the top surface 210a of the frame, more particularly the side rails thereof.

The threaded aperture 504 or hole is positioned within the block member 502 so that it can be centered over one of the head portions 230 of the nail members 206. In use, the nail members 206 are typically driven into the bone or bony structure such that a bottom surface of the head portion 230 is proud of or above the frame top surface 210a. As such a lower portion of the knurled screw member 506 is machined so as to include a side pocket 514 therein. The side pocket 514 is made in the screw member 506 so as to have sufficient depth (e.g., width) and length to accommodate the head portion coaxially therein. The bottom segment of the screw member 506 also includes a notch that extends generally radially to allow the nail member shaft portion 232 to be received therein and so as to be also coaxial with the screw member.

In particular embodiments, when the screw member 506 is rotated in one direction (e.g., clockwise) the side pocket 514 can be aligned with the slotted through passage 512 and thus be ready to receive therein a nail member head portion 230. The block member 502 is slide along the frame side rail 203 until the head portion is contained within the side pocket 514. After the head portion is disposed in the side pocket, the screw is rotated in the opposite direction (e.g., counterclockwise) thereby causing the screw to rotate in an upwardly direction drawing the notched bottom surface of the side pocket into contact with the bottom surface of the head portion. When the notched bottom surface of the side pocket 514 engages the bottom surface of the head portion, continued rotation of the screw member 506 also causes the head portion to be moved upwardly. In this way, the pointed end of the shaft portion is withdrawn from the bone or bony structure.

In more particular embodiments, the block member 502 and the slotted passage 512 therein are formed such that a portion of the block member is disposed over an end portion of the end rail of the frame 203. This establishes a configuration whereby the pulling load is applied between two support points, thereby minimizing the potential for tipping of the nail member removal device 500 due to unbalanced force couples.

As indicated herein, prior to use of the drilling capabilities of the drilling assembly 100 of the present invention, the nail members are driven into contact with the constricted regions of the first path guards 204 and into engagement with the bone or bony structure or spine. This driving of the nail members can be accomplished using any of a number of techniques or devices known those skilled in the art. In particular embodiments of the present invention, and with reference to FIG. 12 there is shown a side view with a partial cut-away of a nail member drive tool 600 according to the present invention.

The drive tool 600 is a generally cylindrical member having a blind hole 602 or aperture in one end thereof. The blind hole 602 is sized so as to receive therein a head portion 230 of a nail member 206. The drive tool 600 is constructed so that an impact load, such as that imparted by a hammer, at the opposite end 604 thereof drives the nail member 206 disposed in the blind hole 602. In further embodiments, the blind hole 602 also is sized so as to generally prevent the tool from slipping off the head portion. In yet further embodiments, the depth of the blind hole 602 is set so that the bottom surface of the head portion 230 remains a predetermined distance above the frame top surface 210a so as to allow the head portion to be later received in the side pocket of the screw member 506 of the nail member removal device 500.

As indicated herein the drilling apparatus 100 of the present invention is adaptable for use for forming recesses or holes in bones, bony structures or the spine of a mammalian body. The following describes the use of the drilling apparatus in connection with two different techniques (i.e., anterior approach and medial approach) for forming a recess or an aperture in adjacent vertebral bodies of a spine. Although the following discussion specifically refers to the drilling apparatus 100 shown in FIG. 1 it shall be understood that the below described techniques can be used in conjunction with the drilling apparatus 1000, 100a shown in FIGS. 17-18 as well as other embodiments of such apparatuses 100, 100a, 1000. Referring now to FIGS. 13A-L there is shown a series of views illustrating the process for the anterior approach. Reference shall also be made to FIGS. 1-11 and 17-18 and the discussion related thereto for features and functions not provided in the following discussion.

Figure 13A:
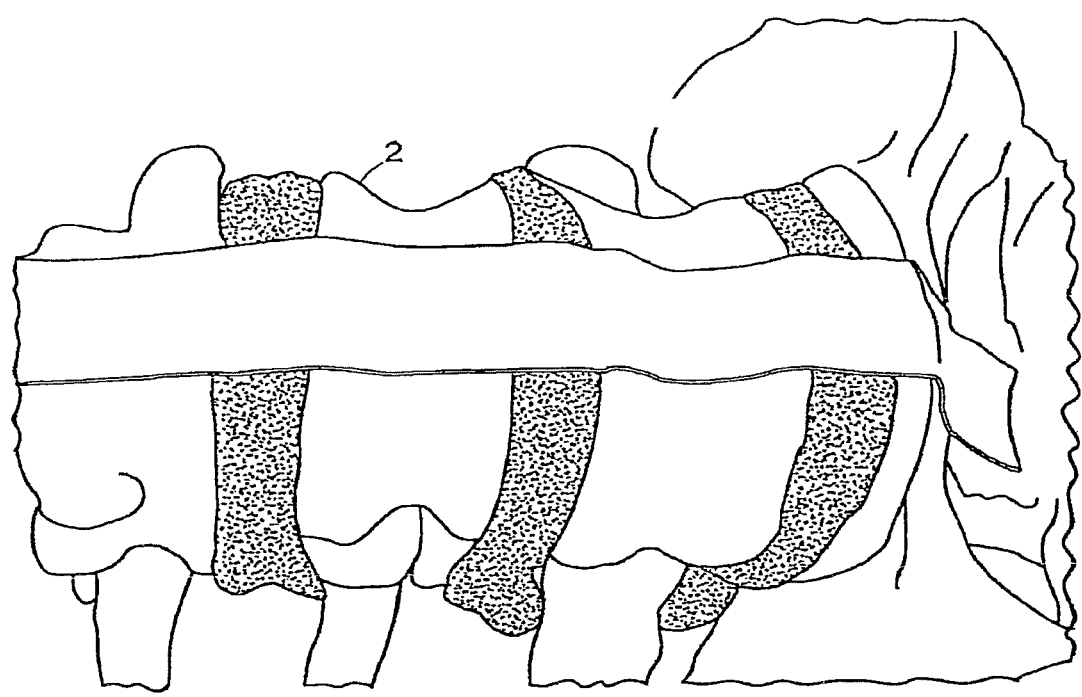
FIGS. 13A-L are illustrations of the process for forming a recess in adjacent vertebral bodies.
Figure 13B:
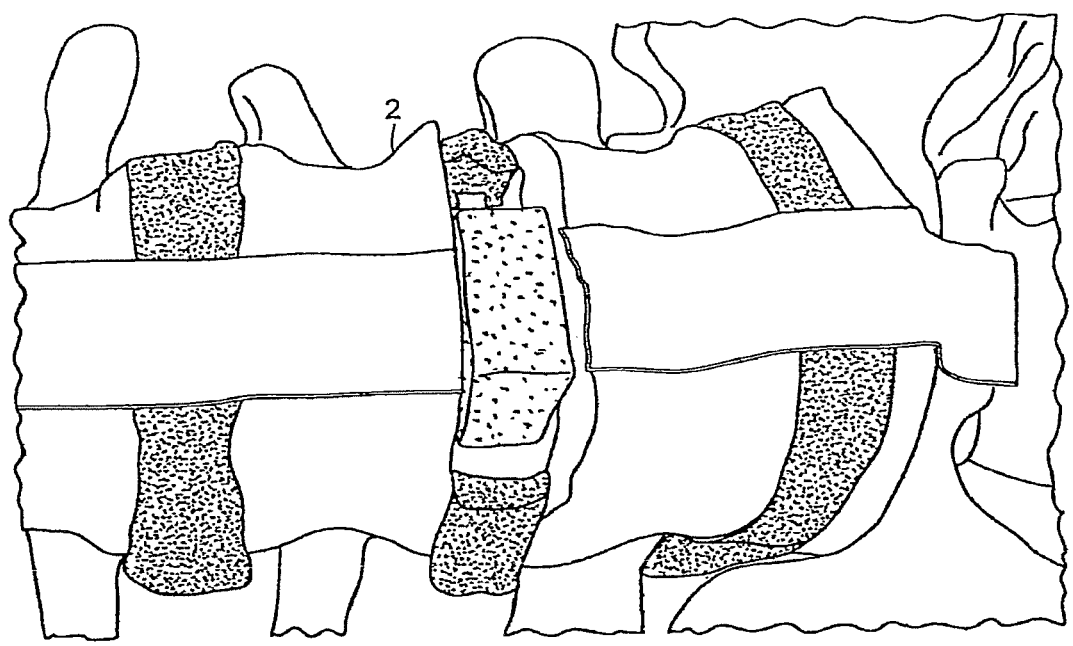
Figure 13C:
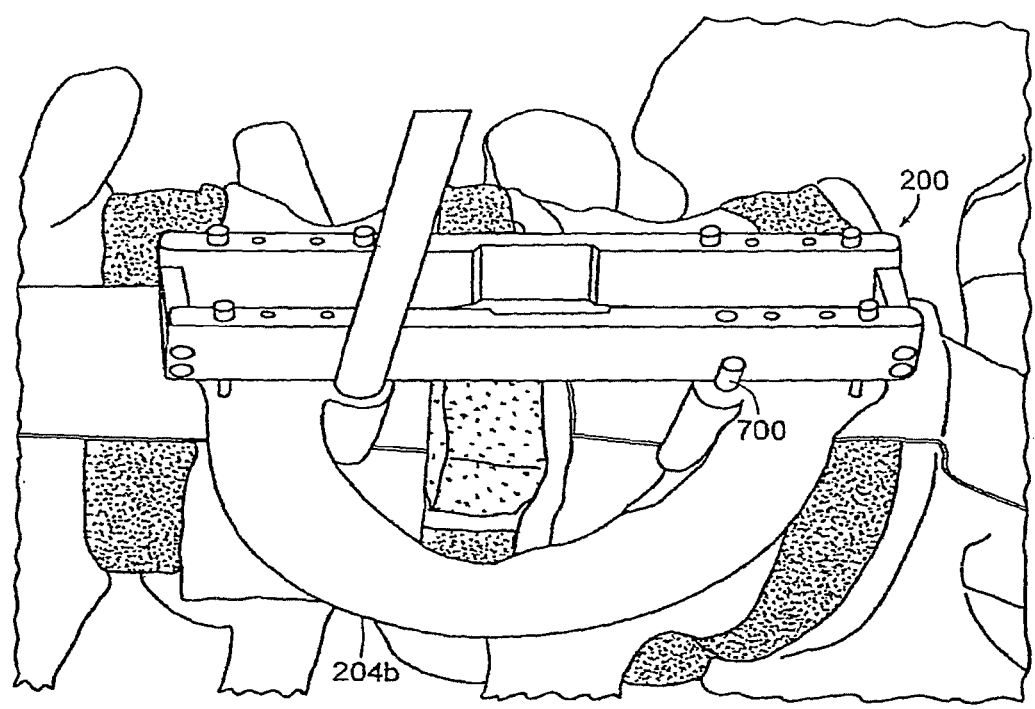
Figure 13D:
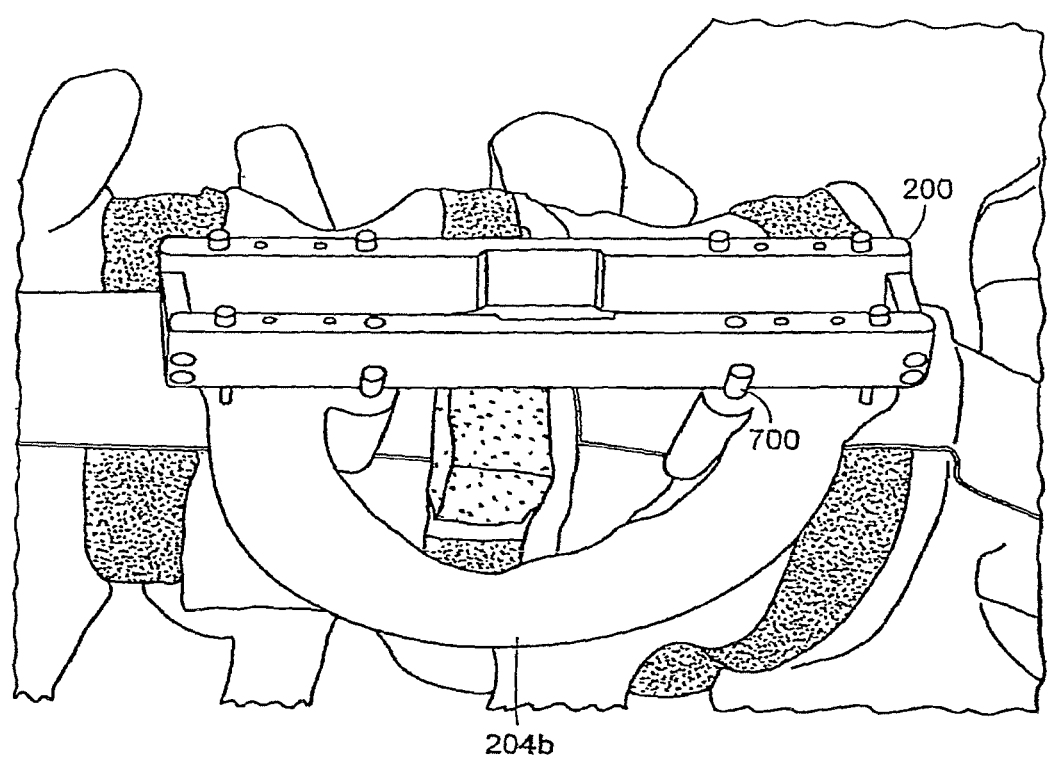
Figure 13E:
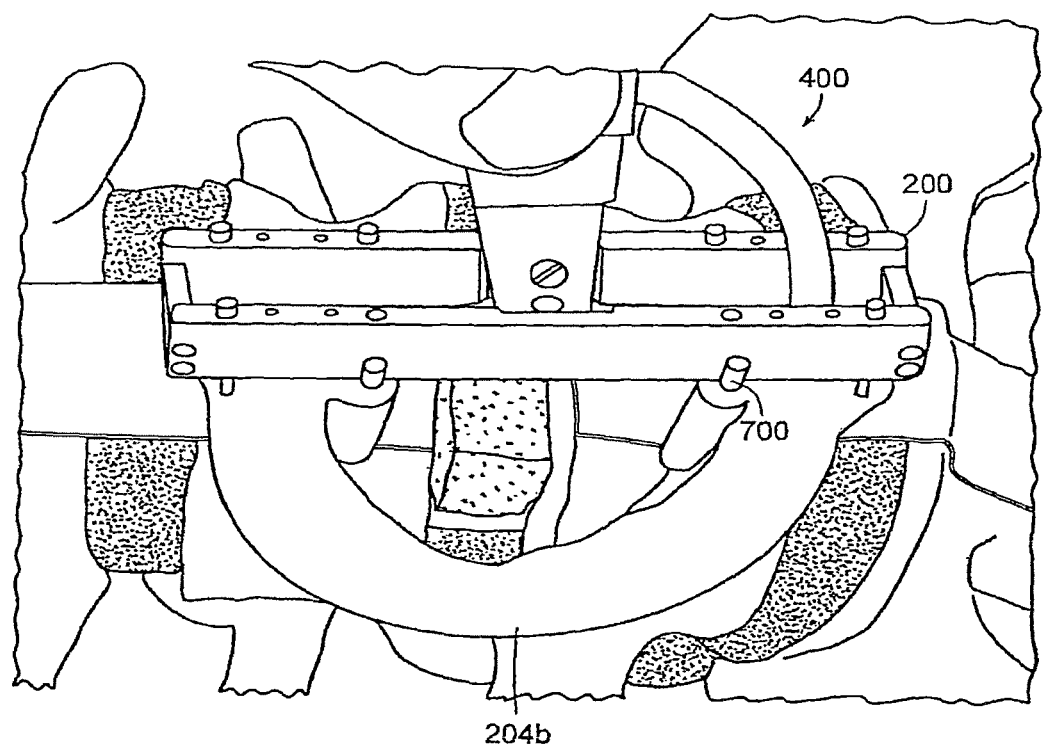
Figure 13F:
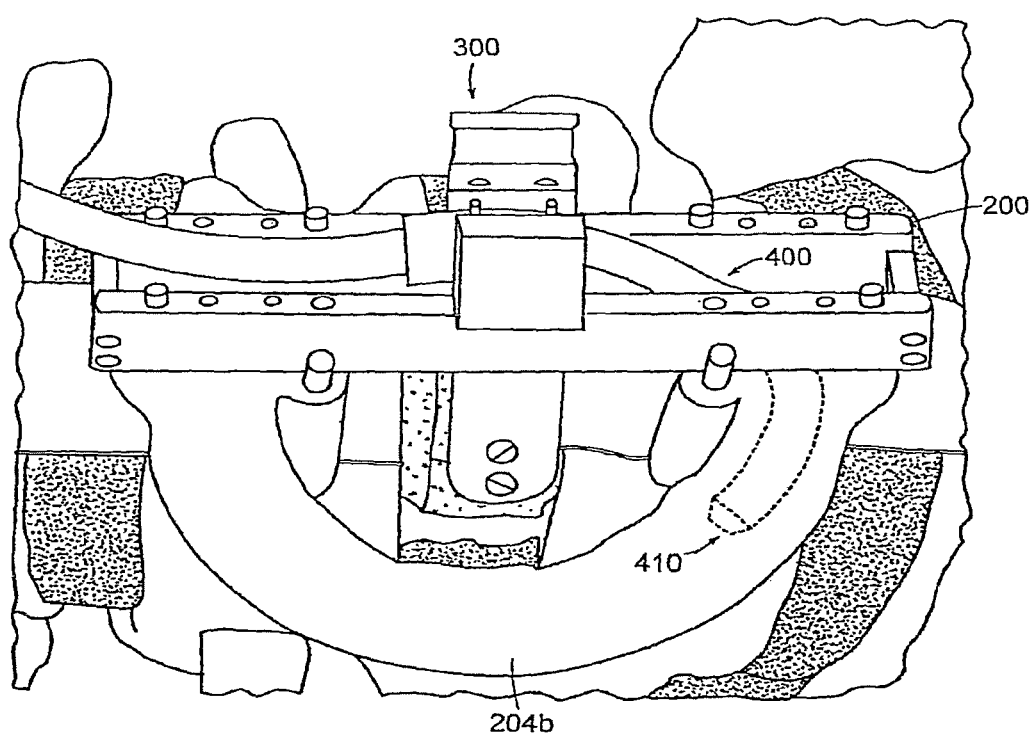

The area of concern is exposed by a surgeon using one of a transperitoneal or retroperitoneal approach, as shown in FIG. 13A and a discetomy is performed at the level to be instrumented and immobilized. After placing a support (e.g., a femoral ring allograft) in the disc space, lateral stabilization is performed (see FIG. 13B).

The drilling apparatus frame 202 is aligned such that it is vertical in an anteroposterior orientation and placed as far lateral as possible on the anterolateral aspect of the vertebrae across the operative level. Temporary placement pins 700 are driven into the vertebral cortex to hold the frame 202 in place while creating the channel or recess. In addition, the present invention contemplates the addition of a second path guard 204b that extends between the first path guards 204. The second path guard 204b is arcuate or curved having a radius that generally corresponds to the path of the drill bit 410. The second path guide 204b also is configured so as to extend outwardly from the vertebral cortex so as to provide a barrier between the drill bit travel path and tissues, nerves and blood vessels proximal the site. The second path guard 204b is constructed of similar materials as the first path guards 204. See FIGS. 13D-E.

When the frame 202 is positioned in the intended fashion, the pivot arm assembly 300 is located and secured within the frame 202, thereby also securing the drill assembly 200 in the frame. See FIG. 13E. The drive motor 20 or drive motor assembly is then secured to the adapter 414. The pivot arm 302 is then positioned so the drill assembly/drill bit is in the starting position so the channel or recess can be cut. See FIG. 13F.

Figure 13G:
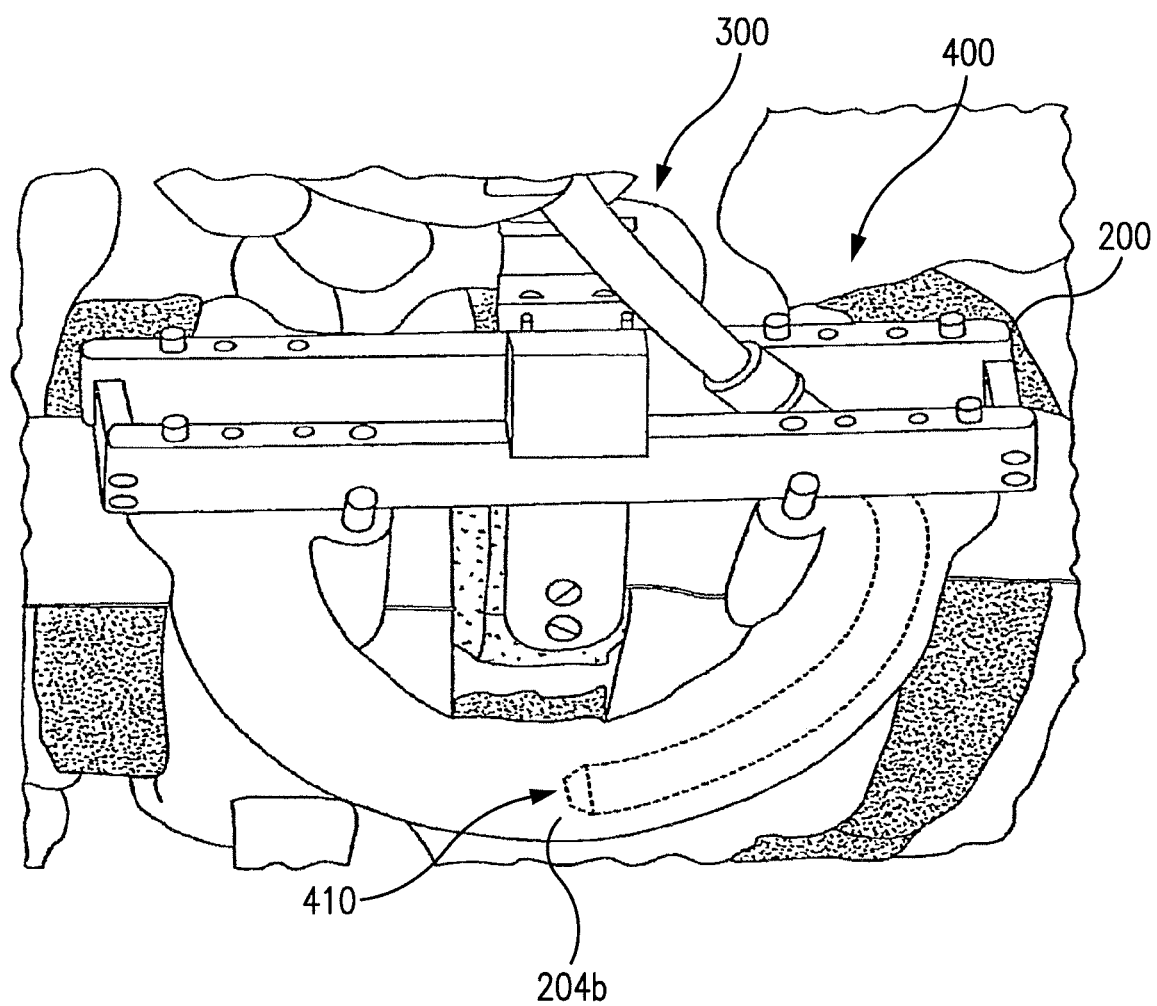
Figure 13H:
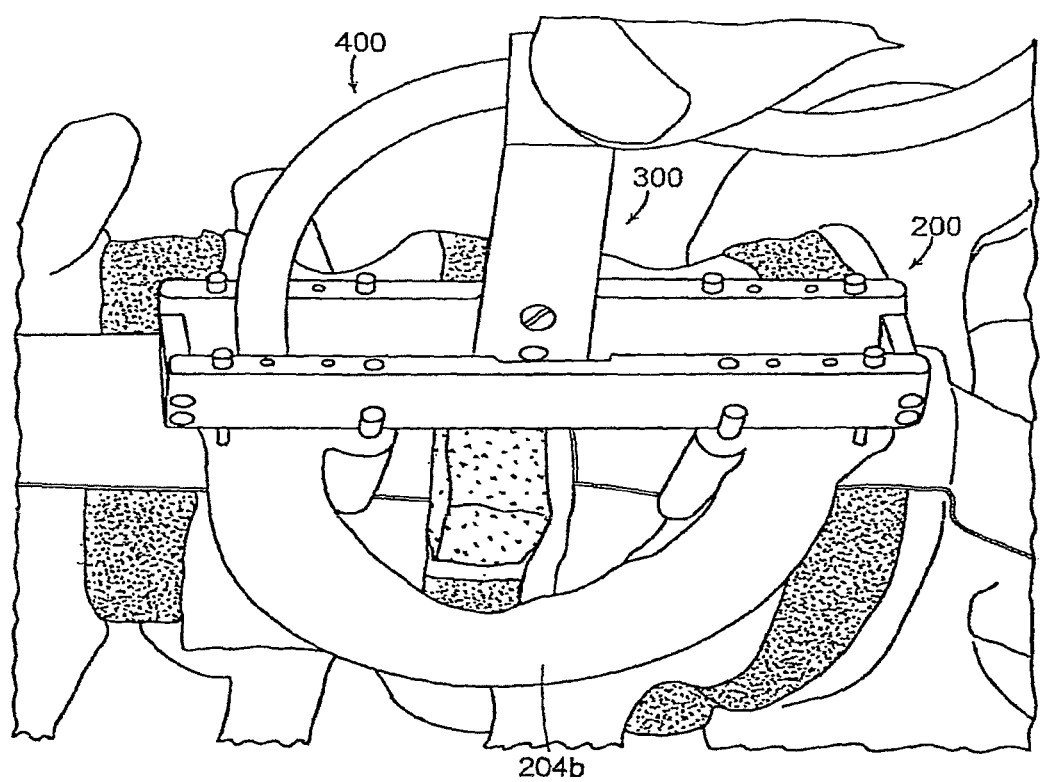
Figure 13I:
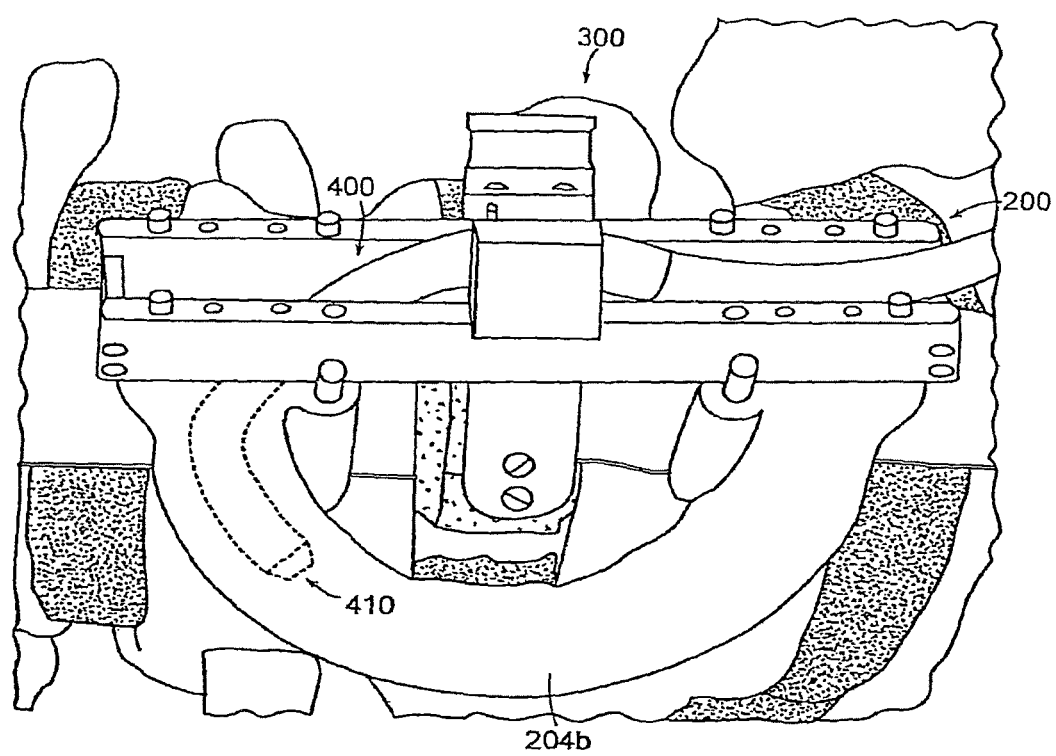
Figure 13J:
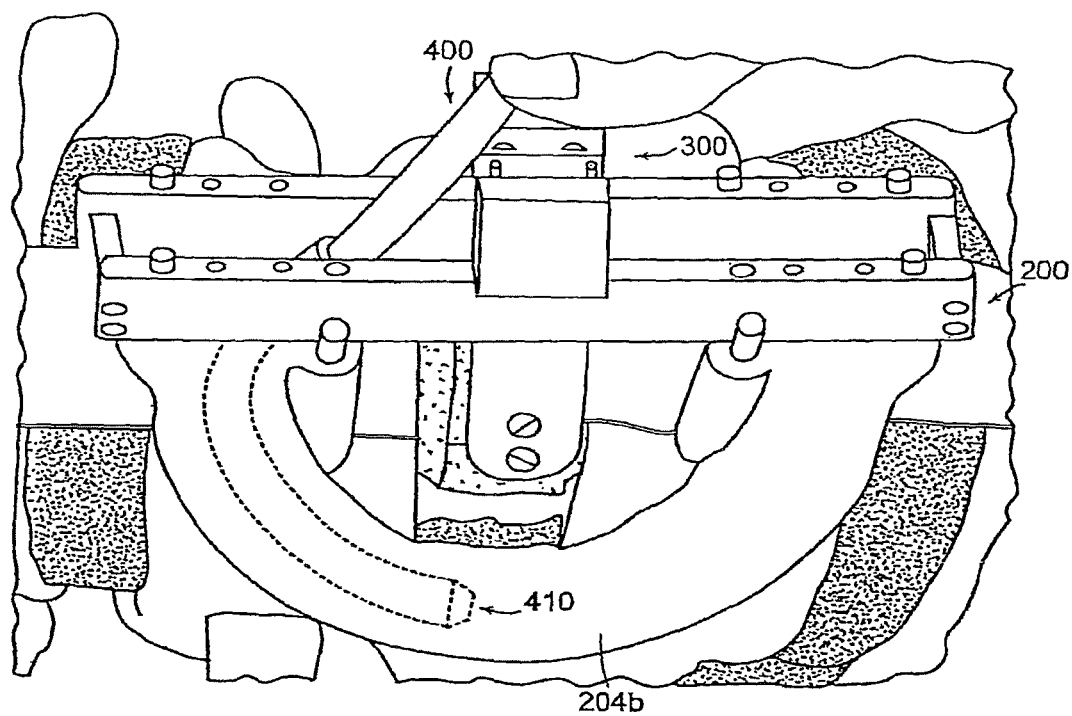
Figure 13K:
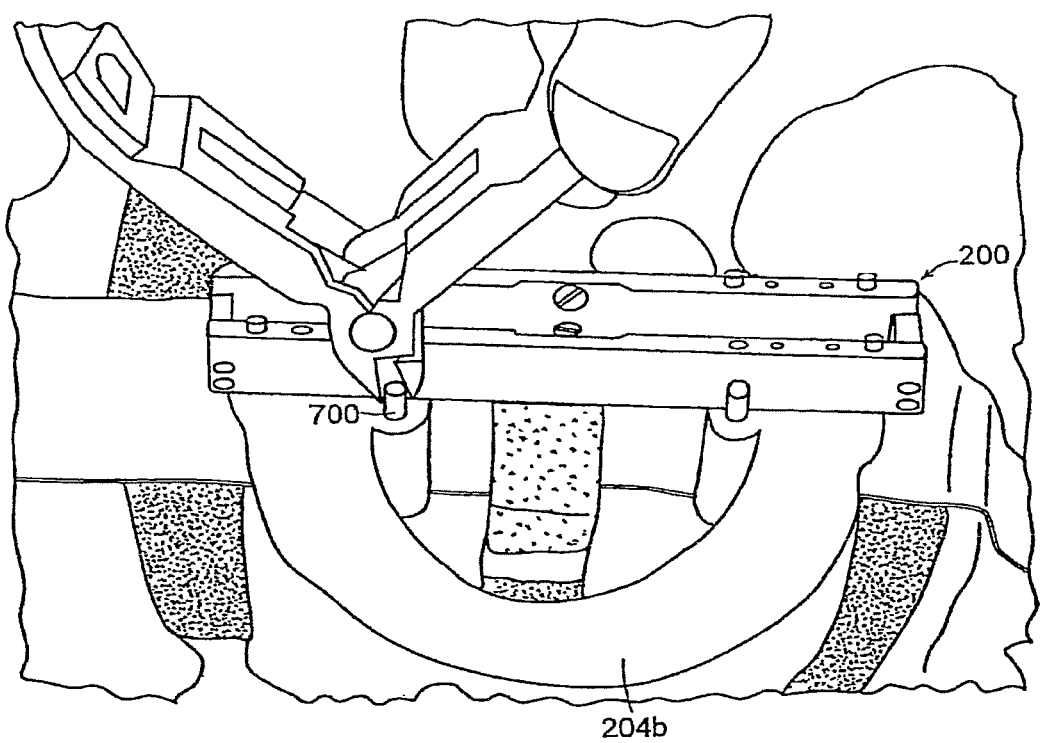
Figure 13L:
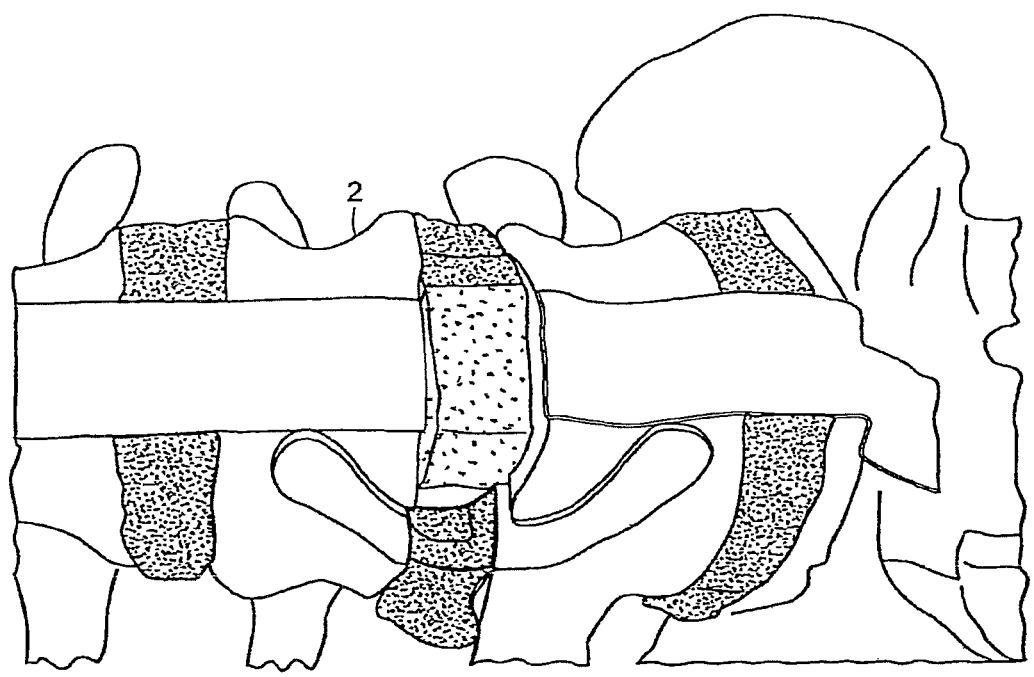

The drill motor 20 is started so as to cause the drill bit 410 to rotate at the desired speed and power, and the pivot arm 302 is rotated about the pivot point thereby causing the drill bit 410 to rotate in a predetermined direction in a downward, circular path as dictated by the frame and the pivot arm. The resulting cut should be made immediately adjacent to the lateral vertebral surface. This cut is complete when the drill bit 410 reaches the disc space as shown in FIG. 13G.

Once the first half of the channel is cut, and with the drive motor 20 turned off and/or disconnected from the adapter 414, the pivot arm is rotated in the opposite direction to return it to the starting position, where the pivot arm assembly 300 can be removed from the frame 202. After removing the pivot arm assembly 300 from the frame 202, the pivot arm assembly is flipped to the opposites side of the frame and reconnected to the frame. In this way, a matching channel can be cut into the other vertebra adjacent to the operative level. See FIG. 13H. As with the first cut, the drive motor 20 is turned on and the pivot arm rotated so the drill bit 410 follows a downward, circular path. After the second half of the channel has been cut, the pivot arm is returned to the starting position and the pivot arm assembly 300 is removed from the frame 202. See FIGS. 13I-J.

The temporary placement pins 700 are removed from the vertebral bodies and the frame 202 is removed from the operative site (see FIG. 13K) and a standard osteotome chisel can be used to remove any remaining bone from the channel edges so that the channel is open to receive or accept the curved rod.

Now with reference with FIGS. 14A-D there is shown the process for placing, positioning and attaching or implanting a curved rod 800, including those described in any of U.S. Pat. Nos. 6,607,530 and 6,923,811, the teachings of which are incorporated herein by reference. The curved rod 800 is positioned in the channel and secured to the vertebral bodies using interlocking screws 802, 804 that traverse the rod and penetrate the vertebra at an angle that will avoid sensitive neurologic structures. The screws hold the curved rod 800 in place and stabilize the motion segment to facilitate healing of the bone within the disc space.

Figure 14A:
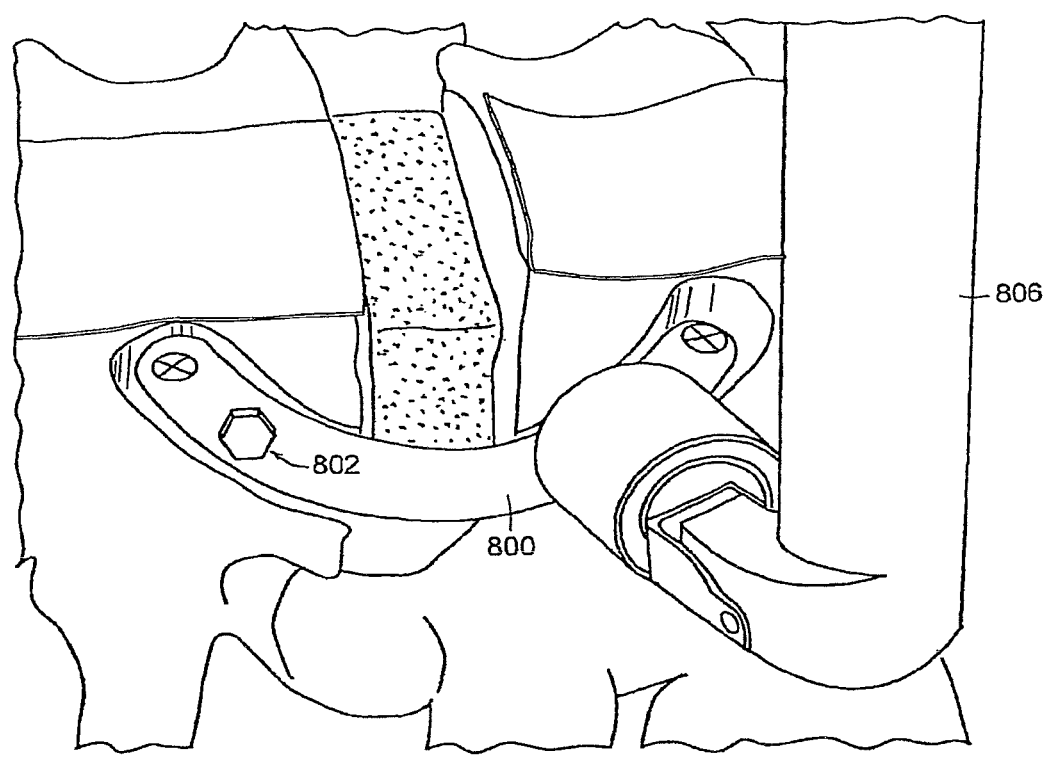
FIGS. 14A-D are illustrations of the process for implanting or attaching a curved rod across the adjacent vertebrae.
Figure 14B:
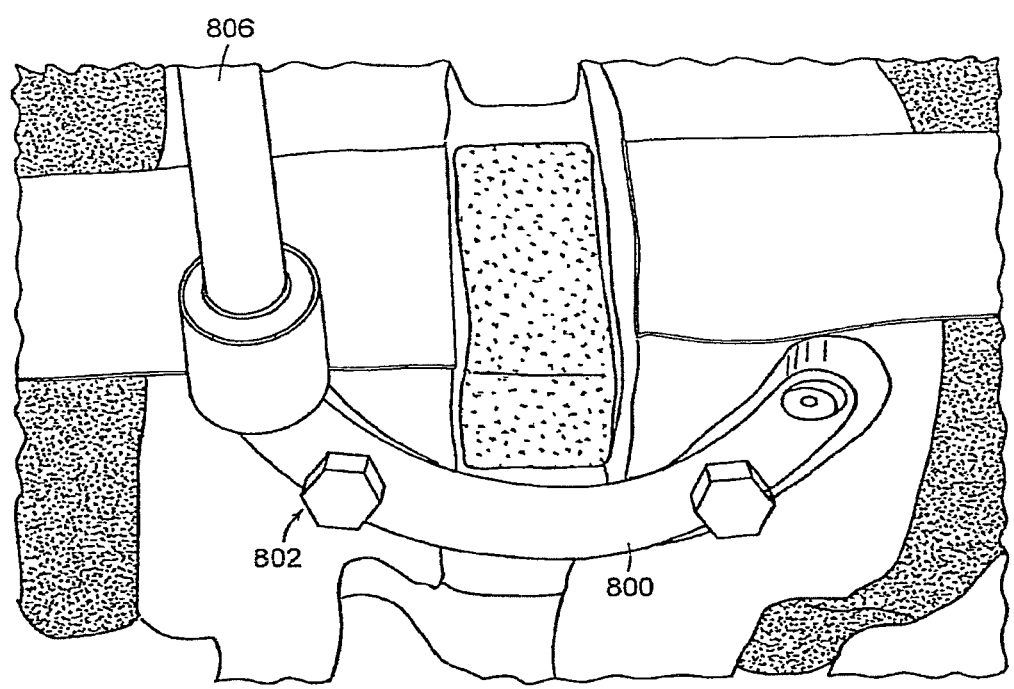
Figure 14C:
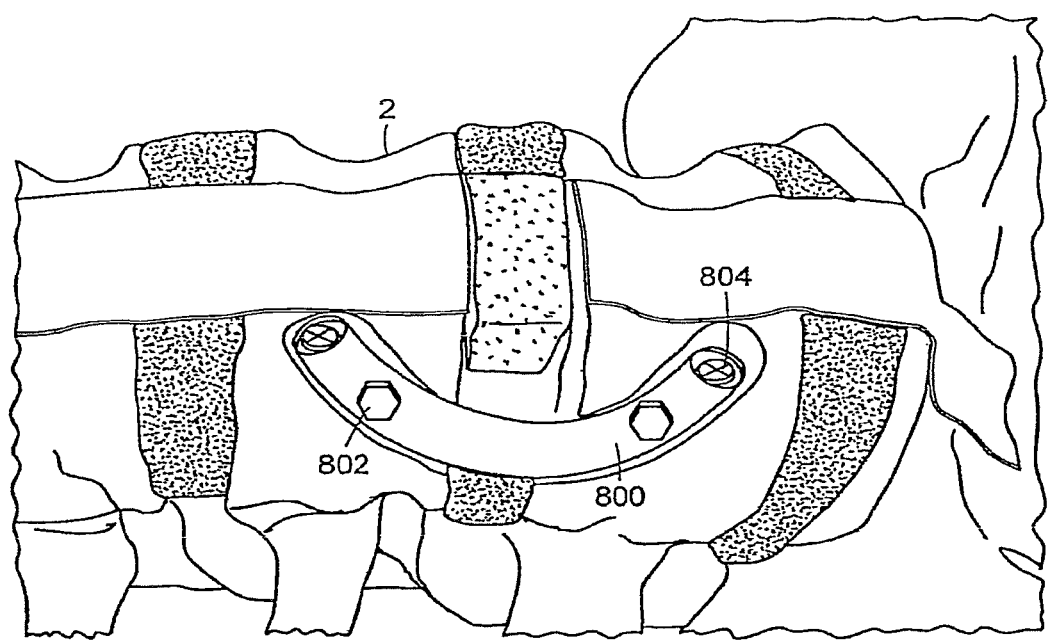
Figure 14D:
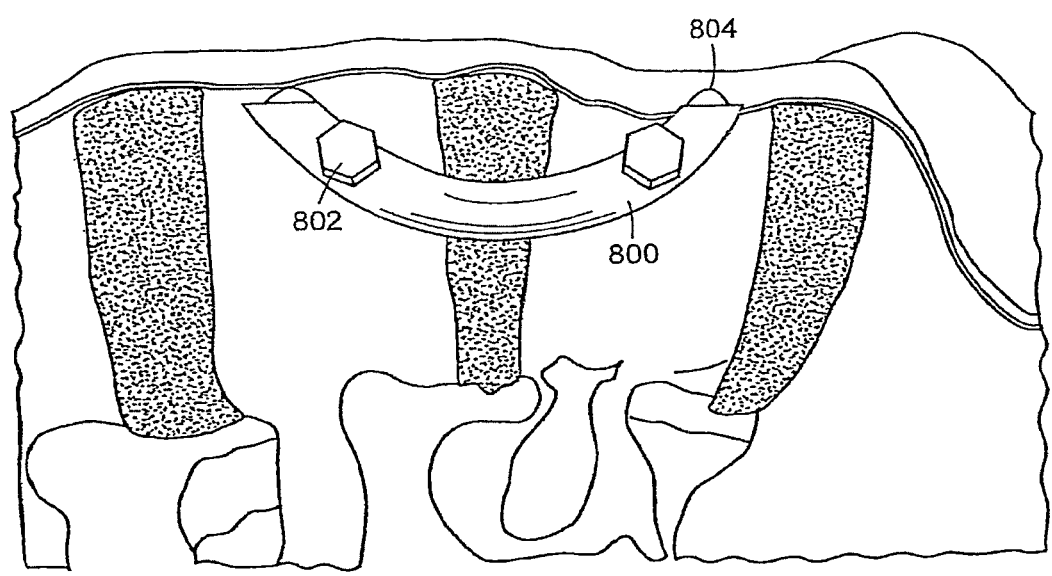

Two lateral screws 802 pass through the lateral holes of the curved rod and set on the lateral surface of the implant. The two end screws 804 are passed through the open ends of the curved rod and each is inserted until the screw head is contained within the hollow of the implant. The lateral and end screws are inserted using for example a Cardan screwdriver 806. As shown in FIGS. 14C-D the curved rod is now securely in place in either of the recess (FIG. 14C) or a surface-mounted configuration (FIG. 14D).

Referring now to FIGS. 15A-H there is shown a series of views illustrating the process for the medial approach. Reference shall also be made to FIGS. 1-11 and 17-18 and the discussion related thereto as well as for FIGS. 13-14 for features and functions not provided in the following discussion. As above, the area of concern is exposed by a surgeon using the appropriate technique and the drilling apparatus frame 202 is aligned such that it is vertical in an anteroposterior orientation and placed as far midline as possible on the anterior aspect of the vertebrae across the operative level. The pointed ends of the nail members 206 are then driven through the platform frame 202 and the first path guards 204 so as to be driven into the vertegral cortex to hold the frame in place while cutting the channel or through aperture. See FIG. 15A-B.

The pivot arm assembly 300 is then secured to the frame 202 and thereby also securing the drill assembly to the frame. The drive motor 20 also is coupled to the drill assembly 300 via the adapter 414 See FIG. 15C. The pivot arm 302 is then rotated until the drill bit 410 and the pivot arm are in the start position, whereat the drill motor 20 is started. See FIG. 15D. The pivot arm is rotated so as to cause the drill bit to travel in a downward circular path thereby making cuts in the vertebral body. In the case where, the first cut does not cut a complete channel or through aperture, the pivot arm assembly is detached from the frame, flipped, reconnected to the frame and the cutting process described above is repeated until the rest of the channel or through aperture has been cut. See FIGS. 15D-F.

Figure 15A:
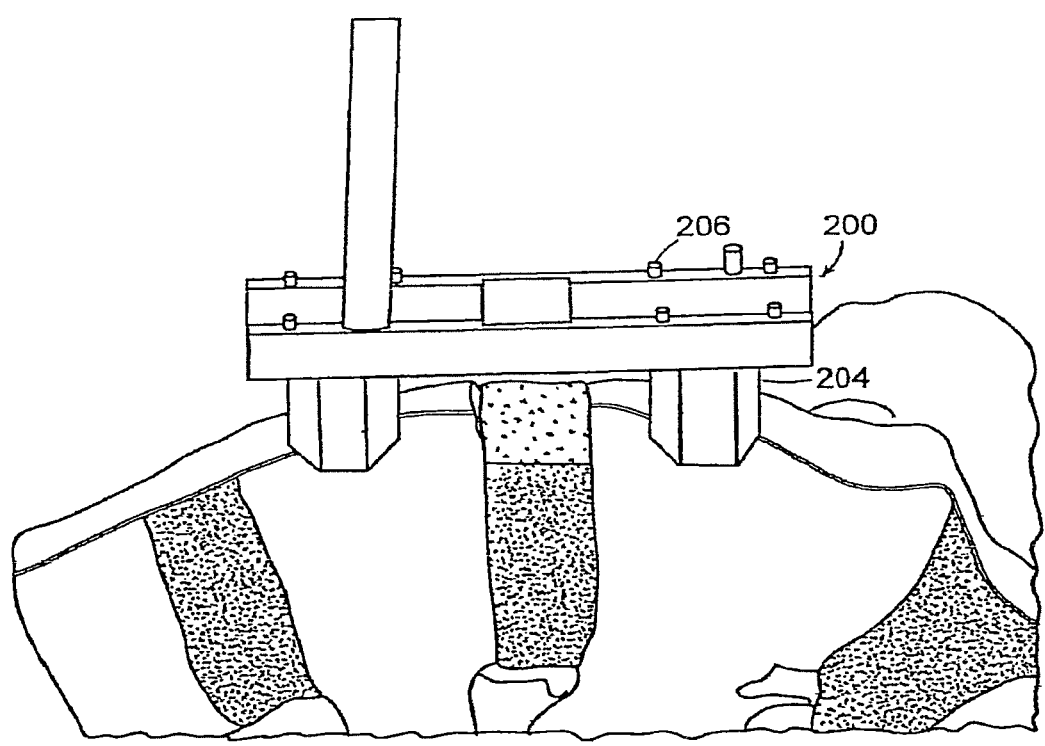
FIGS. 15A-H are illustrations of the process for forming a through aperture in adjacent vertebral bodies.
Figure 15B:
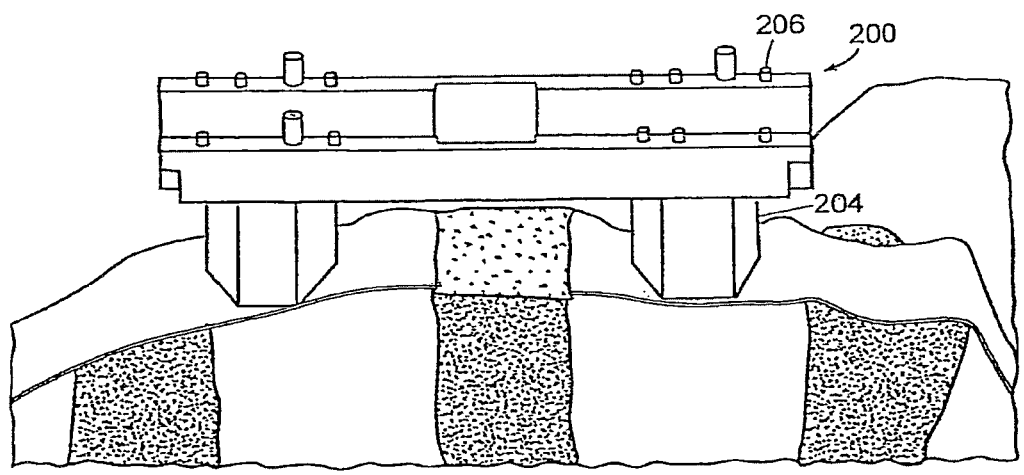
Figure 15C:
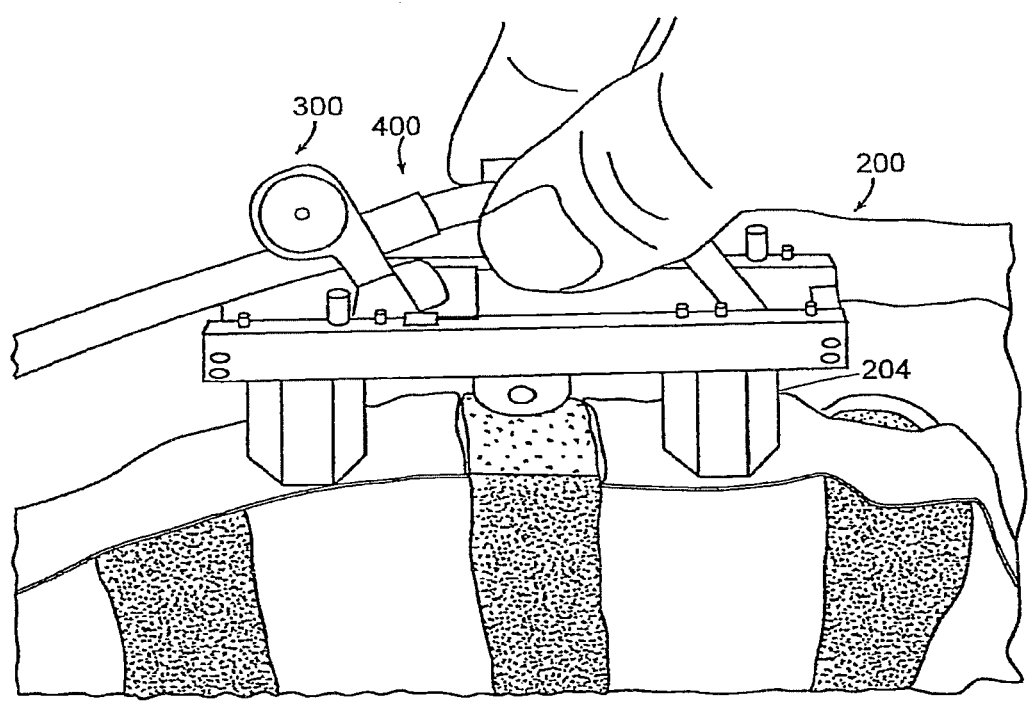
Figure 15D:
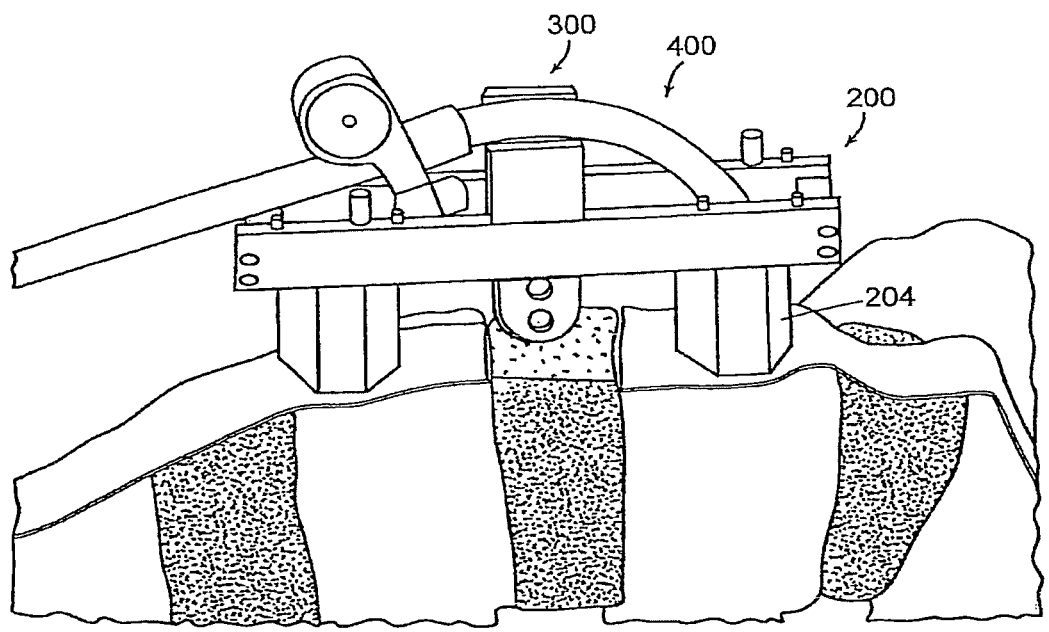
Figure 15E:
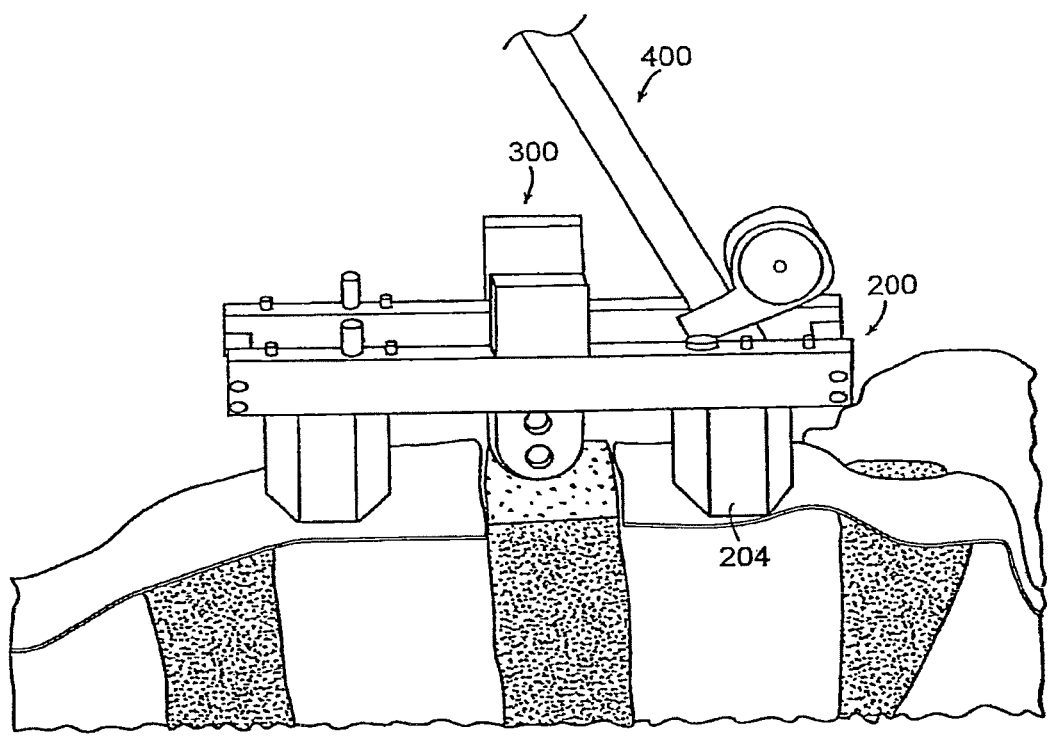
Figure 15F:
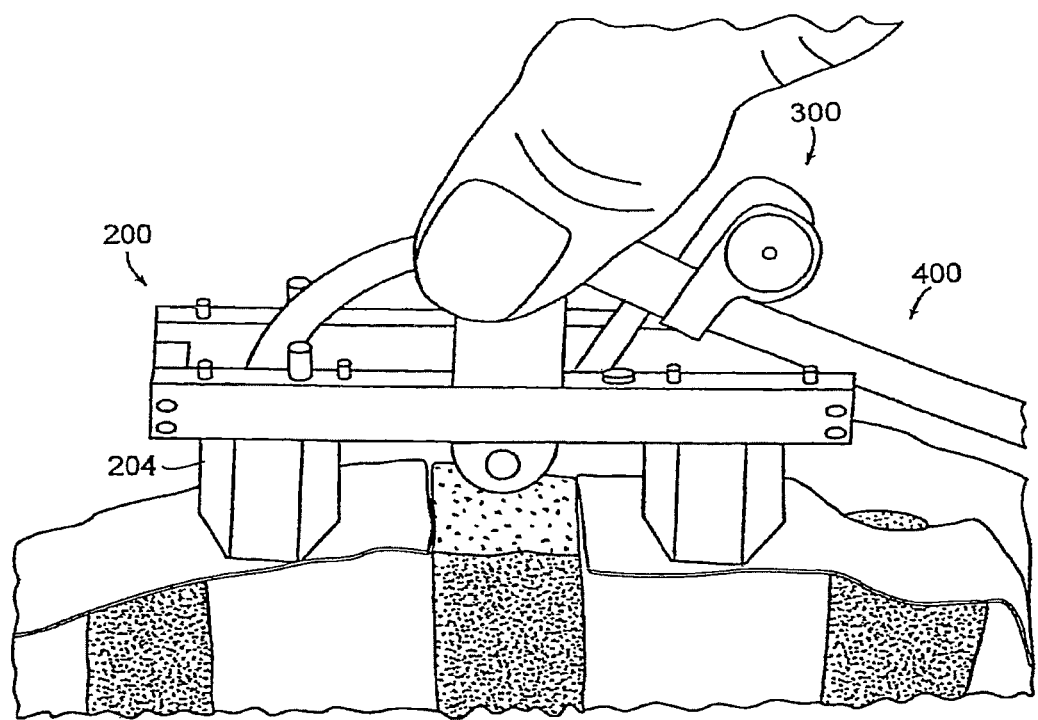
Figure 15G:
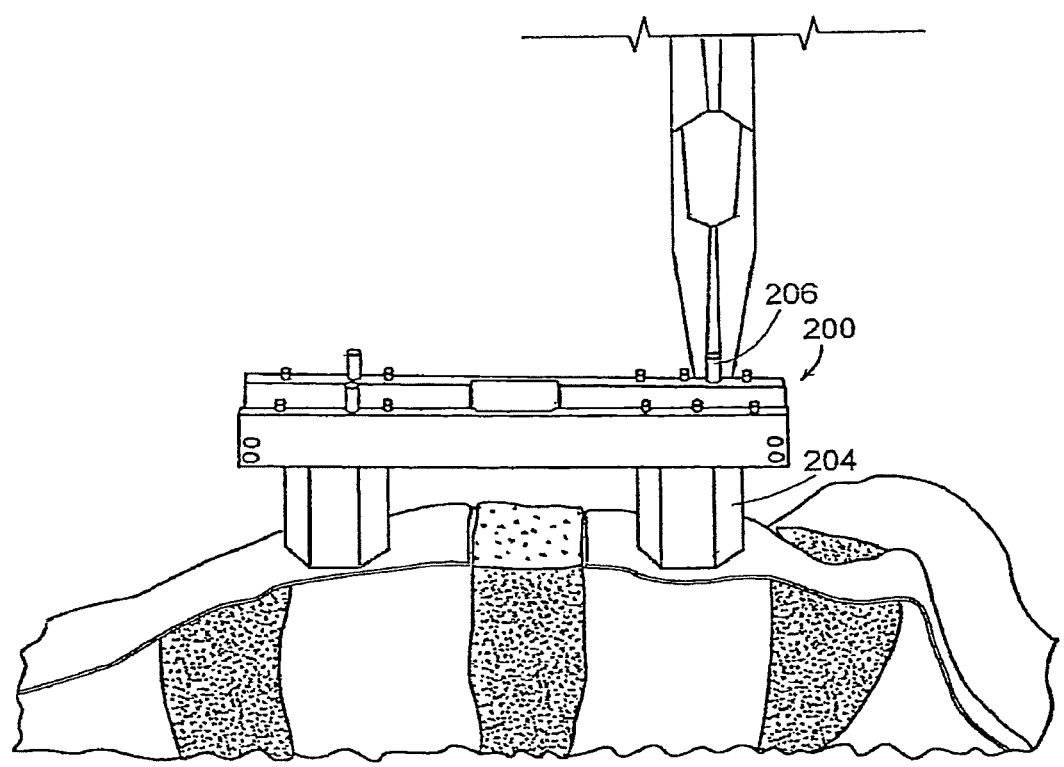
Figure 15H:
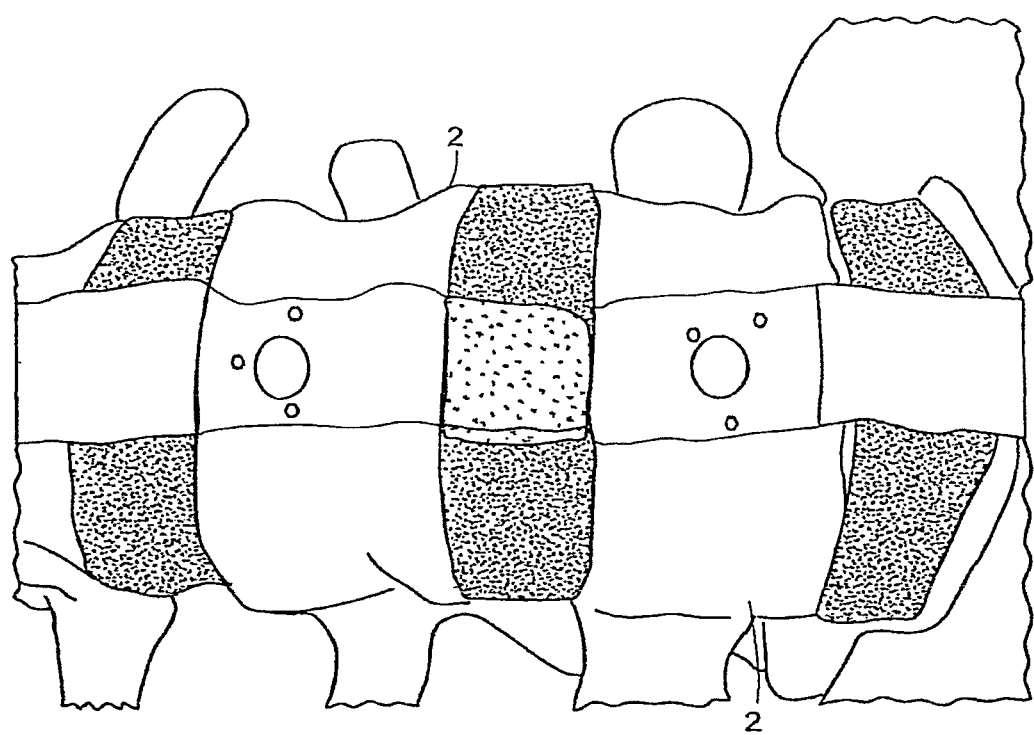
Figure 15I:
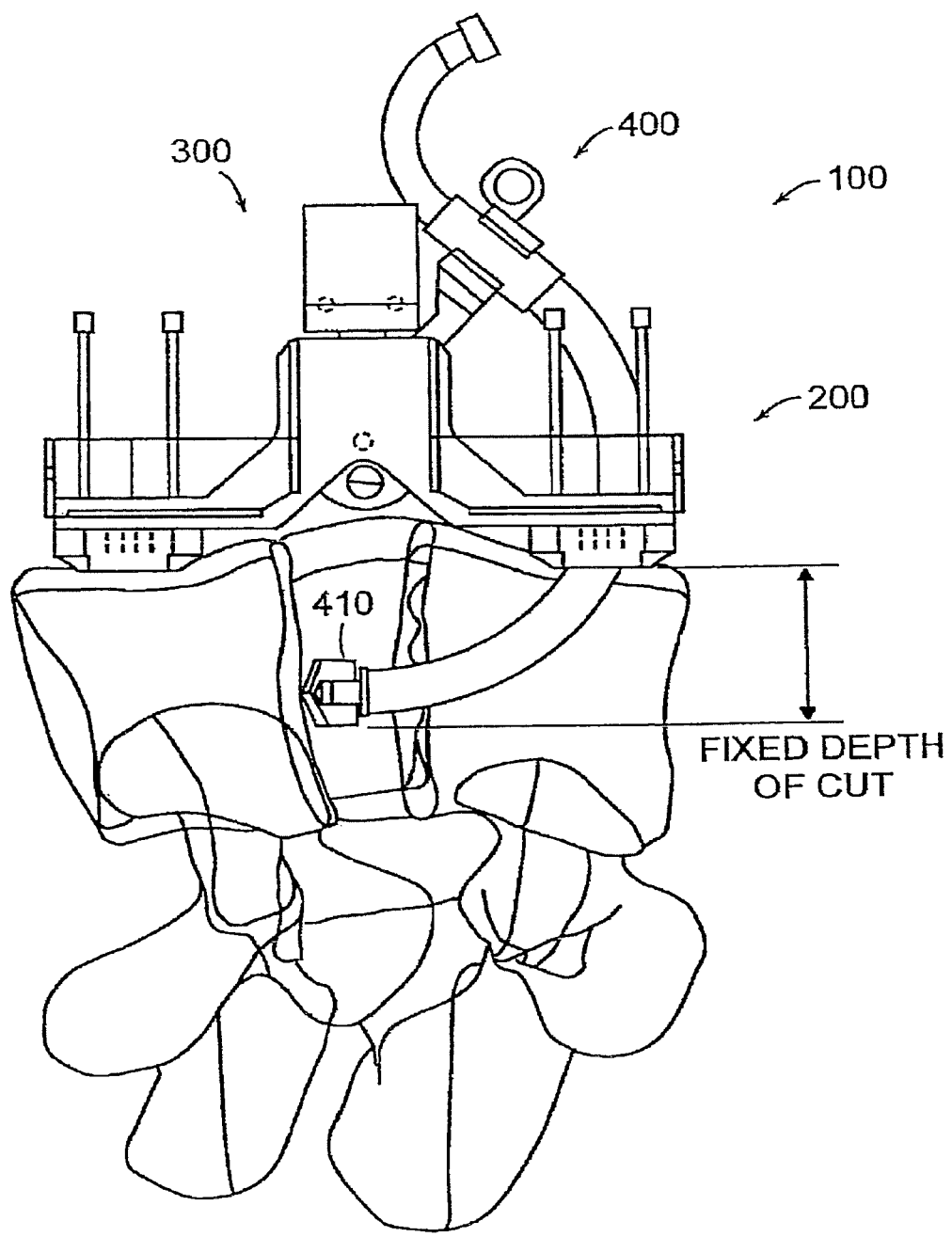
FIG. 15I is an illustrative view of adjacent vertebral bodies illustrating the fixed cutting depth aspect yielded by the drilling apparatus of the present invention.

There is shown in FIG. 15I, a illustrative view of adjacent vertebral bodies with the drilling apparatus 100 of the present invention mounted thereon. As illustrated, the arrangement of the drilling apparatus 100 of the present invention is such that the drilling bit follows a fixed path established by the configuration of the drilling apparatus 100. In this way, a maximum or fixed cutting depth also is set or established by the configuration of the drilling apparatus 100.

After the complete channel or through aperture is cut in the adjacent vertebral bodies, the pivot arm assembly 300 and the drill assembly 400 are detached from the frame 202 and the nail members 206 are removed from the vertebral bodies and the frame or platform assembly 200 is removed from the operative site. As indicated herein, removal of the nail members 206 can be accomplished using the nail member removal device 500 of the present invention. The above process yields a channel opening or through aperture in both vertebral bodies that can accept the curved rod 800. See FIGS. 15G-H.

It should be recognized that it is within the scope of the present invention to cut a channel through or partially through one of the vertebral bodies. Thus, the foregoing process is adaptable for accomplishing this by limiting rotational movement such that a channel is not cut completely through one of the vertebral bodies.

Figure 16A:
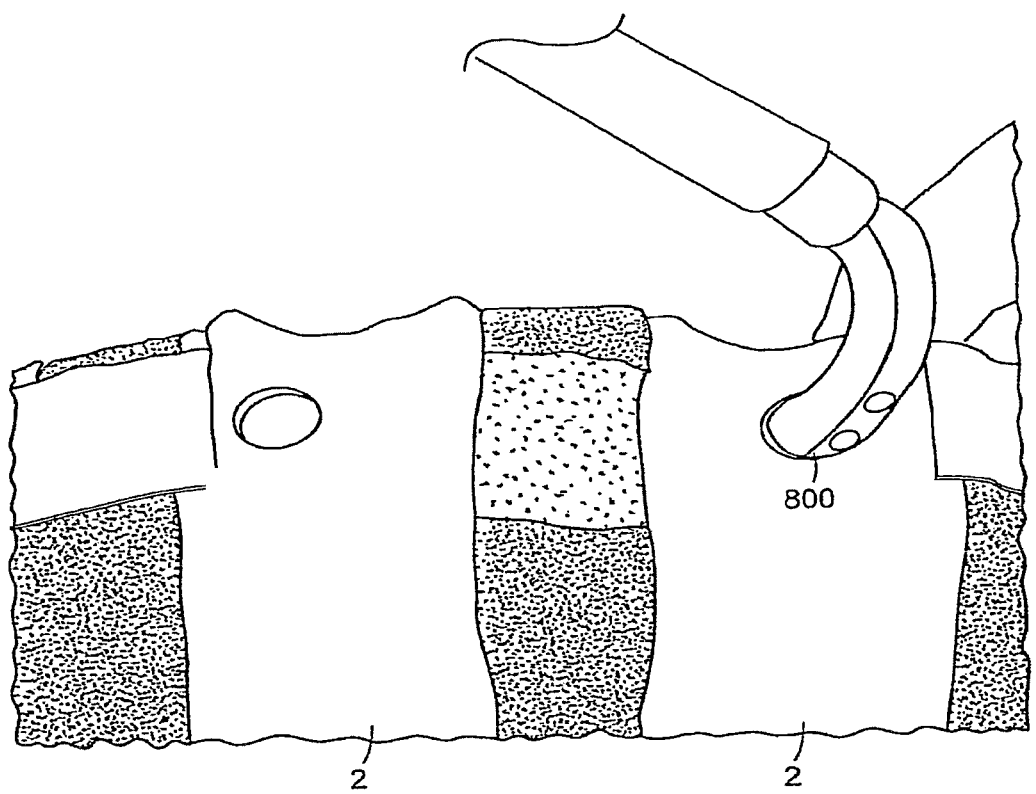
FIGS. 16A-C are illustrations of the process for implanting or attaching a curved rod in the through aperture and across the adjacent vertebrae.
Figure 16B:
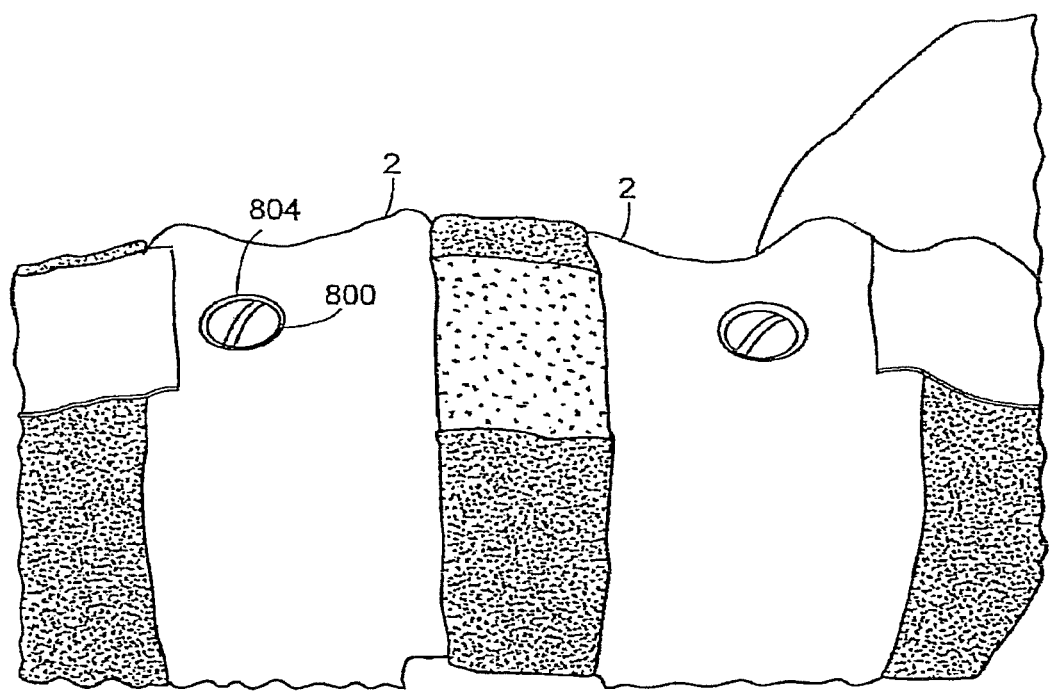
Figure 16C:
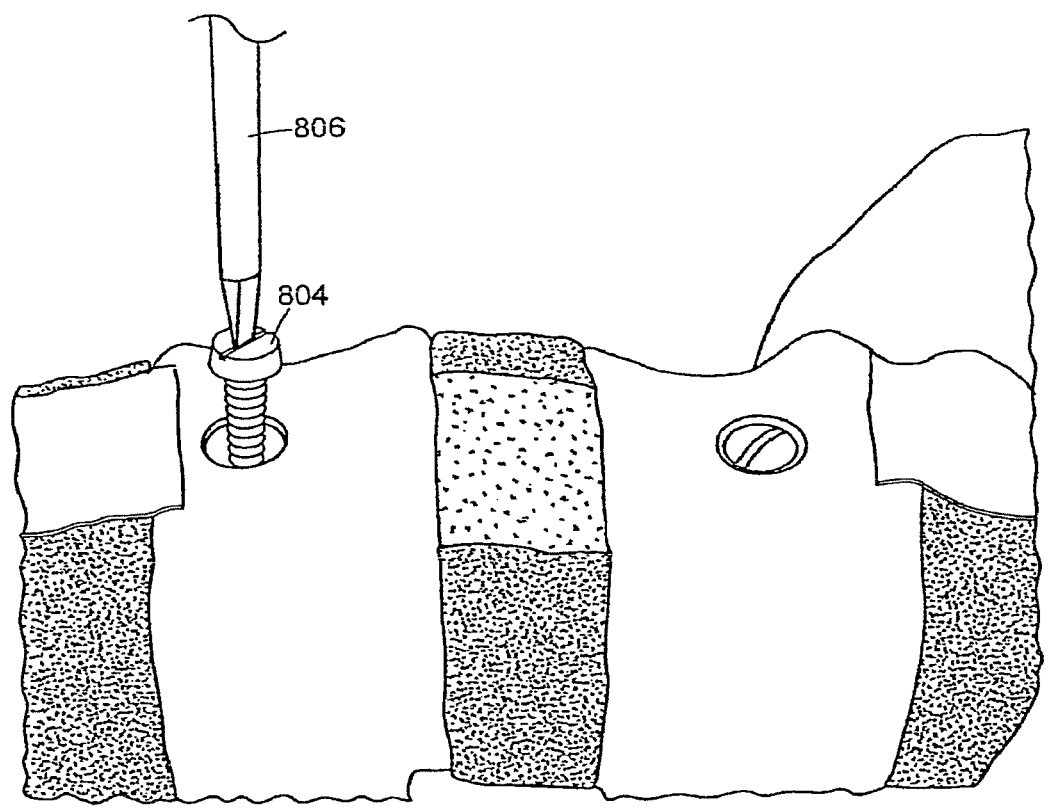

Now with reference to FIGS. 16A-C there is shown the process for placing, positioning and attaching or implanting a curved rod 800, including those described in any of U.S. Pat. Nos. 6,607,530 and 6,923,811. The curved rod 800 is inserted into the channel and manipulated so that the curved rod is submerged along the midline of the vertebra (see FIGS. 16A-B). The curved rod 800 is now secured to the vertebral bodies using interlocking screws 804 that traverse the rod and penetrate the vertebra at an angle that will avoid sensitive neurologic structures. The screws hold the curved rod 800 in place and stabilize the motion segment to facilitate healing of the bone within the disc space.

Two end screws 804 are passed through the open ends of the curved rod and each is inserted until the screw head is contained within the hollow of the implant. The screws are inserted using for example a Cardan screwdriver 806.

It should be recognized, and as taught in any of U.S. Pat. Nos. 6,607,530 and 6,923,811, that the curved rods 800 can be configured so as to include fenestration or surface artifacts that secure the curved rod within the channel without the retaining screws 804 are described above or in addition to such retaining screws.

Figure 19A:
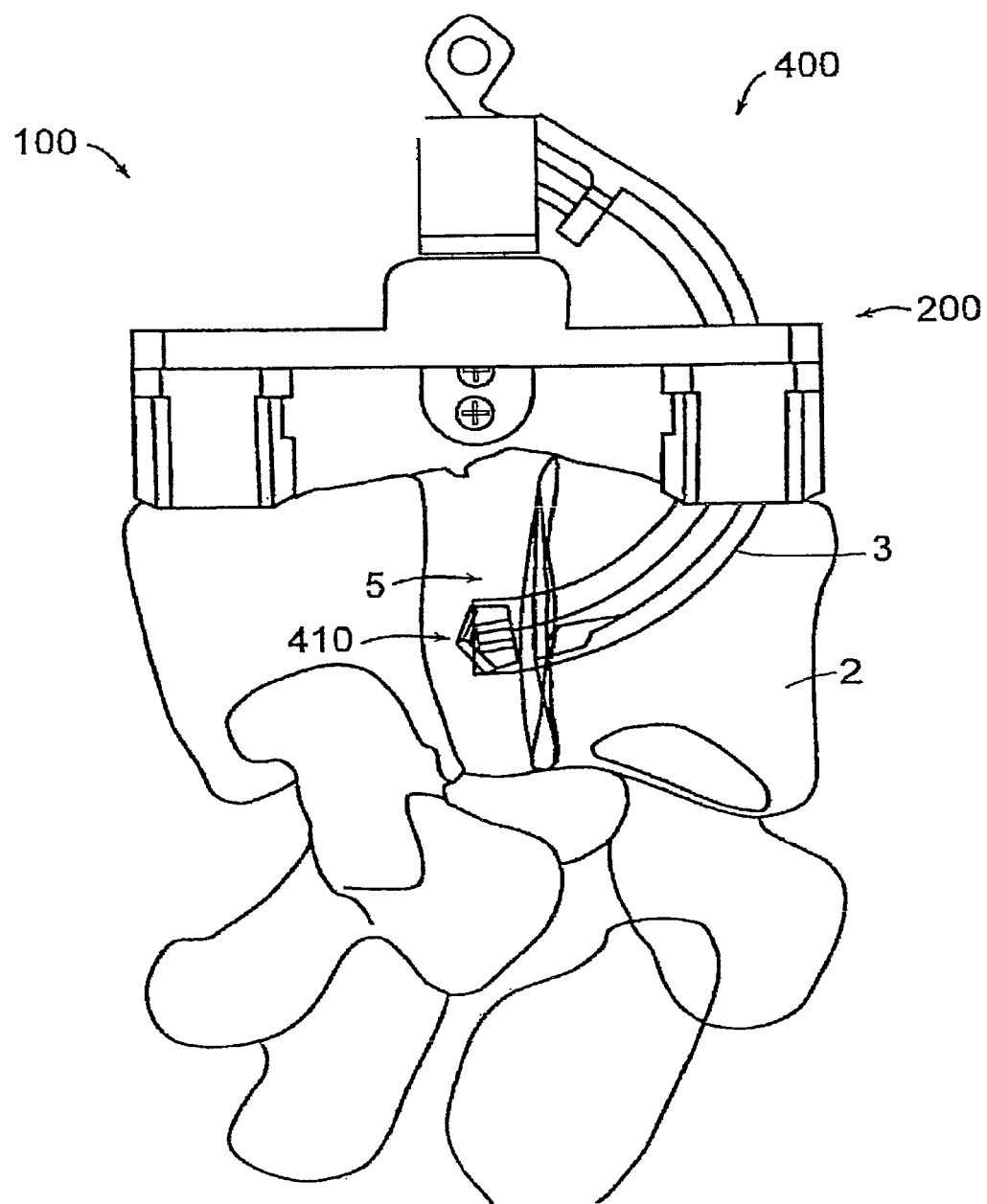
FIG. 19A is a perspective view of a portion of a spine on which is mounted a drilling apparatus of the present invention for creating a channel, passage or hole for a disk repair procedure.

As indicated herein, the drilling apparatus of the present invention is adaptable for use in a wide range of spinal repair procedures including but not limited to a repair procedure for an intervertebral disk 5 (FIG. 19A,B). Although the following discussion refers to the drilling apparatus 100 according to one aspect/embodiment of the present invention, it is contemplated that any of the drilling apparatuses herein described are adaptable for use to perform such a disk repair procedure. Also, it is contemplated that a disk repair procedure according to the present invention also can be accomplished using any of the devices, apparatuses or mechanisms described in and as taught in any of U.S. Pat. Nos. 6,607,530 and 6,923,811.

Figure 19B:
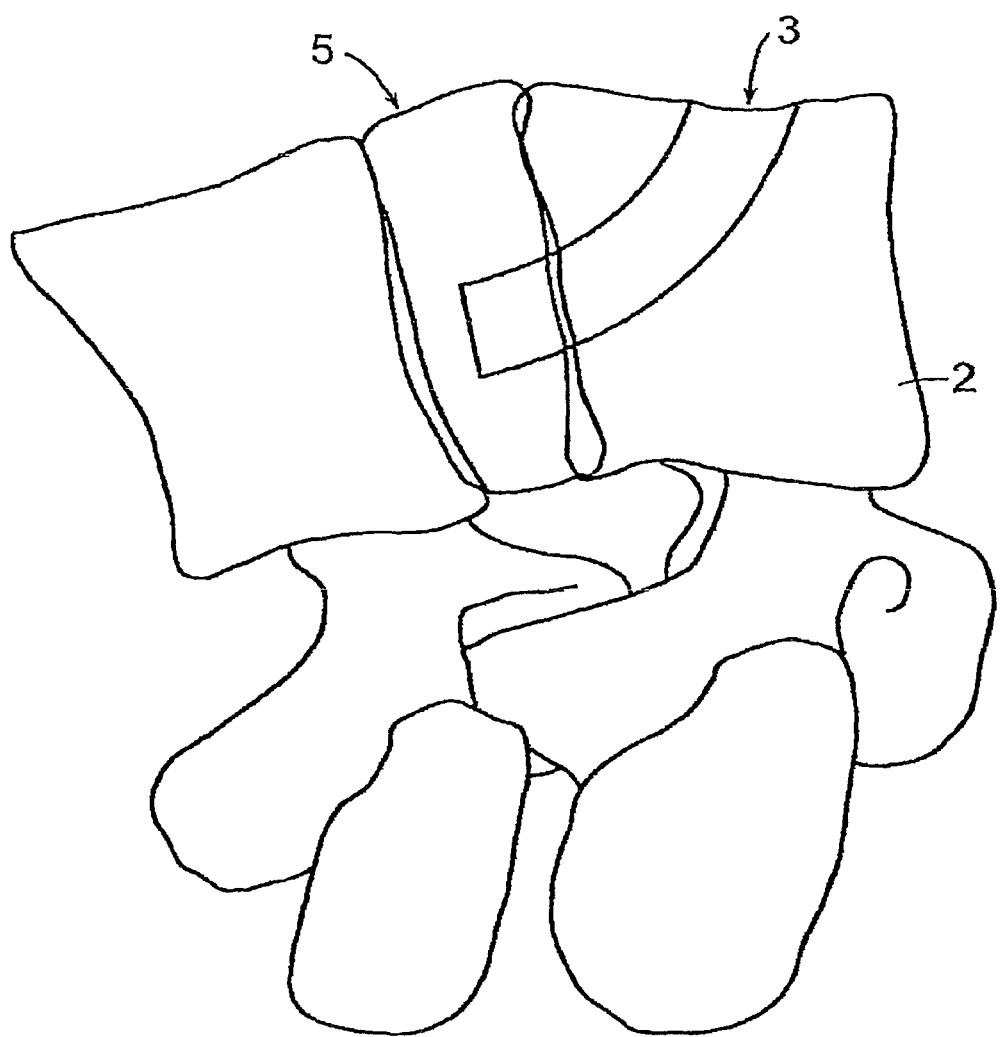
FIG. 19B is a perspective view of the portion of the spine illustrating the channel, passage or hole through an adjacent vertebrae allowing access to the nucleus.
Figure 20:
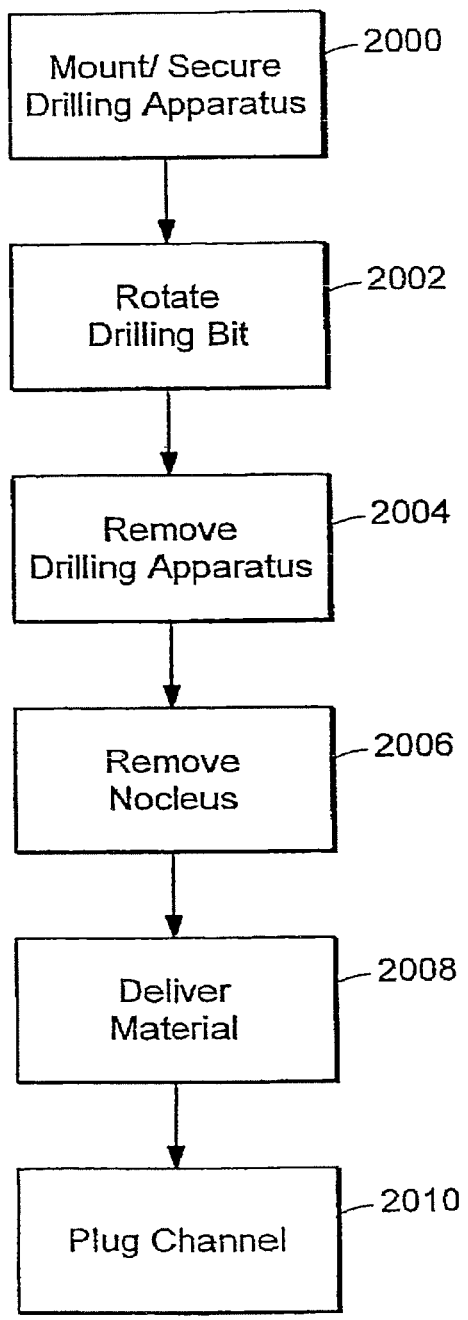
FIG. 20 is a flow diagram briefly describing a disk repair procedure according to the present invention.

Referring now to FIGS. 19A-B, there is shown a drilling apparatus 100 mounted/secured upon a spine, more specifically adjacent vertebrae 2, Step 2000. Such mounting and securing is accomplished using the methods and techniques for doing so as described herein. Reference shall be made to FIGS. 1-9 and the discussion related thereto, for further details of the drilling apparatus not provided below. Reference also should be made to the process flow diagram illustrated in FIG. 20.

In further embodiments, the drill bit 410 of the drilling apparatus 100 and related components are selected so that the channel, passage or hole 3 in the adjacent vertebrae 2 is sized so as to provide a desired access to the nucleus for carrying out the repair procedure. For example, the hole 3 may be one size if a fluid or gel is to be injected into the nucleus, whereas it may be made larger if a prosthetic or device is to be inserted through the hole so as to reside in the area within the annulus for the disk nucleus.

After the drilling apparatus 100 is so mounted, the surgeon manipulates the drill bit so as to cause it to rotate and create a curved or arcuate hole 3 in the adjacent vertebrae and into the disk 5, Step 2002. Such a drilling operation advantageously minimizes penetration of the vertebral endplates. Also, the drill as it follows the predetermined curved or arcuate path penetrates the vertebral end plates at essentially a right angle, thereby creating a circular defect. In contrast, the straight drill used in conventional techniques would penetrate the end plate at an angle thereby causing a larger elliptical shaped defect. The near perpendicular access created by the drilling apparatus of the present invention also minimizes trauma and/or disruption to the natural nucleus material. In contrast, a straight drill would need to penetrate more deeply into the disc space to complete the access hole.

In this regard it should be noted that while it is desirous to penetrate the nucleus of the disk, it should be recognized that it is possible that a portion of the annulus also may be drilled during the drilling procedure. Such an occurrence, however, shall not be construed as being unacceptable or outside the scope of the present invention.

Following creating of the hole, the drill bit 410 is extracted or removed from the hole 3 thereby allowing the surgeon access to the hole and thus the nucleus of the disk to be repaired. In particular embodiments, the surgeon removes the drilling apparatus 100 so as to provide clear access to the opening formed by the hole 3, Step 2004. Thereafter, the surgeon performs the particulars of the disk repair/replacing/augmentation procedure, such as but not limited to removing nucleus material (Step 2006), delivery of the nucleus augmentation material, artificial disk and/or artificial nucleus (Step 2008) and plugging of the channel, passage or hole 3 made in the adjacent vertebrae 2 (Step 2010). The nucleus material can be removed using any of a number of techniques known to those skilled in the art including but not limited to water jets, chemical agents such as Chymopapain chemonucleolysis, rongers and emulsification technology.

Such augmentation material includes but is not limited to the devices, mechanisms and materials described in U.S. Pat. Nos. 5,824,093, 6,264,695 and 5,047,055 the teachings of which are herein incorporated by reference. Also, such delivery of the nucleus augmentation material, as well as such repair procedures, can include delivery and positioning of an annulus closure mechanism or device to seal or retain the artificial disc, nucleus and/or nucleus augmentation material or provide a closure for a defect in the annulus, such as but no limited to the devices described in U.S. Pat. Nos. 6,425,919 and 6,593,625, the teaching of which are incorporated herein by reference. As is known to those skilled in the art, when the annulus becomes damaged a defect is formed in the annulus that allows the nucleus for example, to cause the disk to bulge in a given direction. In addition, to delivery of nucleus or annulus repair and augmentation materials, it also is contemplated that drugs, medicaments, or other treatment materials can be delivered to the disk 5, vertebrae 2 or other element of the body.

The plugging of the hole 3 is accomplished using any of a number of techniques known to those skilled in the art, including but not limited to the use of bone/bone graft material. It also is contemplated that an arcuate rod as herein described also can be used to plug the hole 3. Thus, the plugging of the hole 3 becomes a relatively straightforward procedure. Also, the plugging should advantageously create a relatively smooth surface at the end plate and the load forces on the vertebral end plate will be perpendicular to the access hole. Such plugging is particularly advantageous as compared to some conventional techniques as defects in the annulus do not heal; whereas defects in the bone (e.g., the vertebral body) can be plugged with bone, metal, etc. and the bone heals around the plug.

Figures 21, 22:
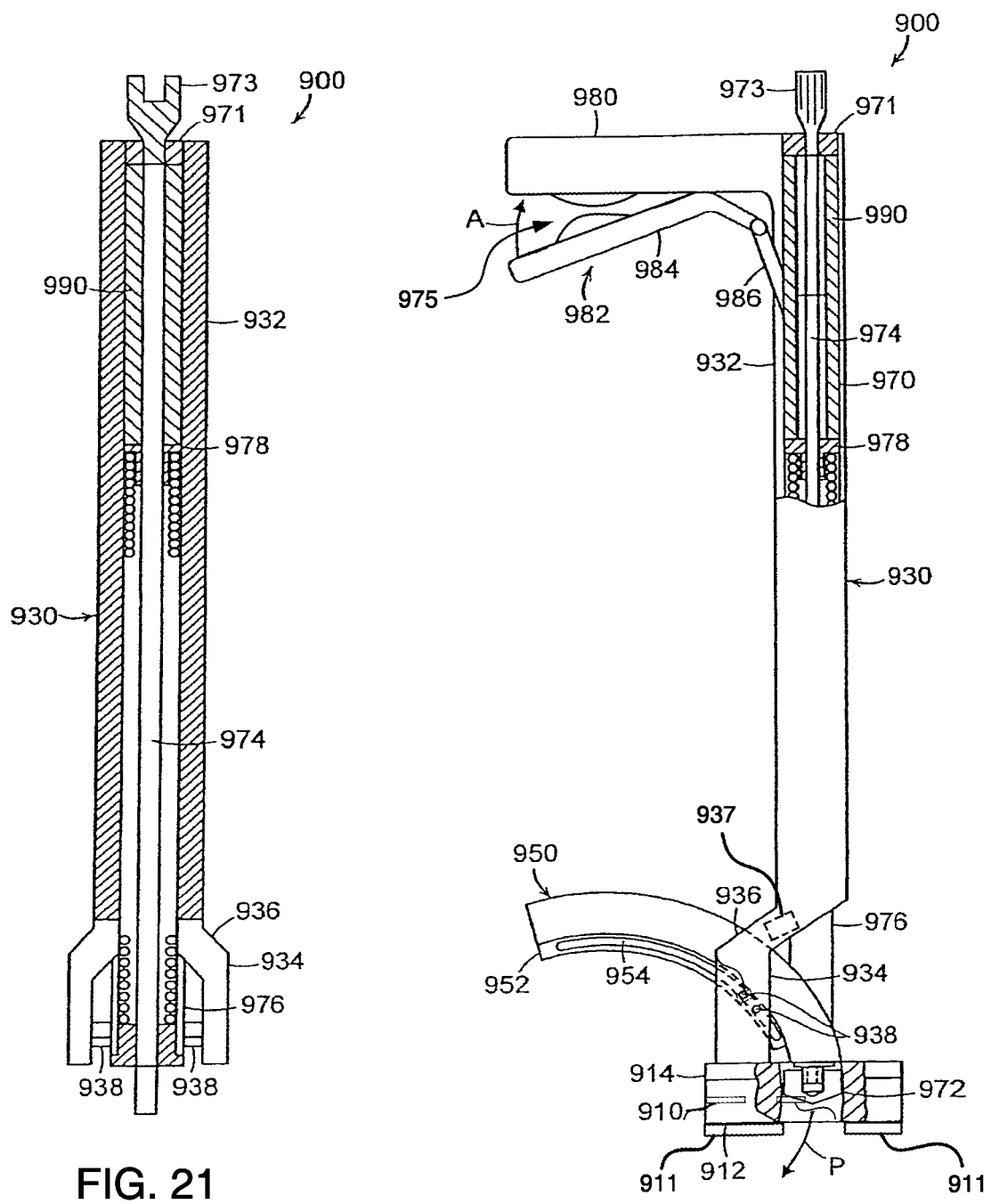
FIG. 21 is a front view of an alternative drilling apparatus for forming an arcuate channel in one or more segments of a bone, bony structure or adjacent vertebrae of a spine.
FIG. 22 is a side view of the drilling apparatus of FIG. 21.
Figure 23:
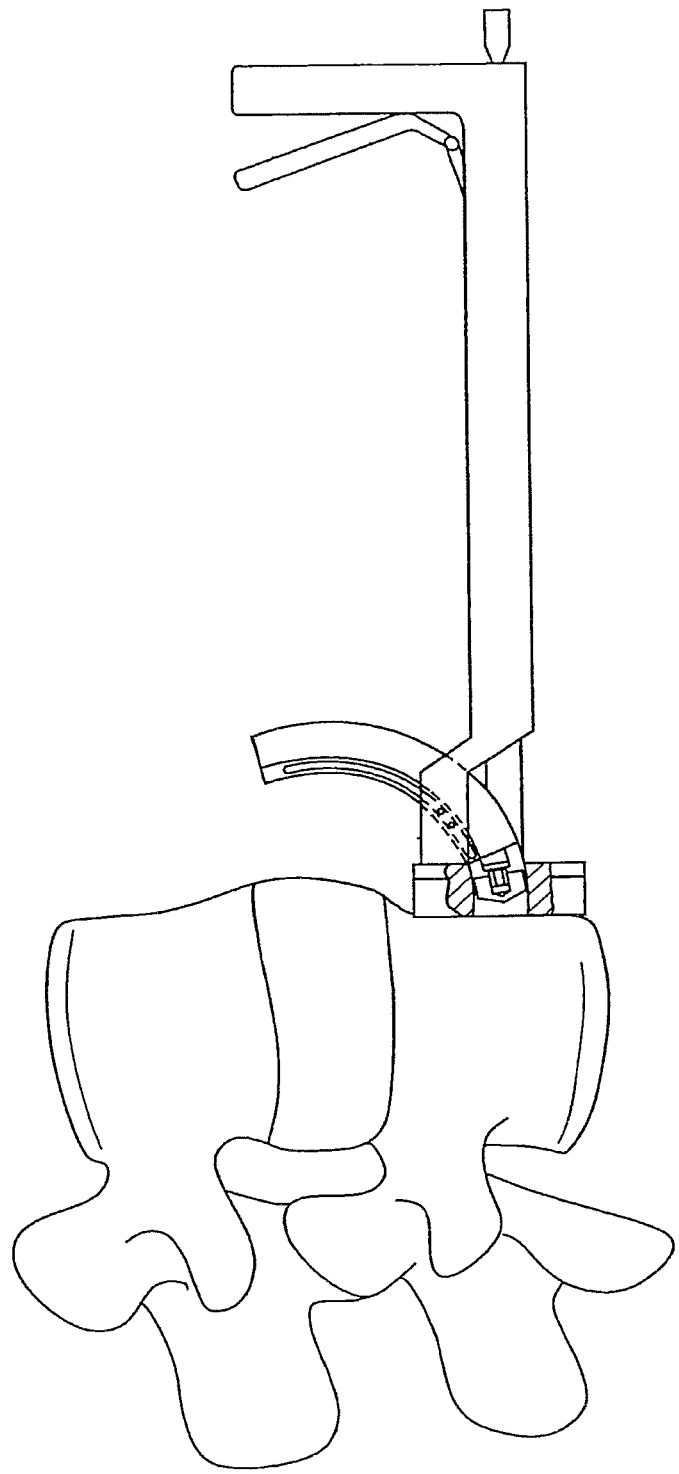
FIGS. 23-26 illustrate a method of use for the drilling apparatus of FIGS. 21 and 22.
Figure 24:
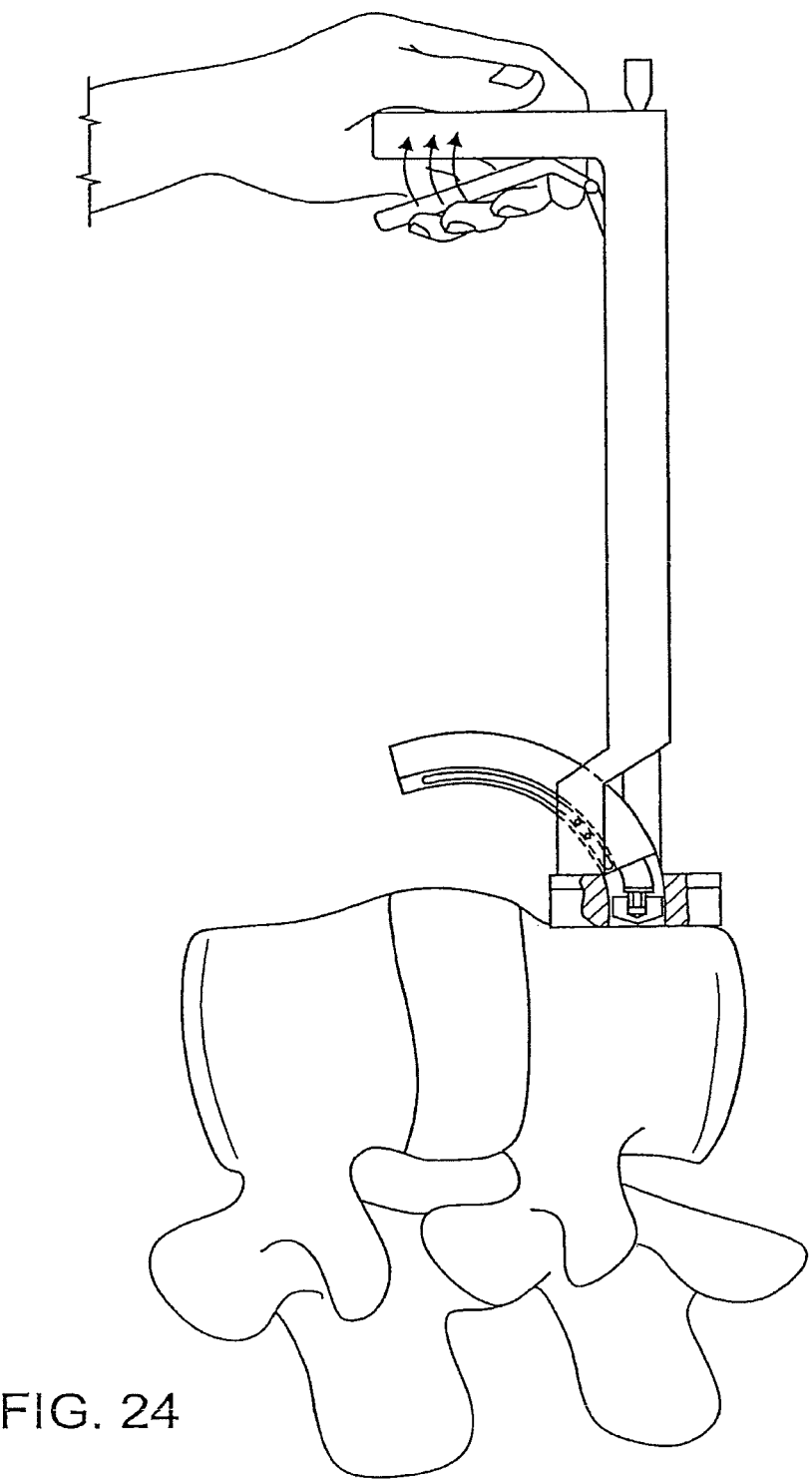
Figure 25:
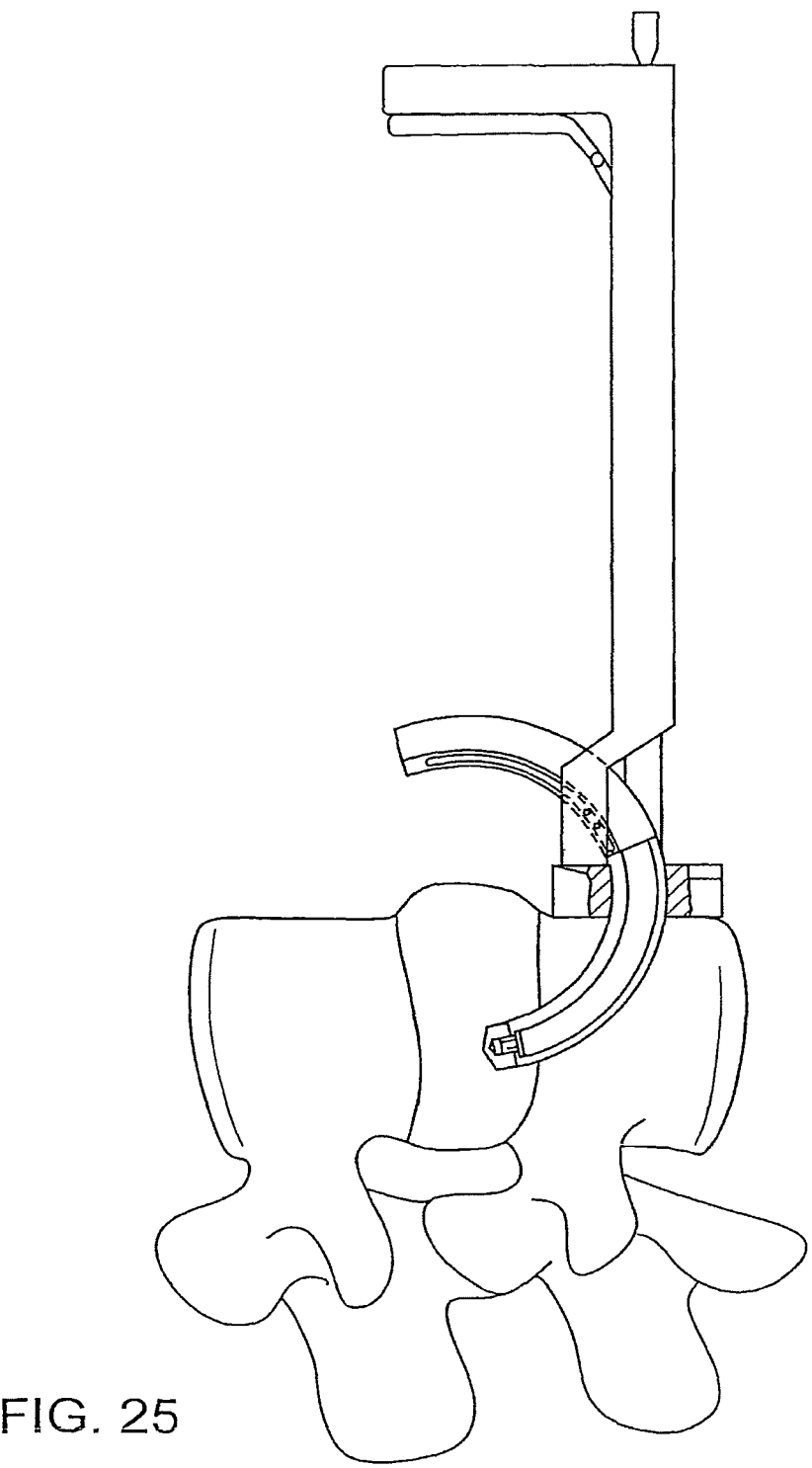
Figure 26:
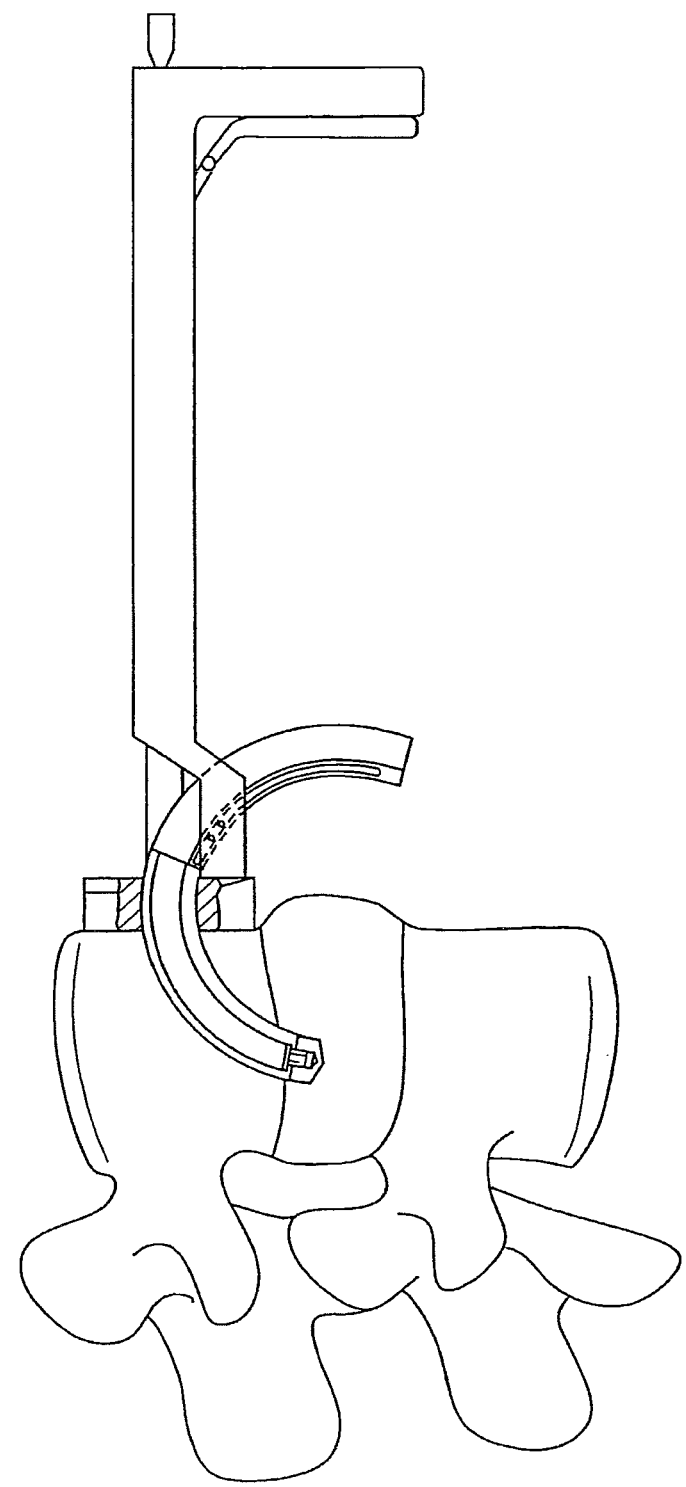

Referring now to FIGS. 21 and 22, there is illustrated a drilling apparatus according to yet another embodiment/aspect of the present invention which has been designated generally by reference numeral 900. The drilling apparatus 900 is adapted and configured for forming an arcuate channel in one or more segments of a bone, bony structure or adjacent vertebrae of a spine. The drilling apparatus includes, inter alia, a base member 910 which is positioned proximate to the bone, bony structure or adjacent vertebrae of a spine, a support arm 930, an arcuate guide member 950 and a drill assembly 970. The drilling apparatus 900 is designed such that it can be supported by a single bone, bony structure or vertebrae. Moreover, unlike prior drilling apparatuses, the drilling apparatus 900 can be adapted to extend to adjacent bone material or vertebrae so that an arcuate channel can be drilled therein.

The base member 910 has a distal surface 912 which is adapted to allow placement of the base member 910 proximal/adjacent to one of the bone, bony structure or vertebrae. The base member 910 can be manufactured from a variety of biocompatible materials, such as stainless steel. The material selected for the base member 910 should be of sufficient strength to provide non-movable support to the rest of the drilling apparatus 900 when the base member 910 is mechanically secured to the bone structure and when operation loads are applied to the system.

The support arm 930 extends in the proximal direction from the base member 910. For reasons that will be discussed below, it is preferred that the support arm 930 is removably secured to the base member 910; however, that should not be considered as limiting. Those skilled in the art will readily appreciate that a variety of mechanical mechanisms can be used to secure the support arm 930 to the base member 910 without departing from the scope of the present invention. The support arm 930 is formed in three segments; an upper segment 932, a lower segment 934, and a intermediate transition segment 936.

The arcuate guide member 950 is slidably mounted to the lower segment 934 of the support arm 930. In the embodiment illustrated in FIGS. 21 and 22, the arcuate guide member 950 has a substantially U-shaped cross-section. Two guide rails 952 or arms extend from the bottom of the guide member 950. Each guide rail 952 has an arcuate channel 954 formed therein which extends along its length and is dimensioned and configured for receiving the guide pins 938 associated with the lower segment 934 of the support arm 930.

The drill assembly 970 is operatively coupled to the support arm 930 and includes a drill bit 972 attached to the distal end of a flexible drive cable 974. The flexible drive cable 974 extends within the support arm 930 and is axially and rotationally movable with respect thereto. A drill connector 973 is provided on the proximal end of the flexible drive cable 974 for attaching to a conventional motor similar to those previously described. A stabilizer bearing 971 is positioned around the connector 973 to facilitate rotational movement of the connector 973 with respect to the support arm 930. The drill bit 972 is operatively coupled to an end of the arcuate guide member 950 such that when the drill assembly 970 is moved distally the arcuate guide member 950 slides with respect to the support arm 930 and forces the drill bit 972 to traverse an arcuate path as indicated by the arrow designated "P". The drill assembly 970 also includes a flexible outer housing 976 which surrounds the drive cable 974, but allows the drive cable 974 to move/rotate freely therein.

A handle 980 is attached to the proximal end of the support arm 930 which allows the surgeon to grasp the drilling apparatus 900 with a single hand. An actuator mechanism 982 is also associated with the upper portion 932 of the support arm 930 and handle 980. The actuator mechanism 982 includes an arm 984 which is mechanically engaged with a drive barrel 990 through a linkage assembly 986. When the surgeon grabs the arm 984 of the actuator 982 and pulls it towards the handle (indicated by the arrow designated "A"), the linkage assembly 986 exerts a downward force on the drive barrel 990. The drive barrel 990 is operatively connected to the outer housing 976 of the drill assembly 970 through a bushing 978. As a result, when a downward force is exerted on the drive barrel 990, a downward force is also exerted on the outer housing 976. Consequently, the drill assembly 970 is moved in a downward or distal direction between a first position, wherein the drill bit 972 is positioned outside of the bone, bony structure or vertebrae to a second position wherein the drill bit 972 is disposed within the bone, bony structure or vertebrae. In such embodiments, a biasing element is used to return the drill assembly 970 to the first position from the second position upon the completion of the drilling procedure.

The biasing element is any of a number of structures or devices known to those skilled in the art, that can cause the drill assembly 970 to return to the first position from the second position. For example, in illustrative exemplary embodiments the biasing element is a resilient member or structure 975 that is operably coupled to and between the handle 980 and the arm 984 of the actuator 982 such that when the surgeon grabs the actuator arm 984 and pulls it towards the handle the resilient structure/member is compressed. When the drilling procedure(s) is completed, the restoring force of the resilient structure/member 975 causes the actuator arm 984 to move away from the handle 980, which in turn causes the drill assembly 970 to return to the first position from the second position.

In more particular embodiments, the resilient structure/member 975 is a spring that extends between and is operably coupled to the handle 980 and the actuator arm 984. In another embodiment, the resilient structure/member 975 forms a hinge that is operably coupled to each of the handle 984 and the actuator arm 984. The hinge includes a spring element that is compressed when the actuator arm moves towards the handle. In yet another embodiment, the resilient structure/member 975 comprises one or more leaf springs that are operably coupled to the actuator arm 984 and/or the handle 980 so as to be compressed when the actuator arm moves towards the handle. It should be recognized that is within the skill of those knowledgeable in the art to configure and arrange a resilient member/structure that extends when the actuator arm 984 moves towards the handle 980 to create a restoring force.

The base member 910 also includes a mechanism for adjusting the location of the support arm and/or first position of the drill assembly with respect to the base member 910. In the embodiment illustrated in FIGS. 21 and 22, the mechanism for adjusting the lateral position of support arm is a plate 914. The plate 914 includes at least two slotted holes through which mechanical connector secure the plate 914 to the rest of the base member. It is the slotted holes that allow the lateral position of the plate 914 and therefore, the support arm 930 to be finely adjusted with respect to the rest of the base member. Additionally, plates with varying thickness can be used in conjunction with the plate 914 or in lieu of the plate 914 to adjust the height of the support arm 930 and the drill bit 972.

Those skilled in the art will readily appreciate that other mechanism can be used to adjust the lateral or axial position of the drill assembly with respect to the material to be drilled into without departing from the inventive aspects of the present disclosure. For example, different shape and size support arms can be used to vary the first position of the drill bit. Moreover, the intermediate transition segment 936 of the support arm can include a linkage assembly 937 or extension that allows for both lateral and axial adjustment of the location of the drill bit. It should be noted that depending on the magnitude of such an adjustment, an arcuate guide member having a different length and/or radius may be required.

As discussed with respect to the previously described drilling assemblies, the base member 910 can be mechanically attached to the bone using several techniques, such as nails or screws. Additionally, the base member 910 can include a plurality of through apertures formed therein which are configured and arranged so portions thereof proximal an exit of each of the plurality of through apertures contact at least a portion of a surface of the one of the bone, bony structure or vertebra so as to form an enclosed pathway from a top surface of the base to the surface of the one of the bone, bony structure or vertebra. Moreover, the base member 910 can include a soft conformable material 911 on the distal surface 912 thereof to effect a seal against the surface of the bone, bony structure or vertebrae.

FIGS. 23-26 illustrate a method of use for the drilling apparatus 900. Referring now to these figures, the drilling apparatus 900 is positioned in a anterior approach and proximal to the drilling or surgical site. The base member 910 is secured to one segment of the bone or bony structure or adjacent vertebra using the previously described techniques. The surgeon grabs the arm 984 of the actuator 982 and squeeze it towards the handle 980. The linkage assembly 986 exerts a downward force on the drive barrel 990, bushing 978 and drilling assembly 970. As a result, the drill assembly 970 is moved distally causing the arcuate guide member 950, which is operatively connected to the drill bit 972, to slide with respect to the support arm 930, forcing the drill bit 972 to traverse an arcuate path and form a channel in the surface or sub-surface of the bone, bony structure or vertebra.

If it is determined that only a partial channel in the bone material has been formed, the support arm 930 is detached from the base member 910, rotated 180 degrees and re-attached to the base member 910 such that the arcuate guide member 950 and the drill bit 972 are moveable in a second direction which opposes the first cutting direction.

It should be recognized that an advantage of the present invention is that drilling apparatus 900 can be sized, adapted and configured to ensure that it is impossible for the drill bit to come in contact with the spinal column. For example, the radius of guide member 950 can be selected such that the depth of the arcuate channel formed by the drilling operation is limited within an acceptable factor of safety to prevent any injury to the spinal column.

Those skilled in the art will readily appreciate that drilling apparatus 900 can be used in all of the aforementioned surgical procedures, such as to gain access to intreverebral disc space.

It should be recognized that the drilling apparatus, methods and systems of the present invention can be used anteriorally or posteriorally and so that the drill bit of such systems or apparatuses can penetrate or enter the vertebral body through the pedicles. In a posterior approach, the drilling can be accomplished in a transpedicular fashion or in a translateral fashion, wherein the drill bit enters anterior of the pedicle on the vertebral body.

In one method, open surgery to the posterior portion of a selected vertebral body is performed to expose a pedicle. Using drill assembly 900 a small access hole can be drilled into the pedicle and then onward through the marrow of the vertebral body and into the superior endplate of the vertebral body. The drill could then be rotated to perform a similar procedure on the inferior endplate. In such applications, arcuate channels would preferably be formed on both sides of the spine and curved rods inserted into each of the channels.

Figure 27:
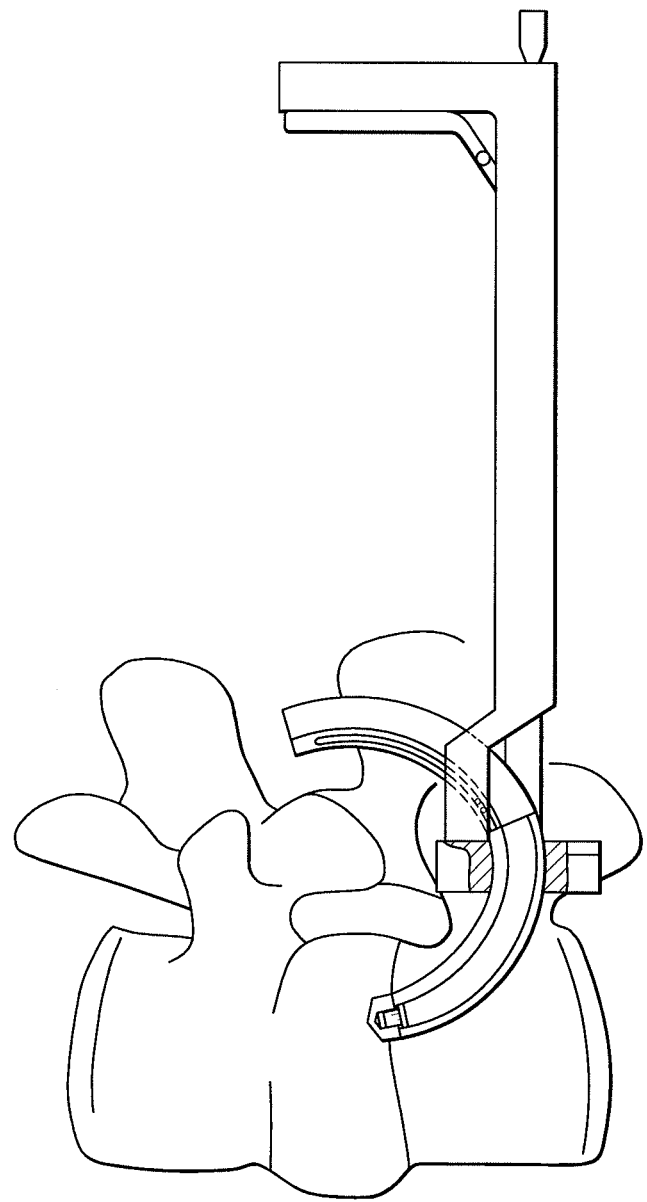
FIG. 27 illustrates a method of use for the drilling apparatus of FIGS. 21 and 22 when situated on the posterior aspect of the spine.

In another method of the present invention, a drill assembly 900 is situated on the posterior aspect of the spine. For example, there is shown in FIG. 27, a drill assembly on the pedicle of the posterior column, however the drill could also be seated on the trans-lateral aspect which is a common approach for interbody fusion (trans-lateral interbody fusion (TLIF)). When situated on the pedicle, the method would further include preparation of the pedicle, so that the arc of the drill will translate to the inner portion of the disc space. Once the pedicle of the spine is prepared, the drill is attached to the spine and an arc is created through the adjacent vertebral bodies in the same way as has been described in FIGS. 23-26.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications, US patent application and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. An apparatus for forming an arcuate channel in one or more segments of a bone, bony structure or adjacent vertebrae of a spine, the apparatus comprising:
 a) a base member having a distal surface adapted for placement adjacent to one of the bone, bony structure or vertebrae;
 b) means for fixing the position of the base member relative to one of the bone, bony structure or vertebrae;
 c) a support arm extending proximally from the base member;
 d) an arcuate guide member slidably mounted to the support arm;

e) a drill assembly operatively coupled to the support arm and including a drill bit attached to a distal end of a flexible drive cable which extends axially along the support arm and is axially and rotationally movable with respect thereto; and wherein the drill bit is operatively coupled to an end of the arcuate guide member such that when the drill assembly is moved distally the arcuate guide member slides with respect to the support arm and forces the drill bit to traverse an arcuate path.

2. The apparatus as recited in claim 1, wherein the arcuate guide member includes as least one guide rail defining an arcuate channel dimensioned and configured for receiving a guide pin to slidably mount the arcuate guide member to the support arm.

3. The apparatus as recited in claim 1, further comprising a handle attached to a proximal end of the support arm.

4. The apparatus as recited in claim 1, further comprising an actuator mechanism associated with a proximal end of the support arm for moving the drill assembly between a first position, wherein the drill bit is positioned outside of the bone, bony structure or vertebrae to a second position wherein the drill bit is disposed within the bone, bony structure or vertebrae.

5. The apparatus as recited in claim 4, further comprising a biasing element for returning the drill assembly to the first position from the second position.

6. The apparatus as recited in claim 4, further comprising a mechanism for adjusting location of the support arm and the first position of the drill assembly with respect to the base member.

7. The apparatus as recited in claim 6, wherein the mechanism for adjusting the location of the support arm and the first position of the drill assembly with respect to the base member includes a lateral adjustment mechanism and/or an axial adjustment mechanism.

8. The apparatus as recited in claim 1, wherein the support arm is tubular and the flexible drive cable extends substantially along a centerline of the support arm.

9. The apparatus as recited in claim 1, wherein the means for fixing the position of the base member relative to one of the bone, bony structure or vertebrae includes a securing mechanism for securing the base member to one of the bone, bony structure or vertebrae.

10. The apparatus as recited in claim 9, wherein the securing mechanism includes screws which engage with one of the bone, bony structure or vertebrae.

11. The apparatus as recited in claim 9, wherein the base member includes a plurality of first through apertures and wherein the base member is configured and arranged so portions thereof proximal an exit of each of the plurality of first through apertures contact at least a portion of a surface of the one of the bone, bony structure or vertebra so as to form an enclosed pathway from a top surface of the base to the portion of the surface of the one of the bone, bony structure or vertebra.

12. The apparatus as recited in claim 11, wherein the securing mechanism comprises a plurality of members one end of which is configured for mechanical engagement with the one of the bone, bony structure or vertebra.

13. The apparatus as recited in claim 12, wherein the base member further includes a plurality of second through apertures extending between a top surface and a bottom surface thereof and wherein one of the plurality of members of the securing mechanism is received in a respective one of the plurality of second through apertures.

14. The apparatus as recited in claim 13, wherein each of the plurality of second through apertures is configured and arranged so a portion thereof mechanically engages a portion of one of the plurality of members of the securing mechanism received therein.

15. The apparatus as recited in claim 14, wherein each of the plurality of second through apertures is configured and arranged so the one end of the plurality of members of the securing mechanism configured for mechanical engagement with the one of the bone, bony structure or vertebrae is disposed within confines of the second through aperture before causing the one end to mechanically engage.

16. The apparatus as recited in claim 1, wherein the base member includes a soft conformable material on the distal surface thereof to affect a seal against a surface of the bone, bony structure or vertebrae.

17. The apparatus as recited in claim 1, wherein the drill assembly includes a flexible outer housing which surrounds the drive cable.

18. The apparatus as recited in claim 1, wherein the arcuate guide member has a substantially U-shaped cross section.

19. The apparatus as recited in claim 1, wherein the arcuate guide member includes first and second arms that each have an arcuate slot formed therein which are configured to receive guide pins projecting from the support arm.

20. A system for forming an arcuate channel in one or more segments of a bone, bony structure or adjacent vertebrae of a spine, the system comprising:
   a) a base member having a distal surface adapted for placement adjacent to one of the bone, bony structure or vertebrae;
   b) a securing mechanism for securing the base member to one of the bone, bony structure or vertebrae;
   c) a support arm extending proximally from the base member;
   d) an arcuate guide member having a substantially U-shaped cross-section slidably mounted to the support arm;
   e) a drill assembly operatively coupled to the support arm and including a drill bit attached to a distal end of a flexible drive cable which extends axially along the support arm and is axially and rotationally movable with respect thereto; and
   wherein the drill bit is operatively coupled to an end of the arcuate guide member such that when the drill assembly is moved distally the arcuate guide member slides with respect to the support arm and forces the drill bit and a portion of the flexible drive cable to traverse an arcuate path.

21. The apparatus as recited in claim 20, further comprising a handle attached to a proximal end of the support arm.

22. The apparatus as recited in claim 20, further comprising an actuator mechanism associated with a proximal end of the support arm for moving the drill assembly between a first position, wherein the drill bit is positioned outside of the bone, bony structure or vertebrae to a second position wherein the drill bit is disposed within the bone, bony structure or vertebrae.

23. The apparatus as recited in claim 22, further comprising a biasing element for returning the drill assembly to the first position from the second position.

24. The apparatus as recited in claim 22, further comprising a mechanism for adjusting a location of the support arm and the first position of the drill assembly with respect to the base member.

25. The apparatus as recited in claim 24, wherein the mechanism for adjusting the location of the support arm and the first position of the drill assembly with respect to the base member includes a lateral adjustment mechanism and/or a axial adjustment mechanism.

26. The apparatus as recited in claim 20, wherein the support arm is tubular and the flexible drive cable extends substantially along a centerline of the support arm.

27. The apparatus as recited in claim 26, wherein the securing mechanism for securing the base member includes screws which engage with one of the bone, bony structure or vertebrae.

28. The apparatus as recited in claim 20, wherein the base member includes a plurality of first through apertures and wherein the base member is configured and arranged so portions thereof proximal an exit of each of the plurality of first through apertures contact at least a portion of a surface of the one of the bone, bony structure or vertebra so as to form an enclosed pathway from a top surface of the base member to the portion of the surface of the one of the bone, bony structure or vertebra.

29. The apparatus as recited in claim 28, wherein the securing mechanism comprises a plurality of members one end of which is configured for mechanical engagement with the one of the bone, bony structure or vertebra.

30. The apparatus as recited in claim 29, wherein the base member further includes a plurality of second through apertures extending between a top surface and a bottom surface thereof and wherein one of the plurality of members of the securing mechanism is received in a respective one of the plurality of second through apertures.

31. The apparatus as recited in claim 30, wherein each of the plurality of second through apertures is configured and arranged so a portion thereof mechanically engages a portion of the one of the members of the securing mechanism received therein.

32. The apparatus as recited in claim 31, wherein each of the plurality of second through apertures is configured and arranged so the one end of the plurality of members of the securing mechanism configured for mechanical engagement with the one of the bone, bony structure or vertebrae is disposed within confines of the second through aperture before causing the one end to mechanically engage.

33. The apparatus as recited in claim 20, wherein the base member includes a soft conformable material on the distal surface thereof to effect a seal against a surface of the bone, bony structure or vertebrae.

34. The apparatus as recited in claim 20, wherein the drill assembly includes a flexible outer housing which surrounds the flexible drive cable.

35. The apparatus as recited in claim 20, wherein the arcuate guide member includes first and second arms that each have an arcuate slot formed therein which are configured to receive guide pins projecting from the support arm.

* * * * *